US008981112B2

(12) United States Patent
Bukhtiyarov et al.

(10) Patent No.: US 8,981,112 B2
(45) Date of Patent: Mar. 17, 2015

(54) INHIBITORS OF β-SECRETASE

(71) Applicants: Boehringer Ingelheim International GmbH, Ingelheim Am Rhein (DE); Vitae Pharmaceuticals, Inc., Fort Washington, PA (US)

(72) Inventors: Yuri Bukhtiyarov, Boothwyn, PA (US); Salvacion Cacatian, Conshohocken, PA (US); Lawrence Wayne Dillard, Yardley, PA (US); Cornelia Dorner-Ciossek, Ingelheim Am Rhein (DE); Klaus Fuchs, Ingelheim Am Rhein (DE); Lanqi Jia, Horsham, PA (US); Deepak S. Lala, Lower Gwynedd, PA (US); Angel Morales-Ramos, Blue Bell, PA (US); Jonathan Reeves, Ridgefield, CT (US); Suresh B. Singh, Kendall Park, NJ (US); Shankar Venkatraman, Lansdale, PA (US); Zhenrong Xu, Chalfont, PA (US); Jing Yuan, Lansdale, PA (US); Yi Zhao, Blue Bell, PA (US); Yajun Zheng, Hockessin (DE); Georg Rast, Ingelheim Am Rhein (DE)

(73) Assignees: Vitae Pharmaceuticals, Inc., Fort Washington, PA (US); Boehringer-Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/784,032

(22) Filed: Mar. 4, 2013

(65) Prior Publication Data
US 2013/0289050 A1 Oct. 31, 2013

Related U.S. Application Data

(60) Provisional application No. 61/606,786, filed on Mar. 5, 2012.

(51) Int. Cl.
*C07D 235/02* (2006.01)
*C07D 403/06* (2006.01)
*C07D 405/04* (2006.01)
*C07D 405/06* (2006.01)
*C07C 313/06* (2006.01)
*C07D 407/06* (2006.01)
*C07C 49/697* (2006.01)
*C07C 255/47* (2006.01)
*C07C 49/747* (2006.01)
*C07C 331/14* (2006.01)
*C07C 229/50* (2006.01)
*C07C 49/755* (2006.01)

(52) U.S. Cl.
CPC ............ *C07D 235/02* (2013.01); *C07C 313/06* (2013.01); *C07D 405/06* (2013.01); *C07D 407/06* (2013.01); *C07D 403/06* (2013.01); *C07C 49/697* (2013.01); *C07C 255/47* (2013.01); *C07C 49/747* (2013.01); *C07C 331/14* (2013.01); *C07C 229/50* (2013.01); *C07C 49/755* (2013.01)
USPC ......... 548/301.1; 544/230; 514/256; 514/388

(58) Field of Classification Search
CPC ............ C07D 235/02; C07D 4003/06; C07D 405/04; C07D 405/06
USPC ...................................................... 548/301.1
See application file for complete search history.

(56) References Cited

U.S. PATENT DOCUMENTS

| 4,874,869 | A | 10/1989 | Ueda et al. |
|---|---|---|---|
| 5,430,048 | A | 7/1995 | Gadwood |
| 7,423,158 | B2 | 9/2008 | Malamas et al. |
| 7,607,246 | B2 | 10/2009 | Valiyambath Krishnan et al. |
| 7,872,009 | B2 | 1/2011 | Albrecht et al. |
| 8,426,447 | B2 | 4/2013 | White et al. |
| 8,450,308 | B2 | 5/2013 | Dillard et al. |
| 8,633,212 | B2 * | 1/2014 | Cacatian et al. ............. 514/267 |
| 2005/0282825 | A1 | 12/2005 | Malamas et al. |
| 2005/0282826 | A1 | 12/2005 | Malamas et al. |
| 2006/0111370 | A1 | 5/2006 | Zhu et al. |
| 2006/0281730 | A1 | 12/2006 | Zhu et al. |
| 2006/0287294 | A1 | 12/2006 | Zhu et al. |

(Continued)

FOREIGN PATENT DOCUMENTS

| WO | 93/05045 A1 | 3/1993 |
|---|---|---|
| WO | 95-30642 A1 | 11/1995 |

(Continued)

OTHER PUBLICATIONS

Michael S. Malamas et al., Aminoimidazoles as Potent and Selective Human Beta-Secretase (BACE1) Inhibitors; J. Med. Chem. (2009), 52, 6314-6323.

Pawel Nowak et al.; Discovery and initial optimization of 5,50-disubstituted aminohydantoins as potent b-secretase (BACE1) inhibitors; Bioorganic & Medicinal Chemistry Letters 20 (2010) 632-635.

Michael S. Malamas et al.; Design and Synthesis of 5,5'-Disubstituted Aminohydantoins as Potent and Selective Human Beta-Secretase (BACE1) Inhibitors; J. Med. Chem. (2010), 53, 1146-1158.

(Continued)

*Primary Examiner* — Laura L. Stockton
(74) *Attorney, Agent, or Firm* — McCarter & English, LLP; Steven G. Davis; Xin Zhang

(57) ABSTRACT

The present invention relates to spirocyclic acylguanidines and their use as inhibitors of the β-secretase enzyme (BACE1) activity, pharmaceutical compositions containing the same, and methods of using the same as therapeutic agents in the treatment of neurodegenerative disorders, disorders characterized by cognitive decline, cognitive impairment, dementia and diseases characterized by production of β-amyloid aggregates.

17 Claims, No Drawings

(56) References Cited

U.S. PATENT DOCUMENTS

| | | |
|---|---|---|
| 2007/0004730 A1 | 1/2007 | Zhou et al. |
| 2007/0004786 A1 | 1/2007 | Malamas et al. |
| 2007/0027199 A1 | 2/2007 | Malamas et al. |
| 2007/0072925 A1 | 3/2007 | Malamas et al. |
| 2007/0203116 A1 | 8/2007 | Quagliato et al. |
| 2007/0287692 A1 | 12/2007 | Wu et al. |
| 2009/0209529 A1 | 8/2009 | Andreini et al. |
| 2011/0071126 A1 | 3/2011 | Cacatian et al. |
| 2011/0152253 A1 | 6/2011 | Motoki et al. |
| 2012/0065195 A1 | 3/2012 | Clark et al. |
| 2012/0087237 A1 | 4/2012 | Pellizzoni et al. |
| 2013/0053377 A1 | 2/2013 | Dillard et al. |
| 2013/0289050 A1 | 10/2013 | Bukhtiyarov et al. |

FOREIGN PATENT DOCUMENTS

| | | | |
|---|---|---|---|
| WO | 20051058311 A1 | 6/2005 | |
| WO | 20061065277 A2 | 6/2006 | |
| WO | 2007016012 A2 | 2/2007 | |
| WO | 2007038271 A1 | 4/2007 | |
| WO | 2007049532 A1 | 5/2007 | |
| WO | 2007063114 A2 | 6/2007 | |
| WO | 2007076284 A2 | 7/2007 | |
| WO | 2007078813 A2 | 7/2007 | |
| WO | 2007100536 A1 | 9/2007 | |
| WO | 2008010481 A1 | 1/2008 | |
| WO | 20081030412 A2 | 3/2008 | |
| WO | 2008076043 A1 | 6/2008 | |
| WO | 2008076044 A1 | 6/2008 | |
| WO | 2008076045 A1 | 6/2008 | |
| WO | 2008076046 A1 | 6/2008 | |
| WO | 20081103351 A2 | 8/2008 | |
| WO | 2008115552 A1 | 9/2008 | |
| WO | 2008118379 A2 | 10/2008 | |
| WO | 2008133273 A1 | 11/2008 | |
| WO | 2008133274 A1 | 11/2008 | |
| WO | 2008150217 A1 | 12/2008 | |
| WO | 2009134617 A1 | 11/2009 | |
| WO | 2010013302 A1 | 2/2010 | |
| WO | 2010013794 A1 | 2/2010 | |
| WO | 20101021680 A2 | 2/2010 | |
| WO | 20101105179 A2 | 9/2010 | |
| WO | 2011072064 A1 | 6/2011 | |
| WO | 20111106414 A1 | 9/2011 | |
| WO | 2012087237 A1 | 6/2012 | |
| WO | 2013134085 A1 | 9/2013 | |

OTHER PUBLICATIONS

Zhaoning Zhu et al.; Discovery of Cyclic Acylguanidines as Highly Potent and Selective Beta-Site Amyloid Cleaving Enzyme (BACE) Inhibitors: Part I Inhibitor Design and Validation; J. Med. Chem. (2010), 53, 951-965.

Michael S. Malamas; Di-substituted pyridinyl aminohydantoins as potent and highly selective human Beta-secretase (BACE1) inhibitors; Bioorganic & Medicinal Chemistry 18 (2010) 630-639.

Yu-Sen Wang et al.; Application of Fragment-BasedNMR Screening, X-ray Crystallography, Structure-Based Design, and Focused Chemical Library Design to Identify Novel MicroM Leads for the Development of nM BACE-1 ( Beta-Site APP Cleaving Enzyme 1) Inhibitors; J. Med. Chem. (2010), 53, 942-950.

R. Silvestri, "Boom in the Developemnt of Non-Peptidic β-Secretase (MACE1) Inhibitors for the Treatment of Alzheimer's Disease", Medicinal Research Reviews, (2009), vol. 29, No. 2, 295-338.

International Search Report for related PCT/US2010/027173; Sep. 6, 2010.

Written Opinion for related PCT/US2010/027173; Sep. 6, 2010.

International Search Report for related PCT/US2009/004686; Feb. 12, 2010.

Written Opinion for related PCT/US2009/004686; Feb. 12, 2010.

Gadwood et al. "Synthesis and Biological Activity of Spirocyclic Benzopyran Imidazolone Potassium Channel Openers," J. Med. Chem., vol. 36(10):1480-1487 (1993).

CAPLUS 2008:1339943 (Nov. 2008).

CA 149:307845 (Sep. 2008).

Hunt, Kevin W., et al, Spirocyclic Beta?Site Amyloid Precursor Protein Cleaving Enzyme 1 (BACE1) Inhibitors: From Hit to Lowering of Cerebrospinal Fluid (CSF) Amyloid ? in a Higher Species, Journal of Medicinal Chemistry 56(8):3379-3403 (2013).

International Search Report for related PCT/US2011/025912: Apr. 1, 2011.

Written Opinion for related PCT/US2011/025912: Apr. 1, 2011.

International Search Report for related PCT/US2013/028796: May 3, 2013.

Written Opinion for related PCT/US2011/028796: May 3, 2013.

International Search Report for related PCT/US2013/028796: Apr. 1, 2011.

Hunt, Kevin W., et al, Spirocyclic ??Site Amyloid Precursor Protein Cleaving Enzyme 1 (BACE1) Inhibitors: From Hit to Lowering of Cerebrospinal Fluid (CSF) Amyloid ? in a Higher Species, Journal of Medicinal Chemistry 56(8):3379-3403 (2013).

Written Opinion for related PCT/US2011/025912: May 3, 2013.

International Preliminary Report on Patentability for related International Patent Application No. PCT/US2013/056566, Dated: Aug. 19, 2014.

International Search Report and Written Opinion for related International Application No: PCT/US2013/056566, Dated: Nov. 8, 2013.

Hunt, Kevin W., et al, Spirocyclic Beta-Site Amyloid Precursor Protein Cleaving Enzyme 1 (BACE1) Inhibitors: From Hit to Lowering of Cerebrospinal Fluid (CSF) Amyloid Beta in a Higher Species, Journal of Medicinal Chemistry 56(8):3379-3403 (2013).

Written Opinion for related PCT/US2013/028796, Dated: May 3, 2013.

* cited by examiner

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
```

```
        Synthetic peptide"
<220> FEATURE:
<221> NAME/KEY: MOD_RES
<222> LOCATION: (1)..(1)
<223> OTHER INFORMATION: HiLyte FluorTM488-Glu
<220> FEATURE:
<221> NAME/KEY: MOD_RES
<222> LOCATION: (9)..(9)
<223> OTHER INFORMATION: Lys-(QXLTM520)-OH
<400> SEQUENCE: 1
Glu Val Asn Leu Asp Ala Glu Phe Lys
1               5
```

INHIBITORS OF β-SECRETASE

RELATED APPLICATIONS

This application claims the benefit of U.S. Provisional Application Ser. No. 61/606,786, filed Mar. 5, 2012, the entire teachings of which are incorporated herein by reference.

SEQUENCE LISTING

The instant application contains a Sequence Listing which has been submitted in ASCII format via EFS-Web and is hereby incorporated by reference in its entirety. Said ASCII copy, created on Mar. 4, 2013, is named 15161953.txt and is 718 bytes in size.

FIELD OF THE INVENTION

The present invention relates to spirocyclic acylguanidines and their use as inhibitors of the β-secretase enzyme (BACE1) activity, pharmaceutical compositions containing the same, and methods of using the same as therapeutic agents in the treatment of neurodegenerative disorders, disorders characterized by cognitive decline, cognitive impairment, dementia and diseases characterized by production of β-amyloid deposits or neurofibrillary tangles.

BACKGROUND OF THE INVENTION

β-Amyloid (also referred to herein as "Abeta" or "Aβ") deposits and neurofibrillary tangles are two major pathologic characterizations associated with Alzheimer's disease (AD), including the genetically linked early onset familial forms due to mutations in amyloid precursor protein (APP), presenilin 1 and 2, as well as late onset sporadic AD. Clinically, AD is characterized by the loss of memory, cognition, reasoning, judgment, and orientation. Also affected, as the disease progresses, are motor, sensory and linguistic abilities until global impairment of multiple cognitive functions occurs. These cognitive losses take place gradually, but typically lead to severe impairment and eventual death in 4-12 years.

β-Amyloid deposits are predominantly an aggregate of Abeta peptide, which in turn is a product of the proteolysis of APP. More specifically, Aβ peptide results from the cleavage of APP at the C-terminals by one or more γ-secretases, and at the N-terminus by β-secretase enzyme (BACE1), also known as aspartyl protease and memapsin2, as part of the β-amyloidogenic pathway.

BACE activity is correlated directly to the generation of Aβ peptide from APP, and studies increasingly indicate that the inhibition of BACE inhibits the production of Aβ peptide.

Amyloidogenic plaques and vascular amyloid angiopathy also characterize the brains of patients with Trisomy 21 (Down Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders.

Recently, Abeta has been reported to be implicated in the development of retinal ganglion cell (RGC) apoptosis in glaucoma, with evidence of caspase-3-mediated abnormal amyloid precursor protein processing, increased expression of Abeta in RGCs in experimental glaucoma and decreased vitreous Aβ levels (consistent with retinal Aβ deposition) in patients with glaucoma. Amyloid deposits have also been associated with macular degeneration in patients suffering from dry age-related macular degeneration (AMD) and in animal models of AMD.

WO 2010/021680, WO2011/106414 and WO 2010/105179 disclose spirocyclic acylguanidines with a spirocyclic scaffold as inhibitors of beta-secretase.

SUMMARY OF THE INVENTION

The present invention provides compounds that are BACE1 inhibitors and are useful as therapeutic agents in the treatment of a disease or disorder characterized by elevated β-amyloid deposits or β-amyloid levels in a patient. The disclosed BACE1 inhibitors are not only highly potent inhibitors of the BACE1 enzyme (assay 1) but also show:
(1) highly potent inhibitory activity in the cellular Abeta assay (assay 2),
(2) selectivity against the cardiac hERG channel in a cellular assay (assay 3), and
(3) a low propensity to cause phospholipidosis in a cellular phospholipidosis assay (assay 4), as well.

Thus, the present invention provides compounds which show a combination of high potency as BACE1 inhibitors, high selectivity against the cardiac hERG channel, and low phospholipidosis activity.

One embodiment of the invention is a compound represented by a structural formula selected from:

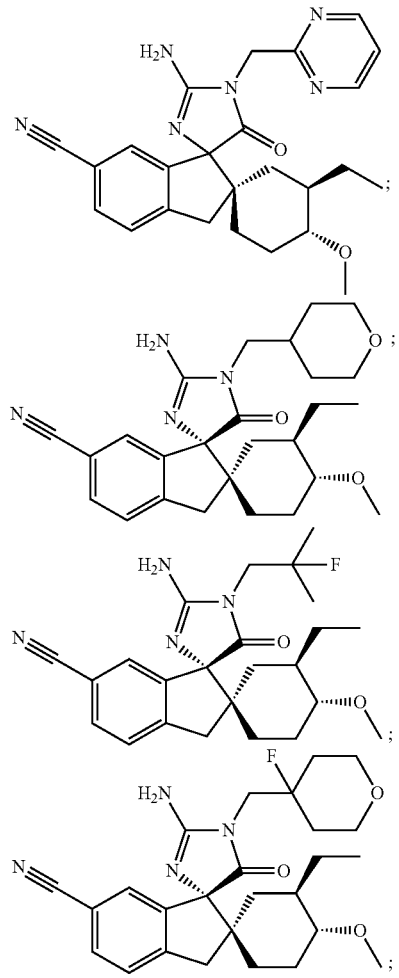

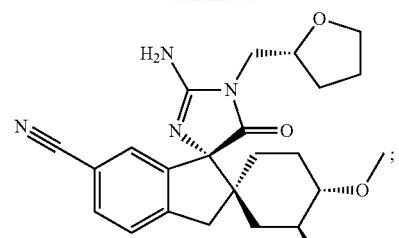
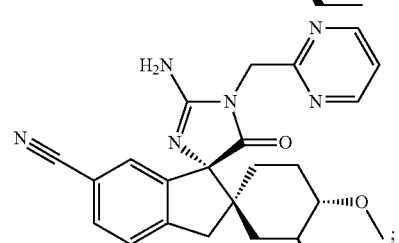
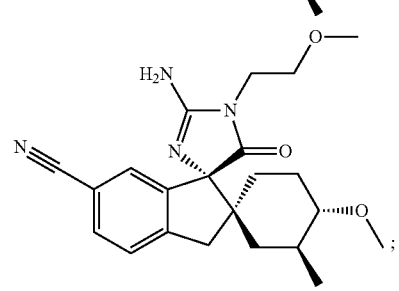
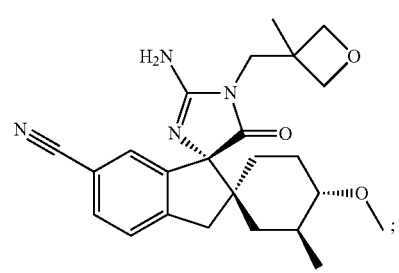
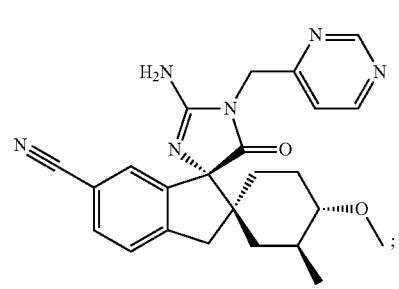
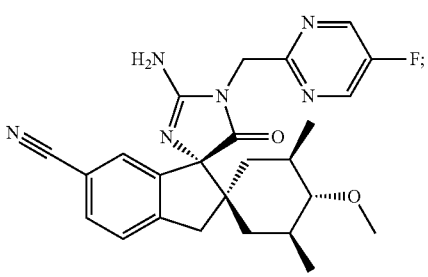
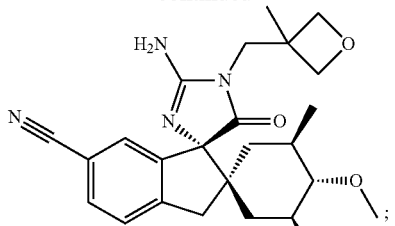
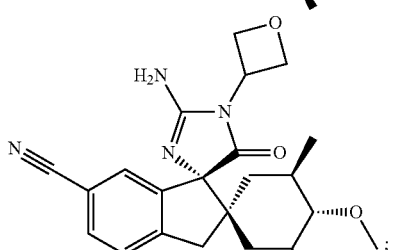
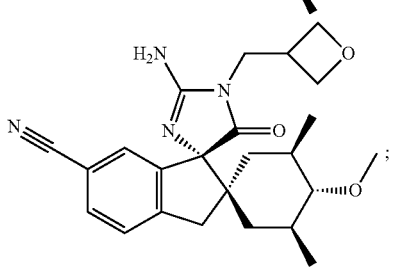
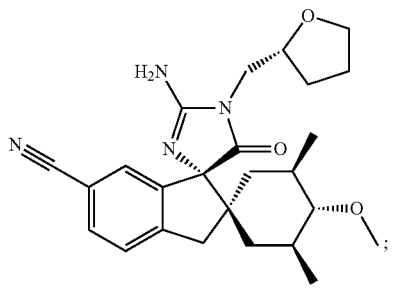
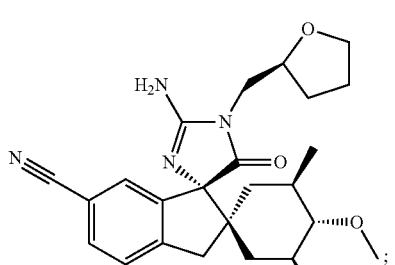
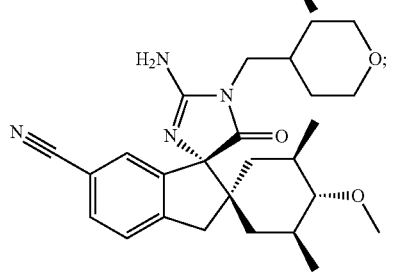

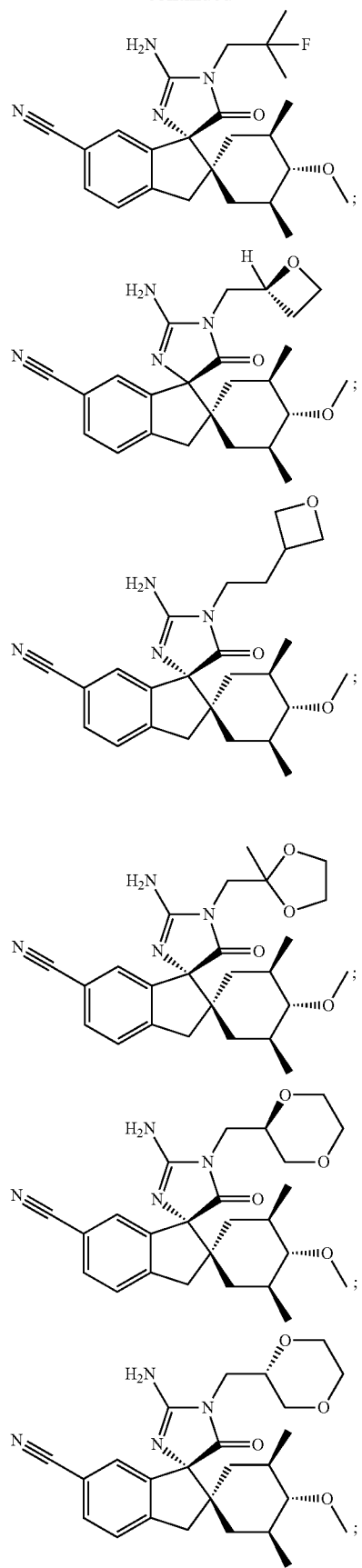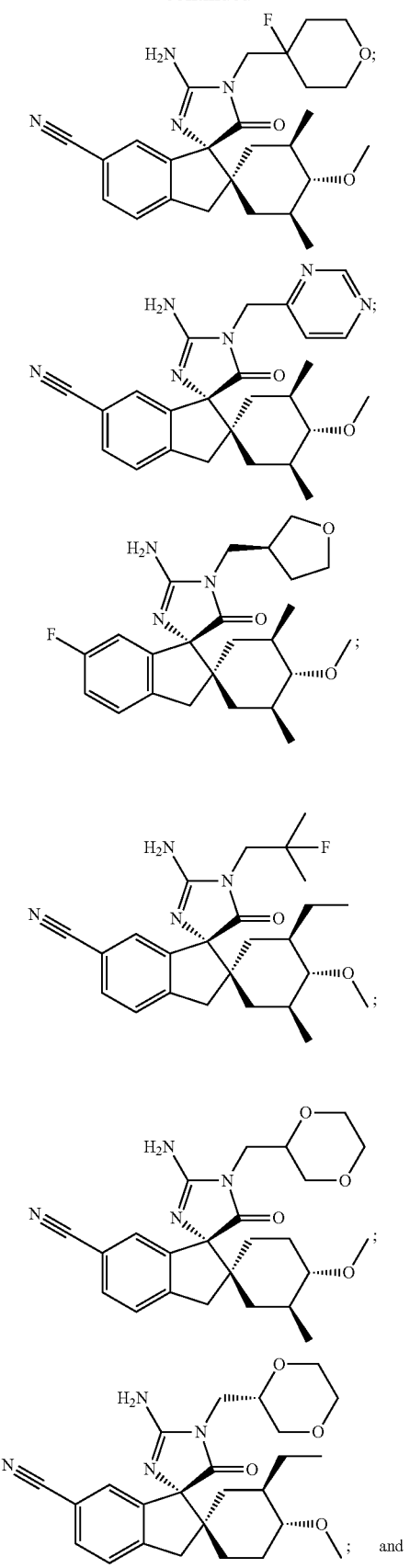

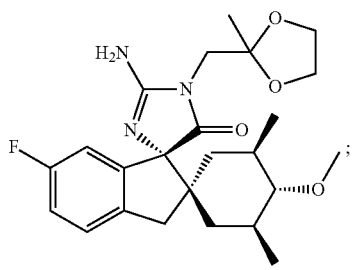

or a pharmaceutically acceptable salt of any of the foregoing compounds. The immediately foregoing compounds are referred to herein as "compounds of the present invention".

Another embodiment of the invention is a compound of the present invention or a pharmaceutically acceptable salt thereof for use as a medicament.

Another embodiment of the invention is a pharmaceutical composition comprising a compound of the present invention or a pharmaceutically acceptable salt thereof in admixture with a pharmaceutically acceptable adjuvant, diluent or carrier.

Another embodiment of the invention is a compound of the present invention or a pharmaceutically acceptable salt thereof for use in the treatment of a BACE1 mediated disorder or disease in a subject.

Another embodiment of the invention is the use of a compound of the present invention or a pharmaceutically acceptable salt thereof for the manufacture of a medicament for the treatment of a BACE1 mediated disorder in a subject.

Another embodiment of the invention is a method of treating a subject with a BACE1 mediated disease or disorder, comprising administering to the subject an effective amount of a compound of the present invention or a pharmaceutically acceptable salt thereof.

Yet another embodiment of the invention is an intermediate used in the preparation of a compound of the present invention. These intermediates are represented by a structural formula selected from:

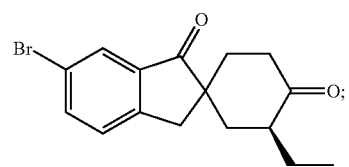

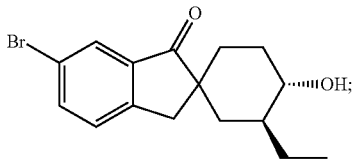

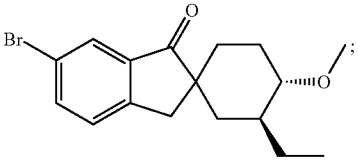

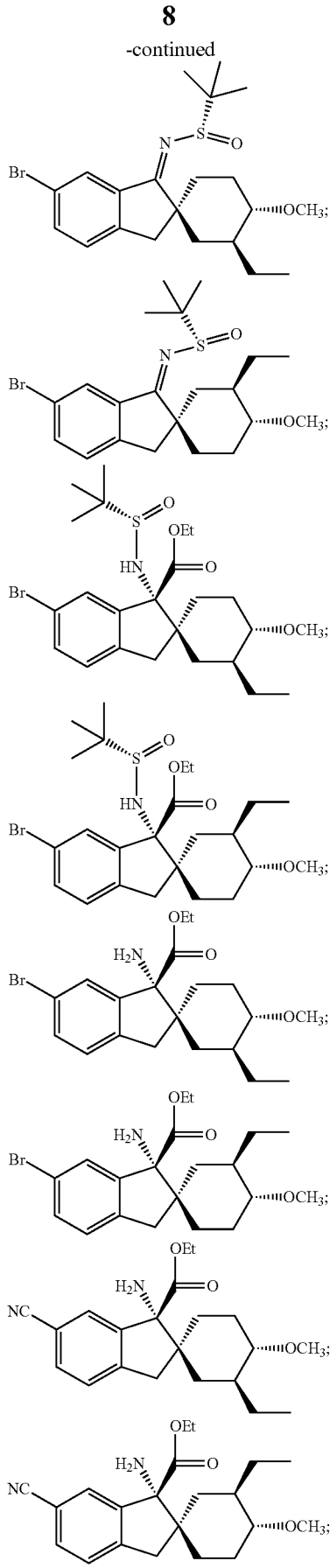

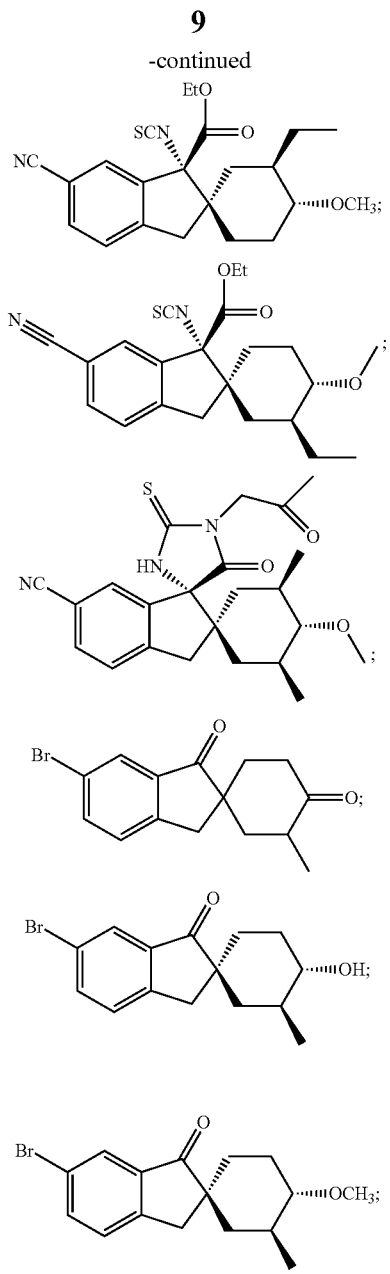
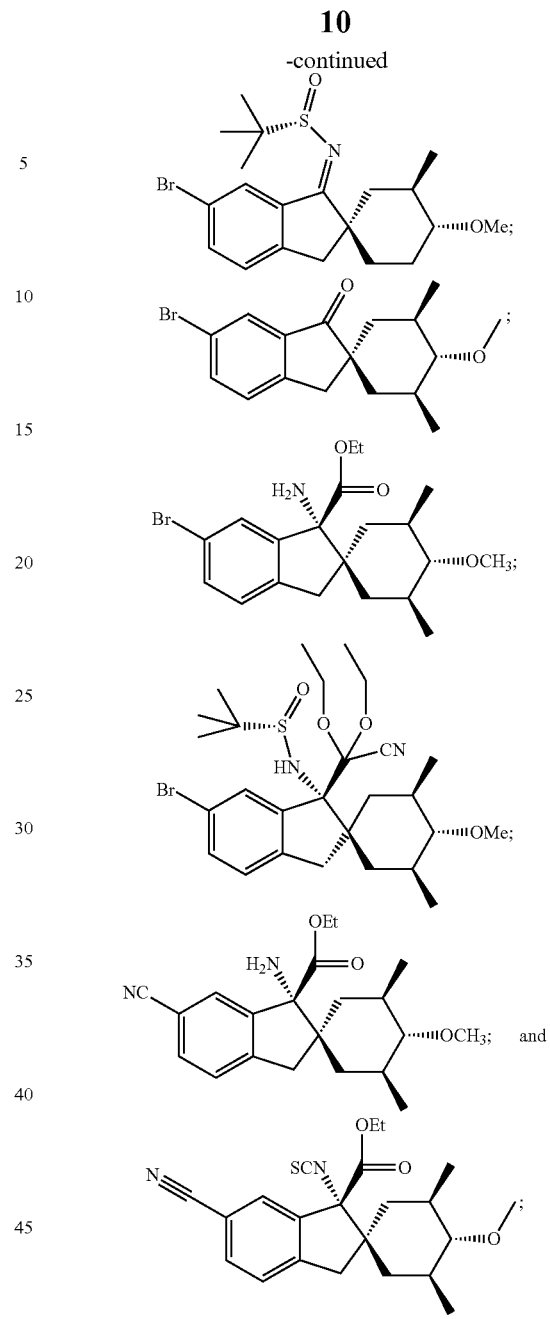

or a salt of any of the foregoing compounds.

DETAILED DESCRIPTION OF THE INVENTION

The compounds of the present invention exhibit potent activity against the BACE1 enzyme and Abeta formation together with the selectivity against the hERG channel and the low propensity to cause phospholipidosis. For example, the compounds of the present invention show a BACE1 inhibition with an $IC_{50}$<15 nM, a cellular Abeta production inhibition with an $IC_{50}$ of <2 nM, a hERG inhibition of <50% at 10 μM, and phospholipidosis with a First Effect Concentration (FEC) of >150 μM. These combined properties make the compounds of the present invention useful for the treatment of pathological states in humans, in particular, for the treatment of Alzheimer's disease as well as other disorders and diseases mediated by BACE1.

Inhibition of the hERG (human Ether-à-go-go-Related Gene) channel by xenobiotics and subsequent delayed cardiac repolarization is associated with an increased risk for a specific polymorphic ventricular tachyarrhythmia, torsade de pointes, as established by Sanguinetti et al. (1995, Cell, April 21, 81(2):299-307) and a large body of subsequent evidence. To avoid this risk early on, screening against hERG interaction in an in vitro system using heterologous expression of the hERG channel is common practice and an assay of this type is also an important part of later preclinical candidate profiling as recommended by the ICH guideline S7B (International Conference on Harmonization (2005): ICH Topic S 7 B The nonclinical Evaluation of the Potential for delayed Ventricular Repolarization; (QT Interval Prolongation) by Human Pharmaceuticals (ich.org/products/guidelines/safety/article/safety-guidelines). As such, low hERG channel inhibition, such as that shown by the compounds of the present invention, is highly desirable for therapeutics.

Phospholipidosis is a lipid storage disorder in which excess phospholipids accumulate within cells. Drug-induced phospholipidosis is an undesirable drug reaction. Therefore, in order to avoid detrimental side effects, compounds with low phospholipidosis potential are preferred for human therapeutic use.

Data provided in Table 1 below show that compounds of the present invention have this combination of potent BACE1 cellular activity, selectivity against cardiac hERG and low propensity to cause phospholipidosis. In addition, Table 2 provides data showing that certain compounds of the present invention have significantly lower $IC_{50}$ inhibitory values in a BACE1 enzymatic assay and also in a cellular Abeta assay relative to certain comparator compounds.

Terms not specifically defined herein should be given the meanings that would be given to them by one of skill in the art in light of the disclosure and the context. As used in the specification, however, unless specified to the contrary, the following terms have the meaning indicated and the following conventions are adhered to.

When a compound of the present invention is depicted by name or structure without indicating all tautomeric forms, it is to be understood that the compound and its pharmaceutically acceptable salts shall encompass all tautomers.

When a compound of the present invention is depicted by name or structure without indicating the stereochemistry, it is to be understood that the compound and its pharmaceutically acceptable salts shall encompass all stereo, optical and geometrical isomers (e.g., enantiomers, diastereomers, E/Z isomers, etc.) and racemates thereof, as well as mixtures in different proportions of the separate enantiomers, mixtures of diastereomers, or mixtures of any of the foregoing forms.

When a stereo, optical or geometric isomer is depicted by name or structure, it is to be understood that the stereo, optical and/or geometric isomeric purity of the named or depicted stereo, optical or geometric isomer is at least 60%, 70%, 80%, 90%, 99% or 99.9% pure by weight. Stereo, optical and geometric isomeric purity is determined by dividing the weight of the named or depicted stereo, optical and geometric isomer in a mixture by the total weight of all stereo, optical and geometric isomers in the mixture.

When a compound of the present invention or its pharmaceutically acceptable salt is named or depicted by structure, it is to be understood that solvates, hydrates and the anhydrous form of the compound and solvates, hydrates and anhydrous form of its pharmaceutically acceptable salt are included in the invention. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water. "Anhydrous form" refers to compounds with no solvent or water or substantially no solvent or water incorporated into the crystal structure (e.g., less than 1:10, 1:20; 1:100; or 1:200 molar ratio of solvent or water to compound).

Salts

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine(2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine(2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like (see also Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of acids other than those mentioned above which for example are useful for purifying or isolating the compounds of the present invention (e.g., trifluoro acetate salts) also comprise a part of the invention.

Biological Data

BACE1 Assay (Assay 1)

The inhibitory activity of compounds was assessed by a fluorescence quench assay of BACE1 activity using commercially available substrate HiLyte Fluor™488-Glu-Val-Asn-Leu-Asp-Ala-Glu-Phe-Lys-(QXLT™ 520)-OH (SEQ ID NO:1) AnaSpec, San Jose, Calif.) and truncated human beta-secretase, BACE1 (amino acids 1-454) fused to a myc-his tag and secreted from HEK293/BACE$_{ect.}$ cells into OptiMEM™ (Invitrogen). The substrate was dissolved at 1 mg/ml in DMSO.

The assay was performed in the presence of OptiMEM (supernatant collected over 24 h and cleared from cellular debris by centrifugation) containing the ectodomain of BACE1, 25 μl water containing the desired 2-fold concentration of test compound and 2% DMSO, 1 μM substrate peptide, 20 mM NaOAc, pH 4.4, and 0.04% Triton-X100 in a total assay volume of 50 μl in a 384 well plate. In general, 25 μl of compound dilution were given to the plate followed by the addition of 10 μl of BACE1 containing OptiMEM™ diluted 1:10 in water with 0.2% Triton X-100. The reaction was started with the addition of 15 μl substrate in NaOAc buffer. The reaction was incubated at rt (dark) in an Envision® multilabel reader (Perkin Elmer) and the cleavage of the substrate was recorded as kinetic for 60 min at ex: 485 nm, em: 538 nm. Blank wells containing no enzyme were included on each plate.

The intensity of fluorescence was regressed against time in order to derive velocities of reaction in all 384 wells. These velocities were used for calculating percent control using an uninhibited control containing 1% DMSO as 100% and blank control performed in the absence of enzyme as 0%. $IC_{50}$ values were calculated by fitting percent control vs. test compound concentration using Assay Explorer.

H4-APPwt Cell-Based Assay (Assay 2)

Cellular potency of the compounds of the invention was assessed in an assay monitoring production of Abeta1-x peptides in the H4 neuroglioma cell line (ATCC, Cat. #HTB-148) stably expressing human APP, using an immunoassay such as AlphaLISA (PerkinElmer, Cat.# AL288). Tested compounds were dissolved in DMSO and pre-diluted in the culture medium (DMEM containing 10% FBS and 1% penicillin/streptomycin) to achieve twice the final concentration of the compounds in the assay. Equal volumes of the 2× solutions of the tested compounds and cell suspension were added to a 96-well culture plate, so that each well contained ~10,000 cells in a final volume of 200 μl. Final concentration of DMSO in the assay was 0.2%. The plates were incubated for 5 hrs at 37° C., 5% $CO_2$ to allow cells to attach to the bottom of the wells in the presence of the tested compounds. Then the media was removed and replaced with fresh media containing tested compounds at the same final concentration. The plates were incubated for 18 hrs at 37° C., 5% $CO_2$. Concentrations of Ab1-x were determined using AlphaLISA immunoassay (PerkinElmer, Cat.# AL288) following manufacturer's protocol. Concentrations of Abeta1-x in the wells containing either DMSO or 10 μM beta-secretase inhibitor (BACE inhibitor IV, EMD Bioscience, Cat. #565788) were used as uninhibited and background controls, correspondingly, for calculating percent inhibition values for each well with the tested compounds. These percent inhibition values were regressed against compound concentrations using four-parameter curve fitting, and the IC50 values (concentration of a compound at which 50% of the inhibitory effect was observed) was calculated as the compound concentration corresponding to the inflection point on the curve.

hERG-Channel Assay (Assay 3)

Cells:

HEK (human embryonic kidney) 293 cells were stably transfected with hERG cDNA.

Pipettes and Solutions:

Cells were superfused with a bath solution containing (mM): NaCl (137), KCl (4.0), $MgCl_2$ (1.0), $CaCl_2$ (1.8), Glucose (10), HEPES (10), pH 7.4 with NaOH. Patch pipettes were made from borosilicate glass tubing using a horizontal puller and filled with pipette solution containing (mM): K-aspartate (130), $MgCl_2$ (5.0), EGTA (5.0), $K_2ATP$ (4.0), HEPES (10.0), pH 7.2 with KOH. Resistance of the microelectrodes was in the range between 2 and 5 MΩ.

Stimulation and Recording:

Membrane currents were recorded using an EPC-10 patch clamp amplifier and PatchMaster software. hERG-mediated membrane currents were recorded at 35° C., using the whole-cell configuration of the patch-clamp technique. Transfected HEK293 cells were clamped at a holding potential of −60 mV and hERG-mediated inactivating tail currents were elicited using a pulse pattern with fixed amplitudes (activation/inactivation: 40 mV for 2000 ms; recovery: −120 mV for 2 ms; ramp to 40 mV in 2 ms; inactivating tail current: 40 mV for 50 ms) repeated at 15 s intervals. During each inter-pulse interval 4 pulses scaled down by a factor of 0.2 were recorded for a P/n leak subtraction procedure. $R_s$ compensation was employed up to a level that safely allowed recording devoid of ringing.

Compound Preparation and Application:

The different concentrations of the test compound were applied sequentially on each of the different cells investigated. A steady state level of baseline current was measured for at least 6 sweeps prior to the application of the first test compound concentration.

The test compound was dissolved in DMSO to yield a master stock solution which was diluted further in DMSO to stock solutions needed for the lower concentrations. Final dilutions in extracellular buffer were prepared freshly from these stocks by a 1:1000 dilution step each before starting the experiments.

Data Analysis:

Peak current amplitudes were measured 3 ms after the ramp to +40 mV. For baseline and each concentration the peak currents of the three last sweeps before application of the next concentration were averaged. Residual currents ($I/I_0$) were calculated for each cell as the fraction of actual average peak current and average baseline peak current. Results are presented as percent (%) inhibition $(1−I/I_0)*100\%$ at 10 μM.

In Vitro Phospholipidosis Assay (Assay 4)

The phospholipidogenic potential of test compounds was assayed using the human hematopoetic U937 cell line. The test principle was to analyze the phospholipid content by staining the cells with the fluorescent dye Nile red.

U937 cells were seeded into cell culture plates at $0.5×10^6$ cells/mL in RPMI medium containing 10% FBS, 1% DMSO, and 0.005% gentamicin. The cells were then cultivated with or without different concentrations of test compounds for 48 h under standard culture conditions.

For harvesting the cells were centrifuged at 130×g for 4 min and washed once with PBS. Then 2×0.5 mL cell suspension was prepared for non-fixed cell measurement (0.5 mL for propidium iodide (PI) viability measurement and 0.5 mL for Nile red measurement).

The remaining cells were fixed with 3.7% formaldehyde for 30 min. After a further centrifugation step cells were resuspended with 1.3 mL Nile red working solution (1 µg/mL) and incubated for 5 min at rt. The cell suspension was then washed twice with 3 mL PBS and centrifuged with 130×g for 4 min. The supernatant was discarded and the cells were resuspended with 0.5 mL PBS and kept for flow cytometry measurement. For Nile red staining of the 0.5 mL non-fixed cell samples, 50 µL of a ready to use Nile red solution (10 µg/mL) were added per sample. Samples were kept on ice for 5 min. Thereafter, they were washed once with 4 mL PBS (4° C., 250×g for 8 min) and finally resuspended in 400 µL PBS and kept for flow cytometry measurement.

For the viability measurement, 12.5 µL of the ready to use PI solution (10 µg/mL) were added to the 0.5 mL non-fixed cell suspension. After 15 min of incubation on ice, the samples were measured by flow cytometry using a Coulter Epics XL/MCL flow cytometer.

The viability of the cells of each sample was determined by flow cytometry measurement of the PI content at channel 2 (568-590 nm). Cut-off gates for the fluorescence-dependent differentiation between live and dead cells were defined based on the analysis of cell culture medium control samples.

Only samples with a cell viability of >=90% relative to control samples were analyzed for phospholipidosis. For that, each Nile red sample (non-fixed and fixed samples) was measured by flow cytometry at channel 1 (504-541 nm) and channel 4 (660-680 nm).

For each channel, relative Nile red fluorescence intensity of a test sample was calculated compared to control samples and expressed as percentage of control fluorescence intensity. The assessment of the phospholipidogenic potential and the first effect concentration (FEC) of a test compound was done manually based on the fluorescence intensities at both wavelengths for the fixed cells as well as for the non-fixed cells.

Rat Brain Aβ Lowering Assay (Assay 5)

The in vivo efficacy of compounds of the invention was demonstrated in a rat brain Aβ lowering (reduction) assay, and the data are presented in Table 3. Male Sprague-Dawley rats, 5 to 6 weeks of age, were used to demonstrate the ability of compounds of the invention to reduce brain amyloid peptides Aβ1-x. Compounds were administered via oral gavage in 1% Polysorbate-80 and 0.5% Natrosol®, at the single dosages indicated in Table 3. The animals were sacrificed 3 hrs after dosing, and brains were excised, dissected into cerebellum and left and right cerebra and flash-frozen in liquid nitrogen.

The cerebrum was homogenized (5 volumes per weight) in 20 mM Tris-HCL, pH 8.5, 0.2% Triton-X100 supplemented with protease inhibitors (complete, Roche Applied Science) at 4° C. using a glass Dounce homogenizer. The homogenate was centrifuged at 120,000×g for 60 min at 4° C., and the supernatant was collected and analyzed for Ab1-x using immunoassay with chemiluminescent detection (Meso-Scale Discovery, Rockville, Md. (MSD)).

Streptavidin 96-well plates (MSD) were pre-blocked with 5% Blocker A solution (MSD) for 1 hr at rt on an orbital shaker and washed 4 times with phosphate buffered saline (PBS). The wells were pre-coated with 20 ng/well of biotinylated antibody SIG-39155 (Clone M3.2, specific for amino acids 10-15 of the rodent Aβ) for 1 hr at rt and washed 4 times with PBS. For Aβ1-x analysis, 25 µl of either the cleared brain lysates or Aβ1-40 standards (8-500 pg/ml, with 2× increment) were incubated for 1 hr at rt with constant shaking. The wells were washed 4 times with PBS, and 25 µl of the detection antibody (Sulfo-TAG labeled anti-Aβ40 antibody supplied by MSD) was added and incubated for 1 hr at rt. After 4 washes with PBS, 150 µl of the chemiluminescence detection reagent (Read Buffer T, MSD) was added, and the plate was read on an MSD Sector Imager 6000 instrument. The calibration curve was fit into a non-linear four-parameter regression model, and the Aβ1-x concentrations were calculated for each well containing the cleared brain lysates. The percent of Aβ lowering was calculated based on the difference with the average Aβ concentration obtained for the brains from the animals treated with vehicle alone.

Table 1 shows the following properties of the compounds of the present invention: BACE1 inhibitory potency as measured in assay 1, cellular inhibitory potency as measured in assay 2, hERG inhibition as measured in assay 3, and first effect concentration (FEC) of phospholipidosis as measured in assay 4.

TABLE 1

Biological properties of compounds of the present invention

| Example | BACE1 IC$_{50}$ nM (assay 1) | H4-APPwt cell IC$_{50}$ nM (assay 2) | hERG % inhibition @ 10 µM (assay 3) | Phospholipidosis FEC IC$_{50}$ µM (assay 4) |
|---|---|---|---|---|
| 1 | 11 | 0.76 | 8 | 200 |
| 2 | 8 | 0.29 | 22 | 200 |
| 3 | 10 | 0.57 | 9 | >200 |
| 4 | 5 | 0.28 | 0 | >400 |
| 5 | 8 | 0.90 | 7 | 200 |
| 6 | 11 | 1.24 | 35 | 200 |
| 7 | 2 | 1.42 | 8 | 400 |
| 8 | 5 | 0.49 | 16 | >200 |
| 9 | 9 | 1.90 | 16 | 400 |
| 10 | 9 | 1.12 | 38 | 200 |
| 11 | 4 | 0.35 | 6 | >400 |
| 12 | 3 | 1.10 | 11 | 400 |
| 13 | 9 | 0.92 | 18 | 200 |
| 14 | 5 | 0.12 | 20 | >200 |
| 15 | 11 | 0.11 | 11 | 200 |
| 16 | 11 | 0.20 | 6 | 200 |
| 17 | 14 | 0.89 | 12 | >200 |
| 18 | 9 | 1.02 | 17 | >400 |
| 19 | 6 | 0.40 | 8 | 400 |
| 20 | — | 0.28 | 8 | >400 |
| 21 | 5 | 0.48 | 24 | 400 |
| 22 | 8 | 0.26 | 9 | >400 |
| 23 | 12 | 0.18 | 16 | >200 |
| 24 | 5 | 0.65 | 23 | 200 |
| 25 |  | 0.99 | 10 | 200 |
| 26 | 9 | 0.20 | 8 | >200 |
| 27 | 6 | 0.95 | 19 | >200 |
| 28 |  | 0.5 | 9 | 400 |
| 29 |  | 0.3 | 7 | 200 |

Table 2 provides data showing that certain compounds of the present invention have significantly lower IC$_{50}$ inhibitory values in the BACE1 enzymatic assay (Assay 1) and in the cellular Abeta assay (Assay 2) relative to certain comparator compounds described in WO 2010/105179.

TABLE 2

| Compounds of the present invention | | Comparison examples: |
|---|---|---|
| 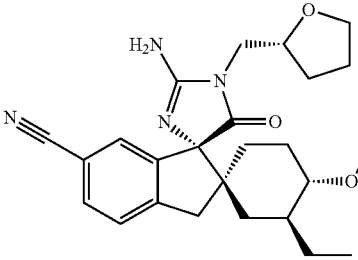<br>Example 5 | 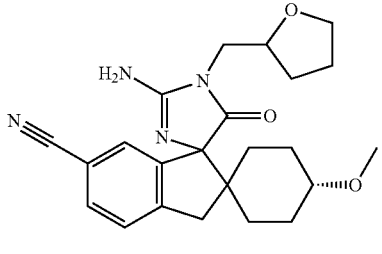<br>Example 14 | 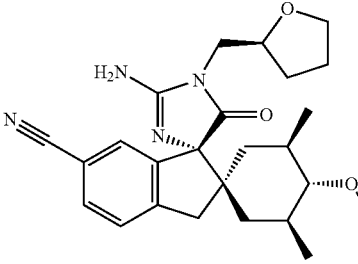<br>BACE IC$_{50}$ (assay 1) 35 nM<br>H4-Cell assay (assay 2) 7.0 nM<br>hERG (assay 3) 16% at 10 μM |
| 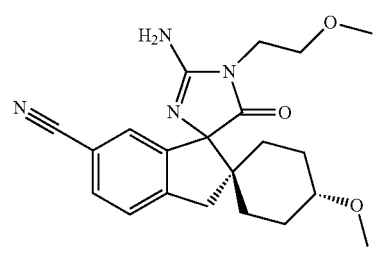<br>Example 15 | | |
| 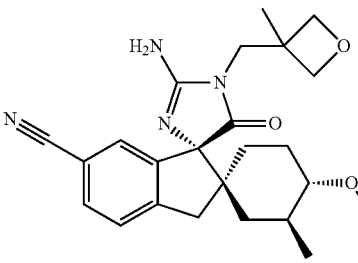<br>Example 7 | | 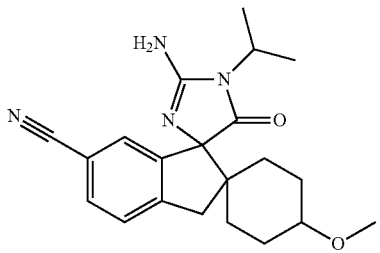 [SMILES: COC1CCC2(CC1)Cc1ccc(C#N)cc1C21N=C(N)N(C(C)C)C1=O]<br>BACE IC$_{50}$ (assay 1) 49 nM<br>H4-Cell assay (assay 2) 16 nM |
| 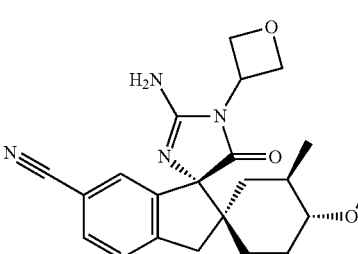<br>Example 8 | 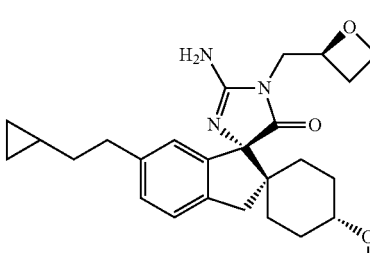<br>Example 11 | <br>BACE IC$_{50}$ (assay 1) 107 nM<br>H4-Cell Assay (assay 2) 16 nM |
| 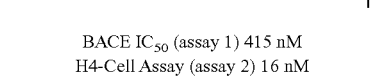<br>Example 12 | <br>Example 18 | <br>BACE IC$_{50}$ (assay 1) 415 nM<br>H4-Cell Assay (assay 2) 16 nM |

The ability of compounds of the invention to reduce brain Aβ was demonstrated in rats, as described in Assay 5, and the in vivo efficacy data are presented in Table 3.

TABLE 3

| Example | Dose (mg/kg) | % Aβ Reduction |
|---------|--------------|----------------|
| 2       | 30           | 42             |
| 4       | 25           | 75             |
| 6       | 50           | 60             |
| 8       | 25           | 37             |
| 9       | 25           | 37             |
| 12      | 25           | 39             |
| 13      | 30           | 47             |
| 14      | 25           | 67             |
| 15      | 25           | 62             |
| 17      | 25           | 70             |
| 18      | 25           | 56             |
| 20      | 25           | 73             |
| 21      | 50           | 59             |
| 22      | 12.5         | 45             |
| 23      | 25           | 68             |
| 26      | 25           | 71             |
| 28      | 12.5         | 30             |
| 29      | 25           | 78             |

Method of Treatment

The present invention is directed to compounds which are useful in the treatment of disorders or diseases characterized by elevated β-amyloid deposits or β-amyloid levels in a subject wherein the inhibition of the activity of the β-secretase enzyme (BACE1) is of therapeutic benefit, including but not limited to the treatment, amelioration or prevention of neurodegenerative disorders, disorders characterized by cognitive decline, cognitive impairment, dementia, and diseases characterized by production of β-amyloid deposits or neurofibrillary tangles.

Compounds of the present invention are useful for treatment of Alzheimer's disease, Trisomy 21 (Down Syndrome), Hereditary Cerebral Hemorrhage with Amyloidosis of the Dutch-type (HCHWA-D), senile dementia, cerebral amyloid angiopathy, degenerative dementia, dementias of mixed vascular and degenerative origin, dementia associated with Parkinson's disease, dementia associated with progressive supranuclear palsy, dementia associated with cortical basal degeneration, diffuse Lewy body type of Alzheimer's disease, dry age related macular degeneration (AMD), and glaucoma. The "dry" form of AMD, also known as "central geographic atrophy", results from atrophy to the retinal pigment epithelial layer below the neurosensory retina, which causes vision loss through loss of photoreceptors (rods and cones) in the central part of the eye. No medical or surgical treatment is currently available for this condition. Treatments available so far (e.g., suggested by the National Eye Institute) include the use of vitamin supplements with high doses of antioxidants, lutein and zeaxanthin, which may slow the progression of dry macular degeneration. Glaucoma is a disease where fluid pressure inside the eye increases, causing irreversible damage to the optic nerve and loss of vision. Abeta colocalizes with apoptotic retinal ganglion cells in experimental glaucoma and induces significant retinal ganglion cell apoptosis in a dose- and time-dependent manner.

Accordingly, the present invention relates to a compound or a pharmaceutically acceptable salt thereof for use as a medicament.

Furthermore, the present invention relates to the use of a compound in the treatment of a disease and/or condition wherein the inhibition of the activity of the β-secretase enzyme (BACE1) is of therapeutic benefit. Furthermore, the present invention relates to the use of a compound in the treatment of neurodegenerative disorders, disorders characterized by cognitive decline, cognitive impairment, dementia, and diseases characterized by production of β-amyloid deposits or neurofibrillary tangles.

Therefore, the present invention relates to the use of a compound of the present invention in the treatment of Alzheimer's disease, Trisomy 21 (Down Syndrome), Hereditary Cerebral Hemorrhage with Amyloidosis of the Dutch-type (HCHWA-D), senile dementia, cerebral amyloid angiopathy, degenerative dementia, dementias of mixed vascular and degenerative origin, dementia associated with Parkinson's disease, dementia associated with progressive supranuclear palsy, dementia associated with cortical basal degeneration, diffuse Lewy body type of Alzheimer's disease, dry AMD, and glaucoma.

The present invention also provides a method for the treatment of a disorder related to or associated with excessive BACE1 activity in a patient in need thereof which comprises administering to said patient an effective amount of a disclosed compound or a pharmaceutically acceptable salt thereof. The present invention also provides methods for inhibiting the activity of BACE1 in a subject in need thereof, comprising administering to a subject and/or contacting a receptor thereof with an effective amount of at least one disclosed compound or a pharmaceutically acceptable salt thereof. The present invention also provides methods of ameliorating β-amyloid deposits in a subject in need thereof, comprising administering to said subject an effective amount of at least one disclosed compound or a pharmaceutically acceptable salt thereof. The invention includes a therapeutic method for treating or ameliorating a BACE1 mediated disorder in a subject in need thereof comprising administering to a subject in need thereof an effective amount of a compound of the invention described herein, or pharmaceutically acceptable salts thereof or composition thereof.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be prophylactic (i.e., reducing the likelihood of developing the disorder or disease) or therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The dose range of the compounds according to the present invention applicable per day is usually from 0.1 to 3000 mg, preferably from 1 to 2000 mg, more preferably from 10 to 1000 mg, most preferably, 50 or 500 mg. Each dosage unit may conveniently contain from 0.1 to 1000 mg, preferably 25 to 250 mg.

The actual pharmaceutically effective amount or therapeutic dosage will of course depend on factors known by those skilled in the art such as age and weight of the patient, route of administration and severity of disease. In any case, the combination will be administered at dosages and in a manner which allows a pharmaceutically effective amount to be delivered based upon patient's unique condition.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives and powders, etc. The content of the pharmaceutically active compound(s) should be in the range from 0.1 to 95 wt.-%, preferably 5 to 90 wt.-% of the composition as a whole.

Suitable tablets may be obtained, for example, by mixing one or more compounds of the invention with known excipients, for example inert diluents, carriers, disintegrants, adjuvants, surfactants, binders and/or lubricants. The tablets may also consist of several layers.

Combination Therapy

In one embodiment, the present invention includes combination therapy for treating or ameliorating a disease or a disorder described herein. The combination therapy comprises administering a combination of at least one compound of the present invention with one or more agent selected from the group of, for example, gamma-secretase inhibitors or modulators; amyloid aggregation inhibitors blocking the formation of Abeta oligomers or Abeta fibrils (e.g., ELND-005); directly or indirectly acting neuroprotective and/or disease-modifying substances; anti-oxidants (e.g., vitamin E or ginkolide); anti-inflammatory substances (e.g., Cox inhibitors, NSAIDs additionally or exclusively having Abeta lowering properties); HMG-CoA reductase inhibitors (statins); acetylcholinesterase inhibitors (e.g., donepezil, rivastigmine, tacrine, galantamine; tacrine); NMDA receptor antagonists (e.g., memantine); AMPA receptor agonists; AMPA receptor positive modulators, AMPAkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocyclin or rifampicin); PDE2, PDE4, PDE5, PDE9, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, antidepressants, such as citalopram, fluoxetine, paroxetine, sertraline and trazodone; anxiolytics, such as lorazepam and oxazepam; antiphychotics, such as aripiprazole, clozapine, haloperidol, olanzapine, quetiapine, risperidone and ziprasidone, and other substances that modulate receptors or enzymes in a manner such that the efficacy and/or safety of the compounds according to the invention is increased and/or unwanted side effects are reduced. The compounds according to the invention may also be used in combination with immunotherapies (e.g., active immunisation with Abeta or parts thereof or passive immunisation with humanised anti-Abeta antibodies or nanobodies) for the treatment of the above-mentioned diseases and conditions.

Combination therapy includes co-administration of the compound of the invention with one or more other agent, sequential administration of the compound and one or more other agent, administration of a composition containing a compound and one or more other agent, or simultaneous administration of separate compositions containing the compound and one or more other agent.

EXPERIMENTAL SECTION

Methods of Preparation of Compounds

Compounds of the invention can be prepared employing conventional methods that utilize readily available reagents and starting materials. The reagents used in the preparation of the compounds of this invention can be either commercially obtained or can be prepared by standard procedures described in the literature. Microwave reactions were carried out in CEM reactor using discovery SP system.

Where NMR data are presented, spectra were obtained in Varian –400 (400 MHz) and are reported as ppm downfield from tetramethylsilane with number of proton, multiplicities and coupling constants indicated parenthetically along with reference to deuterated solvent. Compounds were purified by basic preparative HPLC method as described below.

Method 1:

Mobile phase A: water with 0.05% ammonia solution;
Mobile phase B: ACN; Flow rate: 25 mL/min;
Detection: UV 220 nm/254 nm; Column: Phenomenex
Gemini C18 250 * 30 mm * 5 um
Column temperature: 30° C.

| Time in min | % A | % B |
|---|---|---|
| 0.0 | 68 | 32 |
| 12.00 | 38 | 62 |
| 12.20 | 0 | 100 |
| 13.5 | 0 | 100 |
| 13.7 | 90 | 10 |

Method 2:

Mobile phase A: water with 0.05% ammonia solution;
Mobile phase B: ACN; Flow rate: 25 mL/min;
Detection: UV 220 nm/254 nm; Column: Durashell
C18 250 * 30 mm * 5 um; Column temperature: 30° C.

| Time in min | % A | % B |
|---|---|---|
| 0.0 | 67 | 33 |
| 12.00 | 47 | 53 |
| 12.20 | 0 | 100 |
| 13.5 | 0 | 100 |
| 13.7 | 90 | 10 |

LC-MS data were obtained by utilizing the following chromatographic condition:

HPLC System: Waters ACQUITY; Column: Waters
ACQUITY CSH ™ C18 1.7 µM
Guard column: Waters Assy. Frit, 0.2 µM, 2.1 mm;
Column tem: 40° C.
Mobile Phase: A: TFA:Water (1:1000, v:v) Mobile phase B:
TFA:ACN (1:1000, v:v); Flow Rate: 0.65 mL/min;
Injection Volume: 2 µL; Acquisition time: approximately 1.5 min.
Gradient Program:

| Time (min) | B % |
|---|---|
| 0 | 10 |
| 0.8 | 90 |
| 1.20 | 90 |
| 1.21 | 10 |

Mass Spectrometer Parameters

Mass Spectrometer Waters SQD; Ionization: Positive Electrospray Ionization (ESI); Mode Scan (100-1400 m/z in every 0.2 second); ES Capillary Voltage: 3.5 kv; ES Cone Voltage: 25 v Source Temperature: 120° C.; Disolvation Temperature: 500° C.; Desolvation Gas Flow: Nitrogen Setting 650 (L/h); Cone Gas Flow: Nitrogen Setting 50 (L/h)

For Example 10, step 2, and the alternative synthesis of intermediate 38, step 1 and 2, the following chromatographic conditions and instrumentation were used:

LC-MS data were obtained by utilizing the following chromatographic condition:

| HPLC System: | Agilent 1100 Series |
| --- | --- |
| Column: | Zorax Eclipse XDB-C8, 2.1 × 50 mm |
| Column tem: | 35° C. |
| Mobile Phase: | A: Formic Acid:Water (1:1000, v:v) |
| | B: Formic Acid:ACN (1:1000, v:v) |

| Gradient Program: | |
| --- | --- |
| Time (min) | B % |
| 0 | 5 |
| 3 | 95 |
| 4.5 | 95 |
| 5.0 | 5 |

| Flow Rate: | 0.60 mL/min |
| --- | --- |
| Injection Volume: | 2 μL |
| Retention Times: | Approximately 1-4 min |
| Acquisition time: | approximately 5 min |

Mass Spectrometer Parameters

| Mass Spectrometer: Agilent 77 | |
| --- | --- |
| Ionization | Positive Electrospray Ionization (ESI) |
| Mode | Scan (100-800 m/z in every 0.2 second) |
| ES Capillary Voltage: | 3.5 kv |
| ES Cone Voltage: | 25 v |
| Source Temperature | 120° C. |
| Disolvation Temperature: | 500° C. |
| Desolvation Gas Flow: | Nitrogen Setting 650 (L/h) |
| Cone Gas Flow: | Nitrogen Setting 50 (L/h) |

For Example 27 the following chromatographic conditions and instrumentation were used:

| HPLC System: | Waters Alliance/DA- und MS-Detector |
| --- | --- |
| Column: | Waters XBridge C18, 4.6 × 30 mm, 3.5 μm |

| Gradient Program: | | | | |
| --- | --- | --- | --- | --- |
| Time [min] | % Sol [H2O, 0.1% TFA] | % Sol [Methanol] | Flow [ml/min] | Temp [° C.] |
| 0.0 | 95 | 5 | 4 | 60 |
| 1.6 | 0 | 100 | 4 | 60 |
| 1.85 | 0 | 100 | 4 | 60 |
| 1.9 | 95 | 5 | 4 | 60 |

SFC separation and characterization of compounds were carried out under the following method.

Method A:

Instrument: Thar SFC 80; Column: AD 250 mm*30 mm, 5 um; Mobile phase: A: Supercritical $CO_2$, B: IPA (0.05% DEA), A: B=80:20 at 60 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm.

Method B:

Instrument: SFC MG2; Column: OJ 250 mm*30 mm, 5 um; Mobile phase: A: Supercritical $CO_2$, B: MeOH (0.05% DEA), A:B=90:10 at 70 ml/min; Column Temp: 38° C.; Nozzle Pressure: 100 Bar Nozzle Temp: 60° C.; Evaporator Temp: 20° C.; Trimmer Temp: 25° C.; Wavelength: 220 nm The following techniques, solvents and reagents that may be referred by their following abbreviations:

| Abbreviation | Meaning |
| --- | --- |
| ACN | acetonitrile |
| Boc | tert-butoxy carbonyl or t-butoxy carbonyl |
| brine | saturated aqueous NaCl |
| DCM | methylene chloride |
| DIEA | diisopropyl ethyl amine |
| DMF | dimethyl formamide |
| DMSO | dimethyl sulfoxide |
| dppf | 1,1-bis(diphenylphosphino)ferrocene |
| EDCI | 1-(3-dimethylaminopropyl)-3-ethylcarbodiimide hydrochloride |
| EtI | ethyl iodide |
| Et | ethyl |
| $Et_2O$ | ethyl ether |
| EtOAc | ethyl acetate |
| EtOH | ethanol |
| HPLC | high performance liquid chromatography |
| LDA | lithium diisopropylamide |
| MeOH | methanol |
| MeI | methyl iodide |
| Me | methyl |
| $Me_2S$ | dimethyl sulfide |
| MsCl | methane sulfonyl chloride |
| NaOMe | sodium methoxide |
| $PdCl_2$dppf | [1,1-bis(diphenylphosphino)ferrocene]dichloropalladium-(II) |
| $Pd_2(dba)_3$ | tris(dibenzylideneacetone)dipalladium(0) |
| PE | petroleum ether |
| rt | room temperature |
| SFC | super critical fluid chromatography |
| t-BuOK | potassium tert butoxide |
| t-BuLi | tert butyl lithium |
| t-BuNH$_2$—BH3 | tert butylamin-borane complex |
| t-BuOOH | tert butyl peroxide |
| TFA | trifluoroacetic acid |
| TFAA | trifluoroacetic acid anhydride |
| THF | tetrahydrofuran |
| TLC | thin layer chromatography |
| Ti(OEt)$_4$ | titanium tetraethoxide |

Example 1

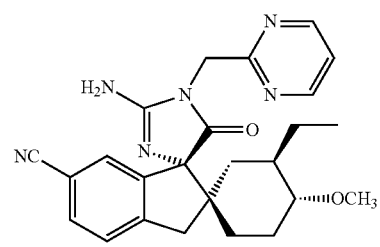

Step 1: Synthesis of Intermediate 3

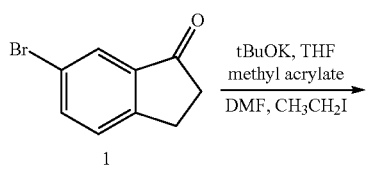

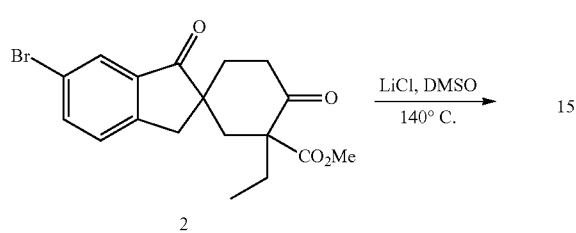

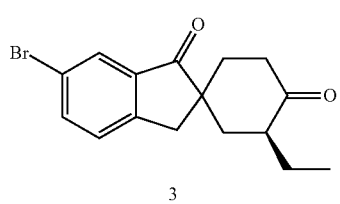

A mixture of compound 1 (50.0 g, 236 mmol) and methyl acrylate (42.0 g, 472 mmol) in anhydrous THF (900 mL) was pre-cooled at 0° C. and t-BuOK (31.8 g, 284 mmol, 1.1 eq) was added in equal portion over 30 min, the mixture was then warmed up to rt over 1 h and was stirred for 40 min at rt. DMF (200 mL) and EtI (74 g, 472 mmol) were added to this reaction mixture, and stirred at rt overnight. THF was removed under reduced pressure. The residue was diluted with H$_2$O (300 mL) and extracted with EtOAc, concentrated to afford the crude compound 2 (120.0 g). This product was used as is for next step.

A mixture of compound 2 (120.0 g, 310 mmol) and LiCl (130.0 g, 3100 mmol) in DMSO (900 mL) was refluxed overnight. The mixture was quenched with water (3 L) and extracted with EtOAc (3×400 mL). The separated organic phase was dried and concentrated under reduced pressure. The residue was purified by column chromatography on silica gel (petroleum ether:EtOAc=20:1) to give intermediate 3 (15 g, 20%).

$^1$H NMR: (CDCl$_3$): δ 7.91 (s, 1H), 7.74 (dd, J=8.0 Hz, 1H), 7.41 (d, J=8.0 Hz, 1H), 3.80 (s, 2H), 2.48-2.53 (m, 2H), 2.33-2.49 (m, 1H), 2.15-2.23 (m, 1H), 1.75-1.95 (m, 4H), 1.21-1.40 (m, 1H), 0.88 (t, J=8.0 Hz, 3H).

Step 2: Synthesis of Intermediate 5

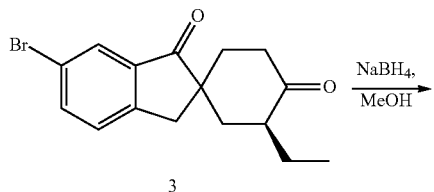

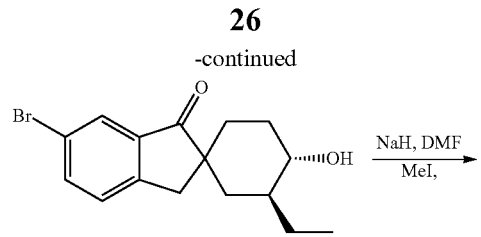

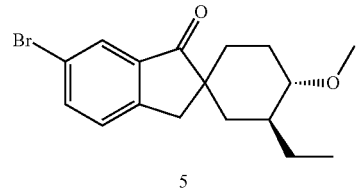

To a mixture of THF (20 mL) and MeOH (5 mL) at −78° C. was added intermediate 3 (6.0 g, 18.7 mmol), NaBH$_4$ (355 mg, 9.3 mmol) and CeCl$_3$.7H$_2$O (70 mg, 0.19 mmol). The mixture was stirred at −78° C. for 20 min, quenched with satd. NH$_4$Cl solution (30 mL), and extracted with EtOAc (400 mL×4). The EtOAc phases were combined and concentrated to afford a crude compound 4 (6.5 g, crude).

To a mixture of compound 4 (6.5 g, 20.0 mmol) and NaH (3.2 g, 80.0 mmol) in DMF (100 mL) at 0° C. was added MeI (11.4 g, 80.0 mmol). The mixture was stirred at rt overnight. The mixture was quenched with H$_2$O, extracted with EtOAc, concentrated to afford the crude product, which was purified by column on silica gel (eluent:petroleum ether:ethyl acetate from 20:1 to 15:1) to afford intermediate 5 (3.5 g, 56%).

LC-MS: t$_R$=1.315 min, MS (ESI) m/z 339.1 [M+H]$^+$.

$^1$H NMR: (CDCl$_3$): δ 7.88 (s, 1H), 7.69 (dd, J=8.4, 2.0 Hz, 1H), 7.31 (d, J=8.4 Hz, 1H), 3.39 (s, 3H), 2.97 (s, 2H), 2.88-2.94 (m, 1H), 2.21-2.26 (m, 1H), 1.81-1.87 (m, 1H), 1.70-1.78 (m, 1H), 1.40-1.59 (m, 4H), 1.12-1.39 (m, 2H), 0.88 (t, J=8.0 Hz, 3H).

Step 3: Synthesis of Intermediate 6A & 6B

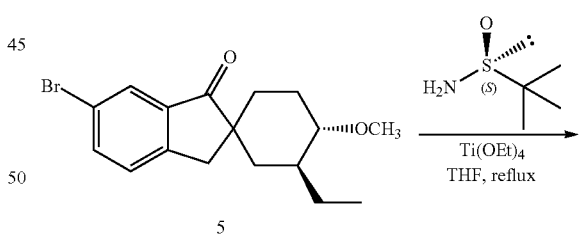

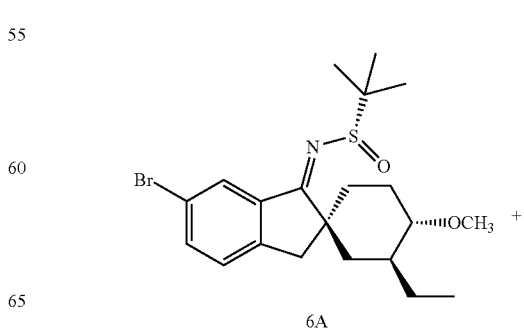

-continued

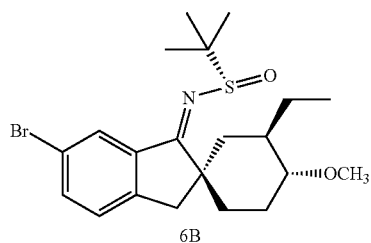
6B

The mixture of intermediate 5 (3.5 g, 10.4 mmol) and titanium (IV) ethoxide (23.7 g, 104 mmol) in dry THF (40 mL) was stirred at rt for 1 h. (S)—N-tert-butylsulfinamide (1.6 g, 11.6 mmol) was added and the resulting mixture was stirred at 80° C. under N₂ atmosphere overnight. The reaction mixture was then cooled and water (400 mL) was added and filtered. The aqueous layer was extracted with EtOAc (3×400 mL). The separated organic phases were combined and dried and concentrated under reduced pressure. The residue was purified by column chromatography on silica gel (petroleum ether:EtOAc=20:1) and compounds eluted in the following order to give intermediate 6A (1.5 g, 33%) and 6B (1.5 g, 33%).

Step 4: Synthesis of Intermediate 7B

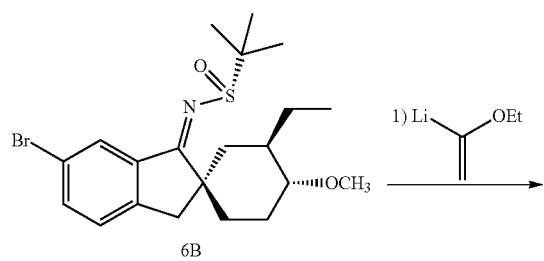

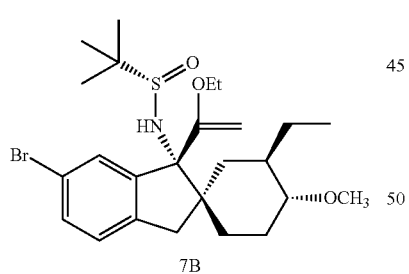
7B

To a mixture of ethoxy-ethene (1.3 g, 17.0 mmol) in anhydrous THF (20 mL) at −78° C. under a N₂ atmosphere, t-BuLi (13.0 mL, 17.0 mmol, 1.3 M in hexane) was added drop wise and stirred for 20 min. The resulting mixture was then stirred at 0° C. for an additional 45 min. To this mixture at −78° C., intermediate 6B (1.5 g, 3.4 mmol) was added drop wise in anhydrous THF (20 mL) and stirred for 2.5 h. The reaction was quenched with sat. NH₄Cl (50 mL) and extracted with EtOAc (3×300 mL). The organic phases were combined and concentrated to give the residue and which was purified by column on silica gel (petroleum ether:EtOAc=20:1) to afford intermediate 7B (1.2 g, 69%).

Step 5: Synthesis of Intermediate 8B

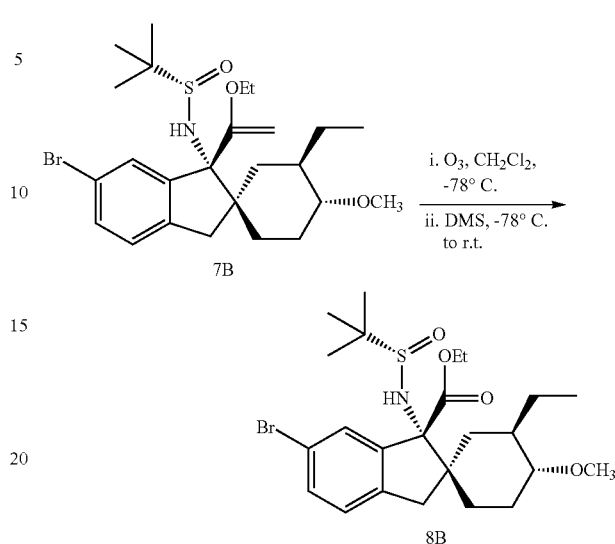

Intermediate 7B (1.2 g, 2.4 mmol) was added to DCM:MeOH (5:1, 20 mL), the mixture was chilled to −78° C. and ozone was bubbled through the mixture for 20 min. The mixture was then purged with N₂ and treated with Me₂S at −78° C. The reaction was then allowed to warm to rt and stirred for 3 h. The solvent was removed under vacuum, the residue was purified by preparative TLC (petroleum ether:EtOAc=3:1) to give compound 8B (860 mg, 70%).

LC-MS: $t_R$=1.351 min, MS (ESI) m/z 516.1 [M+H]⁺.

Step 6: Synthesis of Intermediate 9B

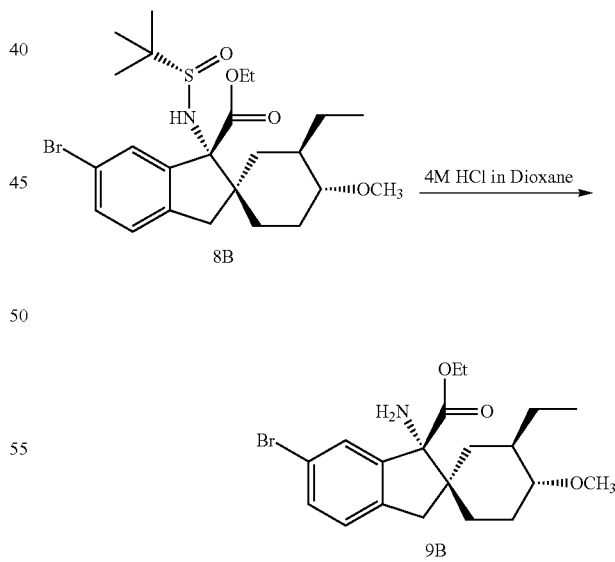

To compound 8B (860 mg, 1.7 mmol) in MeOH (10 mL) was added a 4 M HCl solution in dioxane (2 mL). The resulting mixture was stirred for 30 min. Solvent was removed under reduced pressure to afford crude compound 9B (800 mg). The residue was used for next step without further purification.

Step 7: Synthesis of Intermediate 10B

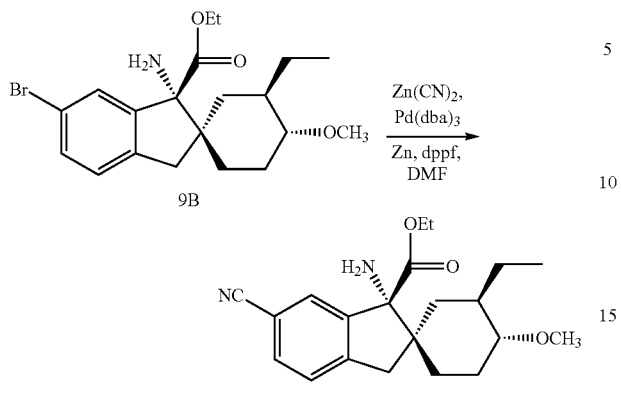

A suspension of intermediate 9B (500 mg, 1.9 mmol), Zn(CN)₂ (300 mg, 2.6 mmol), Pd₂(dba)₃ (150 mg, 0.16 mmol), dppf (160 mg, 0.32 mmol) and Zn dust (60 mg, 0.9 mmol) in DMF (15 mL) was heated under 120° C. for 3 h in CEM microwave reactor. The mixture was concentrated under vacuum and the residue was purified by column on silica gel (eluent: petroleum ether:EtOAc from 20:1 to 8:1) to afford compound 10B (150 mg, 40%).

Step 8: Synthesis of Intermediate 11B

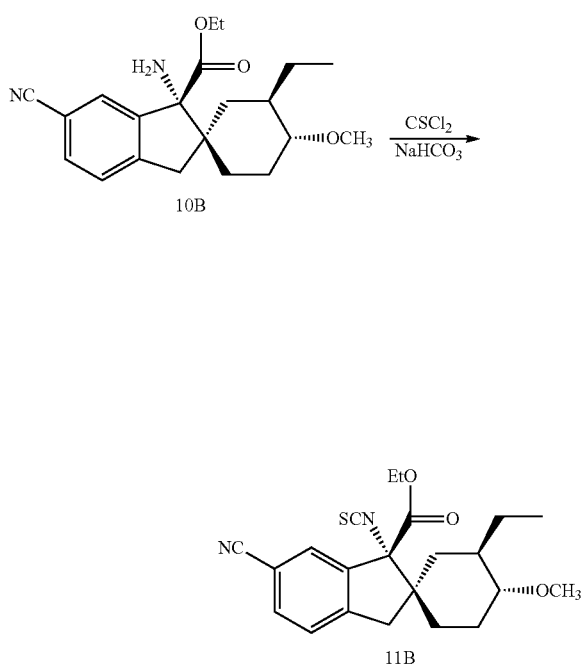

Intermediate 10B (150 mg, 0.42 mmol) was added to DCM (10 mL), H₂O (10 mL) and NaHCO₃ (350 mg, 4.2 mmol). To this mixture was added thiophosgene (100 mg, 0.84 mmol) under vigorous stirring, and stirred for 50 min at rt and extracted with DCM (3×40 mL). The organic layer was washed with brine (2×40 mL), dried and solvent was removed under reduced pressure to afford crude compound 11B (150 g, 93%), which was used for next step without further purification.

Step 9: Synthesis of Intermediate 12B

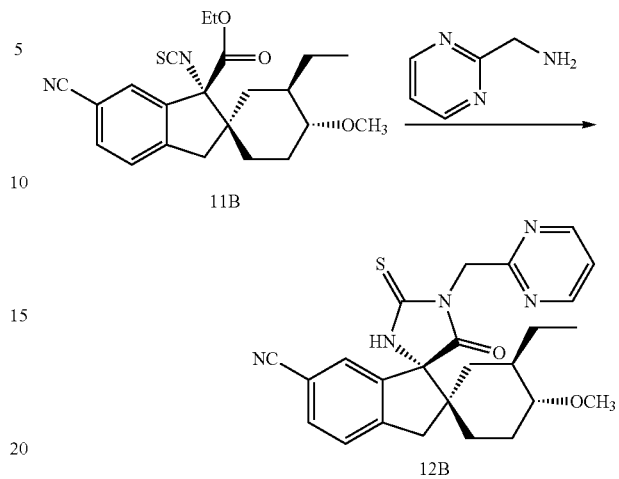

To a mixture of compound 11B (150 mg, 0.39 mmol) in THF (5 mL) was added 2-aminomethylpyrimidine (67 mg, 0.78 mmol) and TEA (395 mg, 3.90 mmol). The mixture was stirred overnight at rt. The reaction was diluted with water and extracted with EtOAc (30 mL). The residue was purified by column chromatography (petroleum ether: ethyl acetate=10:1) to afford 12B (100 mg, 70%).

LC-MS: $t_R$=1.204 min MS (ESI) m/z 462.2 [M+H]⁺.

Step 1: Synthesis of Example 1

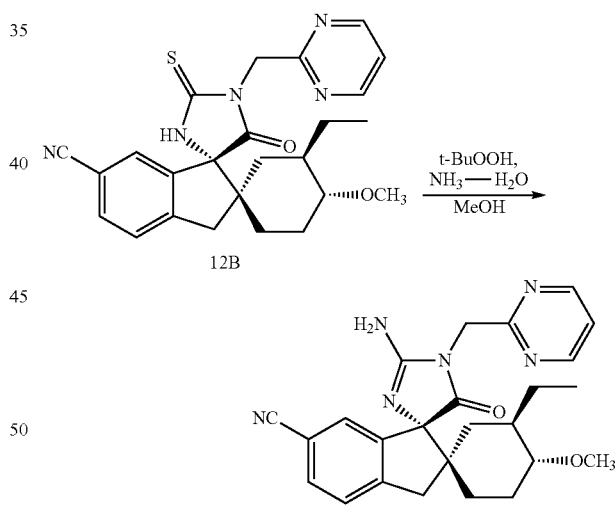

Compound 12B (100 mg, 0.22 mmol) in MeOH (10 mL) and NH₄OH (3 mL) was added followed by t-BuO₂H (1 mL). After the addition, the mixture was stirred at rt for 24 h. To the mixture was quenched with saturated Na₂S₂O₃ (0.5 mL) solution. The residue was partitioned between EtOAc (20 mL) and H₂O (10 mL). The organic layer was separated and washed with brine (10 mL), dried, filtered and concentrated under vacuum. The residue was purified by HPLC (method 1) to give compound Example 1 (14.60 mg, 15%).

LC-MS: $t_R$=0.933 min, MS (ESI) m/z 445.2 [M+H]⁺.

¹H NMR: (CD₃OD): δ 8.74 (d, J=5.2 Hz, 2H), 7.61 (dd, J=7.6, 1.6 Hz, 1H), 7.52 (s, 1H), 7.45 (d, J=8.0 Hz, 1H), 7.35 (t, J=5.2 Hz, 1H), 4.94 (s, 2H), 3.38 (s, 3H), 3.17 (s, 2H), 2.80-2.87 (m, 1H), 2.08-2.13 (m, 1H), 1.90-1.94 (m, 1H), 1.38-1.85 (m, 2H), 1.22-1.39 (m, 3H), 1.12-1.18 (m, 2H), 0.76 (t, J=8.0 Hz, 3H).

Example 2

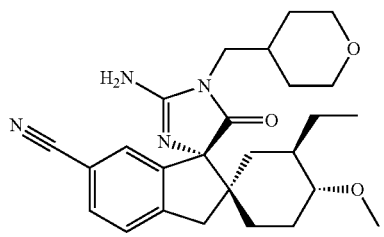 [SMILES: CC[C@@H]1C[C@]2(CC[C@H]1OC)Cc1ccc(C#N)cc1[C@]21N=C(N)N(CC2CCOCC2)C1=O]

This compound was synthesized from intermediate 10B from Example 1 as shown in scheme below.

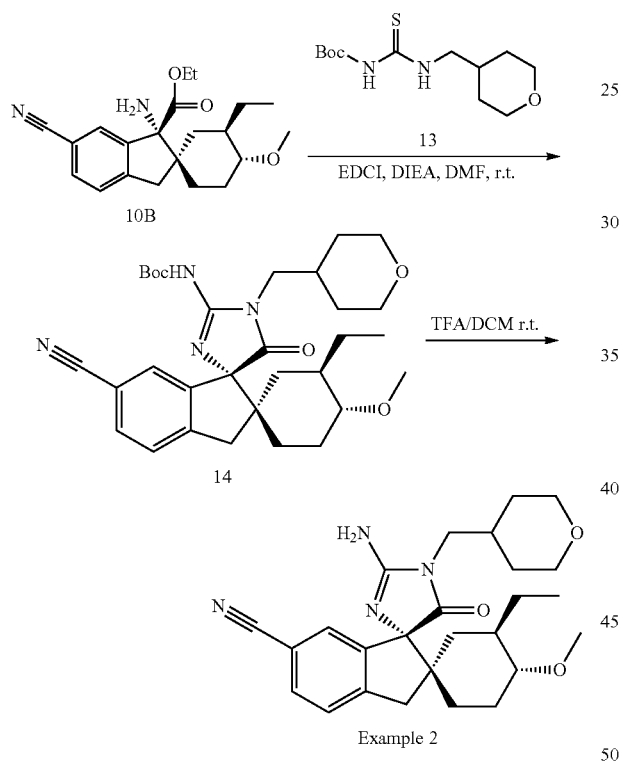

Step 1: Synthesis of Intermediate 13

To a stirred solution of thiourea (23 g, 302 mmol) in THF (5.0 L) under argon at 0° C. were added sodium hydride (29.9 g, 755 mmol, 60% in mineral oil). After 5 min, the ice bath was removed, and the reaction mixture was stirred at room temperature for 10 min. The mixture was cooled to 0° C. again, di-tert-butyl dicarbonate (138 g, 635 mmol) was added, and the ice bath was removed after 30 min of stirring at that temperature. The resulting slurry was stirred for another 2 h at rt. Then the reaction was quenched with an aqueous solution of saturated NaHCO₃ (500 mL). The reaction mixture was poured into water (5.0 L) and extracted with EtOAc (3×2.0 L). The combined organic layer was dried, filtered, and concentrated in vacuo to give intermediate 13 (80 g, 96%) as a white solid, which was used for next step without further purification.

To a mixture of intermediate 13 (4.14 g, 15.0 mmol) and anhydrous THF (300 mL) was added NaH (60% in mineral oil, 720 mg, 18.0 mmol) at 0° C. The reaction mixture was stirred at 0° C. for 1 h, then TFAA (3.47 g/2.33 mL, 16.5 mmol) was added and the stirring continued for an additional 1 h. Then, 4-(aminomethyl)tetrahydropyran (2.5 g, 16.5 mmol) and Et₃N (3.03 g/4.16 mL, 30.0 mmol) in anhydrous THF (130 mL) was added and the resulting reaction was stirred at rt overnight. H₂O (150 mL) was added to quench the reaction and the mixture was extracted with EtOAc (3×200 mL). The combined organic layers were dried, and the solvent was removed under reduced pressure. The residue was purified by flash column chromatography to afford compound 13 (3.54 g, 86%) as a white solid.

LCMS: $t_R$=0.973 min; MS (ESI) m/z 219 [M-t-Bu]⁺.

Step 2: Synthesis of Intermediate 14

To a mixture of compound 10B (2.5 g, 7.0 mmol) in 30 mL of DMF was added compound 13 (2.3 g, 8.4 mmol), EDCI (2.5 g, 14.0 mmol) and DIEA (1.7 g, 14.0 mmol). The mixture was stirred at rt overnight. It was extracted with EtOAc (3×80 mL), washed with brine (3×50 mL), dried and the solvent was removed under reduced pressure. The residue was purified by column chromatography (petroleum ether: ethyl acetate=5:1) to afford 14 (2.7 g, 75%).

LC-MS: $t_R$=0.972 min, MS (ESI) m/z 495.3 [M-t-Bu]⁺.

Step 3: Synthesis of Example 2

To a mixture of intermediate 14 (2.7 g, 4.9 mmol) in DCM (30 mL) was added TFA (6 mL). After the addition, the mixture was stirred at rt for 1 h. The reaction mixture was adjusted by NaHCO₃ solution to pH 8.0-9.0. The organic layer was concentrated under reduced pressure. The residue was purified by column chromatography (petroleum ether: ethyl acetate=1:1) to give compound Example 2 (1.83 g, 83%) as a white solid.

LC-MS: $t_R$=0.897 min, MS (ESI) m/z 451.2 [M+H]⁺.

¹H-NMR: (CD₃OD): δ 7.66 (dd, J=8.0, 1.6 Hz, 1H), 7.51 (d, J=7.6 Hz, 1H), 7.33 (s, 1H), 3.92-3.98 (m, 2H), 3.37-3.43 (m, 7H), 3.20 (m, 2H), 2.78-2.83 (m, 1H), 2.16-2.20 (m, 1H), 1.87-2.03 (m, 1H), 1.71-1.77 (m, 1H), 1.58-1.62 (m, 1H), 1.51-1.54 (m, 2H), 1.28-1.37 (m, 7H), 1.09-1.10 (m, 1H), 0.76 (t, J=7.6 Hz, 3H).

Example 3

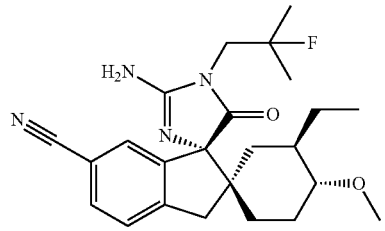 [SMILES: CC[C@@H]1C[C@]2(CC[C@H]1OC)Cc1ccc(C#N)cc1[C@]21N=C(N)N(CC(C)(C)F)C1=O]

Synthesis of Intermediate 18

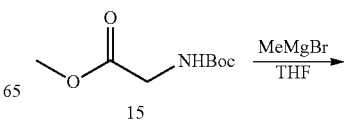

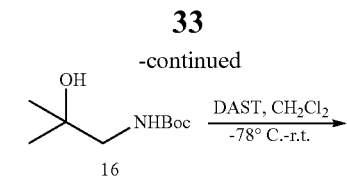

Example 3

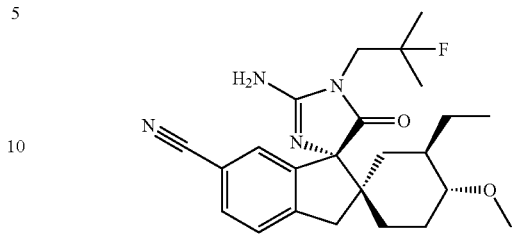

Example 3 was synthesized from intermediate 11B from Example 1 following the same procedure as in Example 1 and utilizing intermediate 18 in step 9 of Example 1.

LC-MS: $t_R$=1.12 min, MS (ESI) m/z 427 [M+H]$^+$.

$^1$H-NMR: (CD$_3$OD) δ 7.65 (dd, 1H, J=8, 2 Hz), 7.51 (d, 1H, J=8 Hz), 7.31 (s, 1H), 3.72 (dd, 2H, J=22, 4 Hz), 3.37 (s, 3H), 3.20 (ap q, 2H, J=16 Hz), 2.82 (m, 1H), 2.18 (m, 1H), 1.90 (m, 1H), 1.79-1.70 (m, 1H), 1.52-11.22 (m, 10H), 1.21-1.09 (m, 1H), 0.77 (t, 3H, J=7 Hz).

Example 4

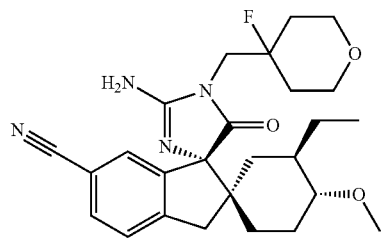 [SMILES: CC[C@@H]1C[C@]2(CC[C@H]1OC)Cc1ccc(C#N)cc1[C@]21N=C(N)N(CC2(F)CCOCC2)C1=O]

Step 1: Synthesis Intermediate 16

Mixture of compound 15 (2.0 g, 10.6 mmol) in anhydrous THF (20 mL) was added to a solution of methyl magnesium bromide (14 mL, 42 mmol, 3.0 M in Et$_2$O) at −30° C. under a nitrogen atmosphere. The mixture was stirred at −30° C. for 4 h, and then quenched by addition of water (40 mL) and aq. HCl (50 mL, 1 M) with stiffing at 0° C. The mixture was separated, and the aqueous layer was extracted with EtOAc (2×50 mL). The combined organic layers were washed with brine (2×50 mL), dried, filtered and concentrated under vacuum to give the crude intermediate 16 (2.1 g, 100% crude) as a colorless oil, which was used directly in next step without purification.

$^1$H NMR: (CDCl$_3$): δ 4.97 (br, 1H), 3.10 (s, 2H), 2.17 (br, 1H), 1.44 (s, 9H), 1.20 (s, 6H).

Step 2: Synthesis of Intermediate 17

To a mixture of intermediate 16 (3.0 g, 15.9 mmol, crude) in anhydrous DCM (50 mL) was added DAST (2.3 mL, 17.4 mmol) at −78° C. under a nitrogen atmosphere. The mixture was stirred at −78° C. for 1 h, and allowed to warm to rt overnight. The mixture was then cooled to 0° C., and quenched by addition of saturated aqueous layer NaHCO$_3$ (30 mL) with stiffing at 0° C. slowly. The mixture was separated, and the aqueous layer was extracted with DCM (2×20 mL). The combined organic layers were washed with brine (2×30 mL), dried, filtered and concentrated under vacuum to give the crude intermediate 17 (2.5 g, 76% crude), which was used directly in next step without purification.

$^1$H NMR: (CDCl$_3$): δ 4.82 (br, 1H), 3.30-3.35 (d, J=6.0 Hz, 1H), 3.24-3.26 (d, J=6.0 Hz, 1H), 1.44 (s, 9H), 1.37 (s, 3H), 1.35 (s, 3H).

$^{19}$F NMR: (CDCl$_3$ 400 MHz): δ −144.93.

Step 3: Synthesis of Intermediate 18

To a mixture of intermediate 17 (2.0 g, 10.5 mmol, crude) in anhydrous DCM (10 mL) was added a mixture of HCl-dioxane (10 mL, 40 mmol, 4 M in dioxane) with stiffing. The mixture was stirred at rt for 2 h after which time the solvent was concentrated under vacuum. The residue was washed with a mixture of DCM: petroleum ether (1:1) (3×10 mL), and the precipitate was collected and dried under vacuum to give the crude compound 18 (1.1 g), which was used directly in the next step without purification.

$^1$H NMR: (CD$_3$OD): δ 3.15-3.25 (d, J=20.0 Hz, 2H), 1.51 (s, 3H), 1.48 (s, 3H).

$^{19}$F NMR: (CDCl$_3$ 400 MHz): δ −147.59.

Synthesis of Intermediate 25

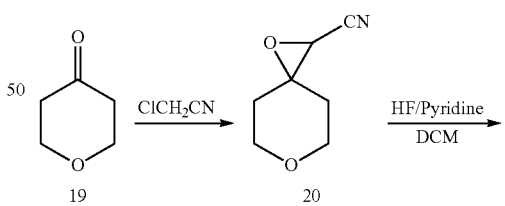

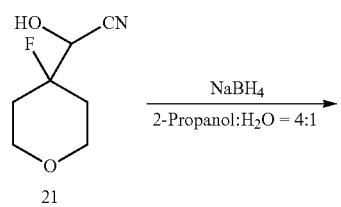

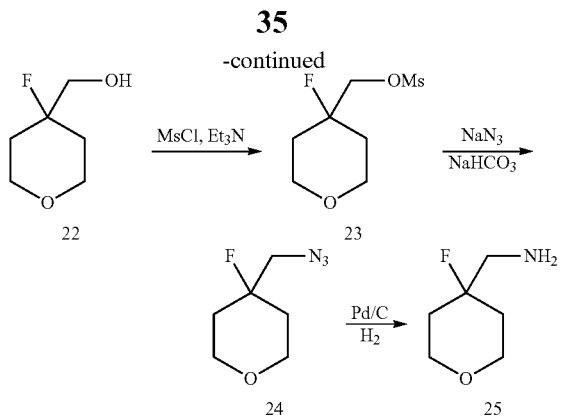

Step 1: Synthesis of Intermediate 20

A mixture of dihydro-2H-pyran-4(3H)-one (19, 50.0 g, 500 mmol) and 2-chloroacetonitrile (35.0 g, 350 mmol) in tert-butanol (50 mL) was stirred for 30 min. To this mixture was added a solution of t-BuOK (60 g, 550 mmol) in tert-butanol (500 mL) over 40 min. The reaction mixture was stirred at rt for 16 h. It was diluted with water and quenched with 10% HCl. The reaction mixture was concentrated to one-third of its original volume, and extracted with diethyl ether four times. The combined organic layers were washed with brine, dried over MgSO$_4$, filtered, and concentrated to afford intermediate 20 (57 g), which was used directly in next step without purification.

Step 2: Synthesis of Intermediate 21

Intermediate 20 (57 g) was mixed with dichloromethane (200 mL) in a polypropylene bottle. The bottle was cooled to 0° C. and 70% hydrogen fluoride-pyridine (50 mL) was added slowly. The mixture was allowed to warm to room temperature overnight. The reaction mixture was diluted with ethyl acetate (500 mL) and poured into saturated aqueous NaHCO$_3$. Additional solid NaHCO$_3$ was used to neutralize the mixture carefully until bubbling ceased. The organic layer was isolated, and the aqueous layer was extracted with ethyl acetate (3×500 mL). The combined organic layers were washed with 1% aqueous HCl solution, brine, dried (MgSO$_4$), filtered and concentrated to give crude intermediate 21 (54 g), which was used directly in the next step without purification.

$^1$H NMR: (CDCl$_3$): δ 4.37 (m, 2H), 3.96-2.70 (m, 4H), 1.97-1.81 (m, 4H).

Step 3: Synthesis of Intermediate 22

To a mixture of intermediate 21 (54 g; 340 mmol) in 2-propanol (1000 mL) and water (250 mL) at 0° C. was added sodium borohydride (20 g, 509 mmol). The mixture was stirred and allowed to warm to rt over 3 h. The reaction was quenched with acetone, and stirred for another 1 h. The clear liquid was separated from solid by decanting. Additional EtOAc was used to wash the solid, and was decanted. The combined organic solution was concentrated. The residue was purified with flash column chromatography on silica gel eluting with 5-20% EtOAc in hexanes to give intermediate 22 (22 g, 40% for 3 steps) as a liquid.

$^1$H NMR: (CDCl$_3$): δ: 3.82-3.77 (m, 4H), 3.72-3.52 (dd, J=20.8, 6.4 Hz, 2H), 2.69 (s, 1H), 1.82-1.60 (m, 4H).

Step 4: Synthesis of Intermediate 23

To a mixture of intermediate 22 (20 g, 150 mmol) and triethylamine (22.7 g, 225 mmol) in DCM (200 mL) was added MsCl (25.8 g, 225 mmol) at 0° C. The mixture was stirred at rt for 2 h, and then water was added. The aqueous layer was extracted with DCM (2×200 mL). The solvent was dried and removed to afford crude intermediate 23 (30 g, 100%), which was used for the next step without further purification.

$^1$H NMR: (CDCl$_3$): δ: 4.22 (d, J=20.0 Hz, 2H), 3.87-3.82 (m, 4H), 3.06 (s, 3H), 1.88-1.68 (m, 4H).

Step 5: Synthesis of Intermediate 24

To a mixture of intermediate 23 (10 g, 47 mmol) with DMF (150 mL) was added NaN$_3$ (16 g, 250 mmol) and NaHCO$_3$ (9.3 mg, 100 mmol) at 120° C. The mixture was stirred at 120° C. for 20 h, the reaction quenched with water, extracted with EtOAc (2×300 mL). The solvent was dried and removed under vacuum to afford crude intermediate 24 (8 g), which was used for the next step without further purification.

Step 6: Synthesis of Intermediate 25

To a mixture of intermediate 24 (8 g, 50 mmol) in ethyl acetate (100 mL) was added Pd/C (0.8 g, 10% content) under a nitrogen atmosphere, the mixture was degassed and exchanged with hydrogen for 3 times. The final mixture was stirred at room temperature under 1 atm. hydrogen atmosphere for 24 h. The catalyst was filtered off through a pad of Celite® and washed with EtOAc (2×50 mL). The combined filtrate was concentrated under reduced pressure to give intermediate 25 (5.3 g, 80%). $^1$H NMR: (CD$_3$OD): δ 3.83-3.79 (m, 4H), 2.76-2.71 (d, J=8.0 Hz, 2H), 1.83-1.65 (m, 4H).

$^{19}$F NMR: (CD$_3$OD, 400 MHz) δ: −169.66.

Example 4

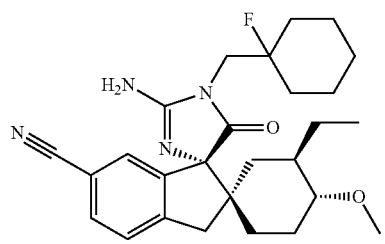 [SMILES: CC[C@@H]1C[C@]2(CC[C@H]1OC)Cc1ccc(C#N)cc1[C@]21N=C(N)N(CC2(F)CCCCC2)C1=O]

Example 4 was synthesized from intermediate 11B following the same procedure as described for Example 1 utilizing intermediate 25 instead of 2-pyrimidylmethanamine in step 9.

LC-MS: t$_R$=0.98 min, MS (ESI) m/z 469 [M+H]$^+$.

$^1$H-NMR: (CD$_3$OD) δ 7.64 (d, 1H, J=8 Hz), 7.50 (d, 1H, J=8 Hz), 7.31 (s, 1H), 3.84-3.65 (m, 6H), 3.36 (s, 3H), 3.19 (ap q, 2H, J=16 Hz), 2.81 (m, 1H), 2.17 (m, 1H), 1.89-1.66 (m, 6H), 1.50-1.37 (m, 3H), 1.34 (m, 2H), 1.20-1.11 (m, 1H), 0.76 (t, 3H, J=8 Hz).

Example 5

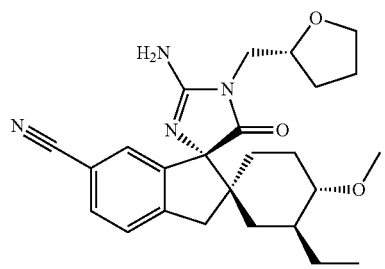 [SMILES: CC[C@H]1C[C@@]2(CC[C@@H]1OC)Cc1ccc(C#N)cc1[C@]21N=C(N)N(C[C@H]2CCCO2)C1=O]

Step 4: Synthesis of Intermediate 7A

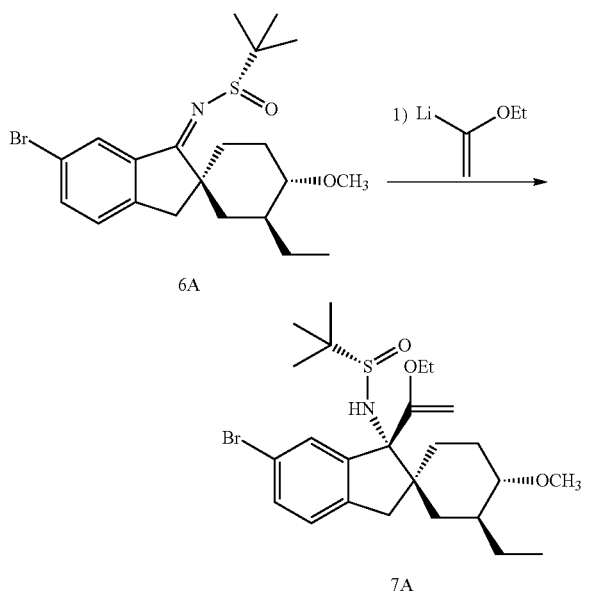

To a mixture of ethoxyethene (1.3 g, 17.0 mmol) in anhydrous THF (20 mL) at −78° C. under a N₂ atmosphere was added dropwise t-BuLi (13.0 mL, 17.0 mmol, 1.3 M in hexane) and the mixture stirred for 20 min. The resulting mixture was then stirred at 0° C. for another 45 min and compound 6A (1.5 g, 3.4 mmol) in anhydrous THF (20 mL) was added and stirred for 2.5 h. The reaction was quenched with sat. NH₄Cl (50 mL) and extracted with EtOAc (3×300 mL). The organic phases were combined and concentrated to give a crude product. It was purified by column on silica gel (petroleum ether:EtOAc=20:1) to afford compound 7A (1.2 g, 69%) which was used as is for the next step.

Step 5: Synthesis of Intermediate 8A

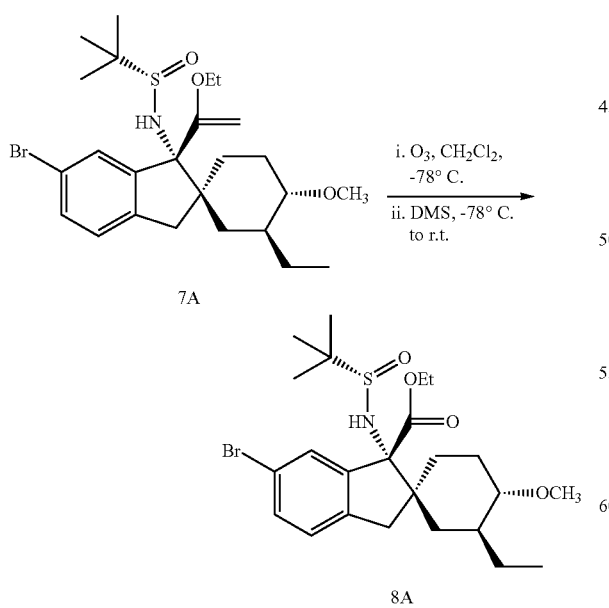

A mixture of compound 7A (1.2 g, 2.4 mmol) in DCM:MeOH=5:1 (20 mL), was chilled to −78° C. and ozone was bubbled through the mixture for 20 min. The mixture was purged with N₂ and treated with Me₂S (5 mL) at −78° C., then allowed to warm to rt and stirred for 3 h. The solvent was removed under vacuum, the residue was purified by preparative TLC (petroleum ether:EtOAc=3:1) to give compound 8A (860 mg, 70%). LC-MS: $t_R$=1.333 min; MS (ESI) m/z 516.1 [M+H]⁺.

Step 6: Synthesis of Intermediate 9A

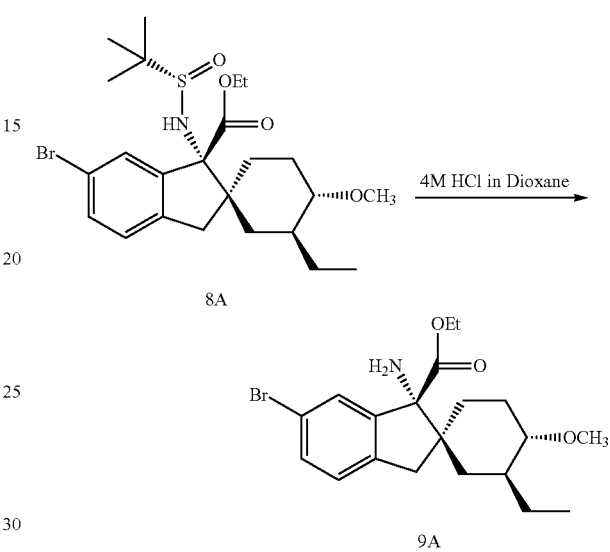

To a mixture of compound 8A (860 mg, 1.7 mmol) in MeOH (10 mL) was added a 4 M HCl solution in dioxane (2 mL). The resulting mixture was stirred for 30 min at rt. Solvent was removed under reduced pressure to afford crude compound 9A (800 mg) which was used for the next step without further purification. LC-MS: $t_R$=0.976 min; MS (ESI) m/z 361.1 [M+H]⁺.

Step 7: Synthesis of Intermediate 10A

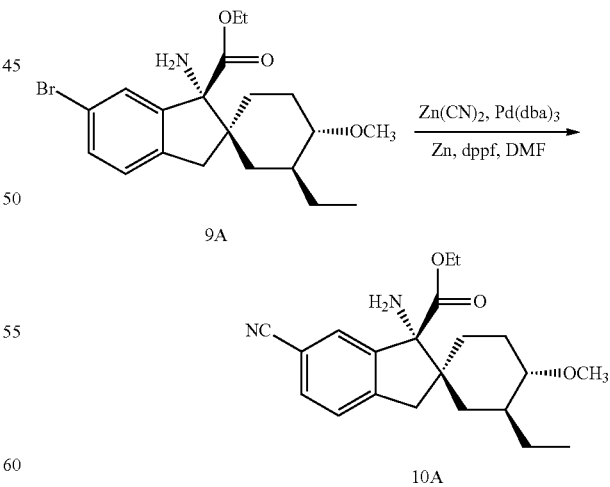

A mixture of compound 9A (500 mg, 1.9 mmol), Zn(CN)₂ (300 mg, 2.6 mmol), Pd₂(dba)₃ (150 mg, 0.16 mmol), dppf (160 mg, 0.32 mmol) and Zn dust (60 mg, 0.9 mmol) in DMF (15 mL) was heated to 120° C. for 3 h in CEM microwave reactor. The mixture was concentrated under vacuum and the residue was purified by column on silica gel (eluent:petroleum ether:EtOAc from 20:1 to 8:1) to afford compound 10A (300 mg, 40%). LC-MS: $t_R$=0.880; MS (ESI) m/z 308.1 [M+H]$^+$.

Step 8: Synthesis of Intermediate 11A

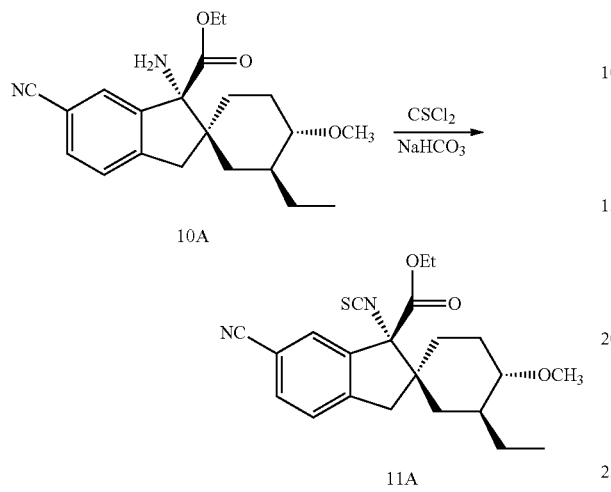

To a mixture of 10A (300 mg, 0.84 mmol) in DCM (10 mL), H$_2$O (10 mL) and NaHCO$_3$ (655 mg, 8.4 mmol) was added thiophosgene (180 mg, 1.68 mmol). The mixture was stirred for 50 min, then extracted with DCM (3×40 mL), washed with brine (2×40 mL), dried and the solvent was removed under reduced pressure to afford crude compound 11A (300 g), which was used for the next step without further purification.

Step 9: Synthesis of Intermediate 12A

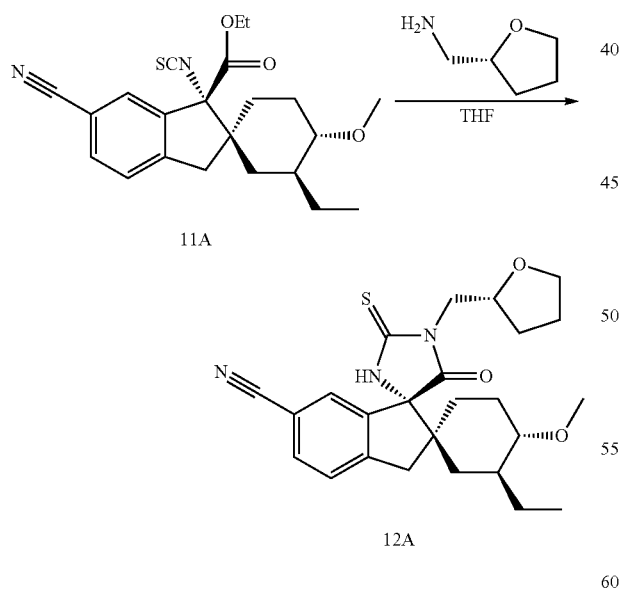

To compound 11A (200 mg, 0.50 mmol) in THF (10 mL) was added to R-(2-aminomethyl)tetrahydrofuran (61 mg, 0.6 mmol) and triethylamine (2 mL, 5.0 mmol). The mixture was stirred at rt overnight. The reaction was diluted with water and extracted with EtOAc (30 mL). The residue was purified by column chromatography (petroleum ether:EtOAc=10:1) to afford 12A (180 mg, 79%).

Step 10: Synthesis of Example 5

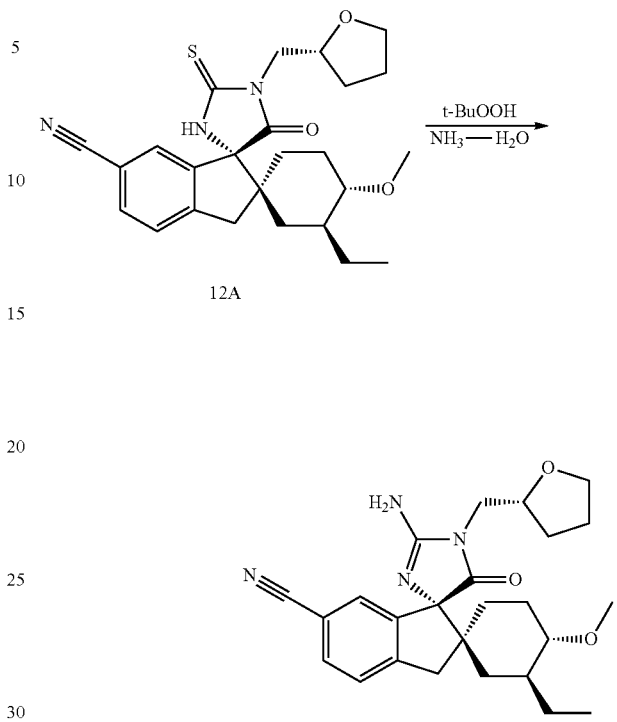

A mixture of intermediate 12A (250 mg, 0.54 mmol) in MeOH (10 mL) and NH$_4$OH (3 mL) was added a solution of t-BuO$_2$H (1 mL, 9M in hexane) and stirred at rt for 24 h. The reaction was quenched by saturated Na$_2$S$_2$O$_3$ (0.5 mL). The residue was partitioned between EtOAc (20 mL) and H$_2$O (10 mL). The organic layer was separated and washed with brine (10 mL), dried, filtered and concentrated under vacuum. The residue was purified by HPLC (method 1) to give Example 5 (89.10 mg, 52%).

LC-MS: tR=0.971 min, MS (ESI) m/z 437.2 [M+H]$^+$.

$^1$H NMR: (CD$_3$OD): δ 7.60 (dd, J=8.0, 1.6 Hz, 1H), 7.46 (d, J=7.6 Hz, 1H), 7.28 (s, 1H), 4.08-4.01 (m, 1H), 3.63-3.90 (m, 4H), 3.33 (s, 3H), 3.09-3.20 (m, 2H), 2.74-2.79 (m, 1H), 1.80-2.06 (m, 5H), 1.65-1.78 (m, 1H), 1.55-1.64 (m, 2H), 1.29-1.35 (m, 3H), 1.07-1.29 (m, 1H), 0.89-0.96 (m, 1H), 0.85 (t, J=7.6 Hz, 3H).

Example 6

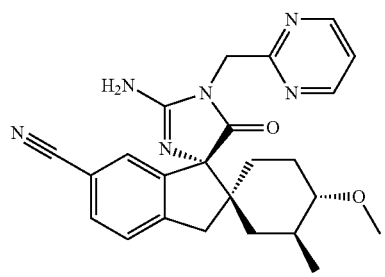 [SMILES: CO[C@H]1CC[C@@]2(Cc3ccc(C#N)cc3[C@]23N=C(N)N(Cc2ncccn2)C3=O)C[C@@H]1C]

Step 1: Synthesis of Intermediate 27

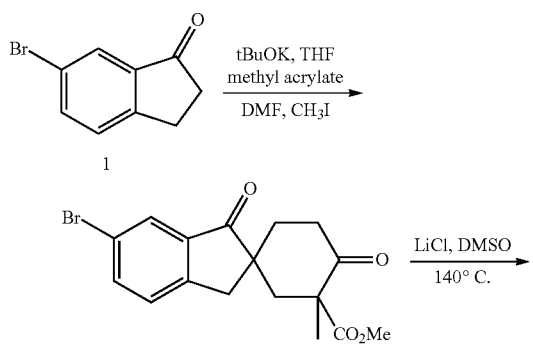

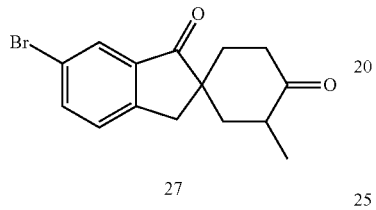

An oven dried 3 L flask charged with of 6-bromo-1-indanone (100 g, 473.8 mmol), methyl acrylate (86.4 g, 90 mL, 995 mmol, 2.1 eq) and anhydrous THF (800 mL), the flask was immersed in an ice-water cooling bath and stirred. Initially, tBuOK (0.5 g) was added carefully, after 2 min, second portion of tBuOK (0.5 g) was added. The cooling bath was removed and remaining tBuOK (63 g) was added in even portions over 20 min (total 64 g, 568.6 mmol, 1.2 eq). The mixture was stirred for another 2 h at rt. DMF (240 mL) was added to the reaction mixture, followed by MeI (134.6 g, 60 mL, 947.6 mmol, 2.0 eq) and the mixture was stirred for another 2 h. The reaction was quenched with 10% citric acid solution. Then the reaction mixture was concentrated under reduced pressure to remove most solvent before it was filtered. The cake was washed with water, followed by MeOH to give the crude intermediate 26 (200 g) which was used in the next step directly.

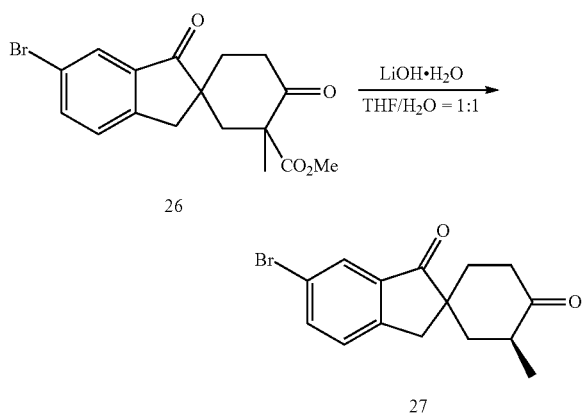

To a solution of compound 26 (200 g, 547.6 mmol, crude) in THF/H$_2$O (1.8 L/1.8 L) was added LiOH.H$_2$O (92 g, 2190 mmol, 4.0 eq). The mixture was stirred for 16 h at rt and then 12 h at 70° C. The reaction mixture was concentrated under reduced procedure to remove THF and filtered. The cake was washed with H$_2$O, and then it was stirred with MeOH (50 mL) for a few min and filtered again, and washed with additional amount of MeOH (50 mL). The solid was collected to give intermediate 27 (75 g, 51.7%).

Step 2: Synthesis of Intermediate 29

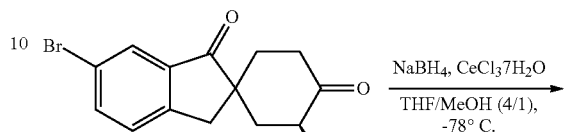

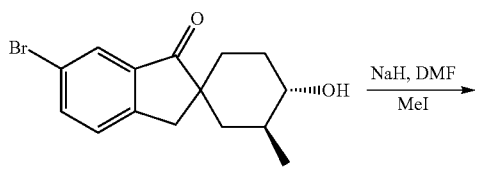

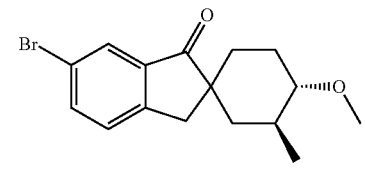

A three neck flask was charged with CeCl$_3$.7H$_2$O (1.2 g, 3.3 mmol) and anhydrous MeOH (60 mL) under a nitrogen atmosphere and stirred to yield clear solution. Compound 27 (10.0 g, 32.6 mmol) and anhydrous THF (240 mL) were added under nitrogen atmosphere, the mixture was cooled down to −78° C. NaBH$_4$ (0.4 g, 13.0 mmol) was added at −78° C. under a nitrogen atmosphere with vigorous stirring. The mixture was stirred at −78° C. for 20 min. The reaction mixture was quenched by addition of saturated aqueous NH$_4$Cl (100 mL) and H$_2$O (200 mL) at −78° C. with stirring. The mixture was slowly allowed to warm to ambient temperature. The mixture was extracted with EtOAc (3×150 mL). The combined organic layers were washed with H$_2$O (2×200 mL), brine (2×200 mL), dried, filtered and concentrated under vacuum, the residue was purified by column chromatography on silica gel eluting with petroleum ether:EtOAc (20:1 to 3:1) to give intermediate 28 (7.5 g, 75%). LC-Ms: t$_R$=3.195 min: MS (ESI) m/z 311.0 [M+H]$^+$.

$^1$H NMR: (CDCl$_3$): δ 7.59 (s, 1H), 7.22-7.25 (d, J=8.4 Hz, 1H), 7.08 (s, 1H), 6.88-6.91 (dd, J=2.4, 8.4 Hz, 1H), 6.80-6.81 (d, J=2.4 Hz, 1H), 5.84 (s, 1H), 4.87 (s, 2H), 4.31-4.36 (m, 2H), 3.50-3.55 (q, J=6.8 Hz, 2H), 3.15-3.25 (m, 1H), 3.09-3.14 (d, J=15.6 Hz, 1H), 3.00-3.06 (d, J=15.2 Hz, 1H), 1.90-2.10 (m, 3H), 1.25-1.50 (m, 5H), 1.15-1.25 (t, J=6.4 Hz, 3H).

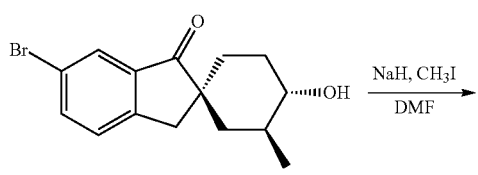

28

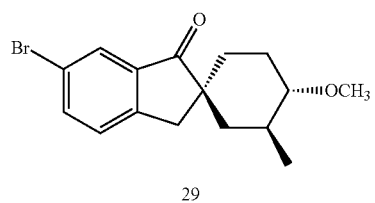

29

To a mixture of compound 28 (6.18 g, 20 mmol) in DMF (20 mL) was added NaH (60% in mineral oil, 0.96 g, 40 mmol) at 0° C. Then the mixture was stirred at 0° C. for 2 h, then MeI (3.5 mL) was added to the mixture and stirred overnight. The mixture was diluted with EtOAc (40 mL) and H₂O (40 mL), extracted with EtOAc (2×60 mL). The combined organic phases were dried and the solvent was removed to give intermediate 29 (5.0 g).

Step 2: Synthesis of Intermediate 30A & 30B

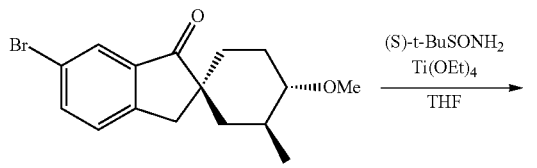

29

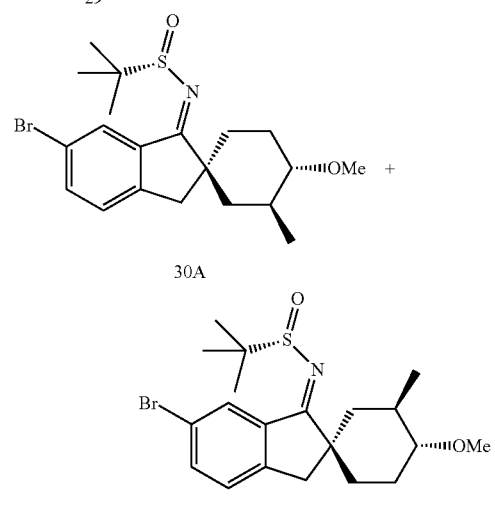

30A

30B

To a solution of intermediate 29 (5.0 g, 15.3 mmol) in THF (100 mL) was added Ti(OEt)₄ (35.0 g, 153 mmol). After being stirred at rt for 1 h, (S)—N-tert-butylsulfinamide (7.4 g, 61.2 mmol) was added. The reaction mixture was stirred at reflux overnight and the mixture was partitioned between H₂O (80 mL) and EtOAc (80 mL). The mixture was filtered and the filtrate was extracted with EtOAc (3×80 mL). The combined organic layers were washed with brine (50 mL), dried and concentrated to the residue. The residue was purified by column chromatography on silica gel (petroleum ether: EtOAc=20:1) eluted in the following order to give intermediate 30A (1.6 g, 35%) and 30B (1.4 g, 33%).

Synthesis of Example 6

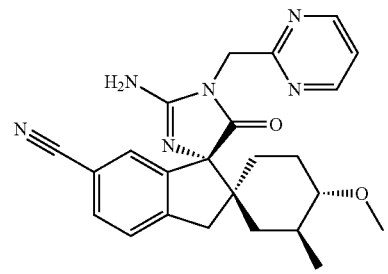 [SMILES: CO[C@H]1CC[C@@]2(Cc3ccc(C#N)cc3[C@]23N=C(N)N(Cc2ncccn2)C3=O)C[C@@H]1C]

Intermediate 30A was further elaborated as illustrated in steps 4 through 10 in Example 5. In step 9, 2-aminomethylpyrimidine was used instead of R-(2-aminomethyl)tetrahydrofuran.

LC-MS: tR=1.05 MS (ESI) m/z 431.4 [M+H]⁺.

¹H NMR: (CD₃OD): δ 8.78 (d, J=4.8 Hz, 2H), 7.76 (s, 1H), 7.75 (dd, J=6.0, 1.6 Hz, 1H), 7.56 (d, J=8.4 Hz, 1H) 7.44 (t, J=5.2 Hz 1H), 5.16 (m, 2H), 3.38 (s, 3H), 3.24 (m, 2H), 2.79 (m, 1H), 2.15 (m, 1H), 1.74 (m, 1H), 1.65 (d, J=6.8 Hz, 1H), 1.39-1.57 (m, 4H), 0.99 (d, J=6.4 Hz, 3H).

Example 7

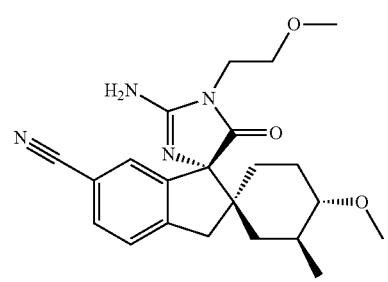 [SMILES: COCCN1C(=O)[C@]2(N=C1N)c1cc(C#N)ccc1C[C@@]21CC[C@H](OC)[C@@H](C)C1]

This was synthesized by a procedure similar as described in Example 6. Intermediate 30A was further elaborated as described in Example 1 through steps 4-10. (2-methoxy) ethylamine was used in step 9 followed by oxidation as described in step 10 to yield Example 7.

LC-MS: tR=1.08 min, MS (ESI) m/z 397 [M+H]⁺.

¹H NMR: (CD₃OD) δ 7.74 (d, 1H, J=8 Hz), 7.63 (d, 1H, J=1 Hz), 7.57 (d, 1H, J=8 Hz), 4.02-3.95 (m, 1H), 3.89-3.83 (m, 1H), 3.54 (m, 2H), 3.36 (s, 3H), 3.35 (s, 3H), 3.24 (ap q,

2H, J=16 Hz)), 2.75 (m, 1H), 2.10 (m, 1H), 1.79 (dt, 1H, J=13, 2 Hz), 1.56 (m, 1H), 1.41 (m, 3H), 1.14 (t, 1H, J=13 Hz), 1.01 (d, 3H, J=6 Hz).

2.04-2.06 (m, 1H), 1.70 (m, 2H), 1.491 (m, 1H), 1.30-1.33 (m, 2H), 1.15-1.18 (m, 1H), 0.95-0.96 (d, J=6.0 Hz, 3H).

Example 8

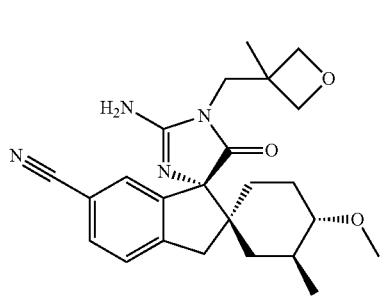 [SMILES: CO[C@H]1CC[C@@]2(Cc3ccc(C#N)cc3[C@]23N=C(N)N(CC2(C)COC2)C3=O)C[C@@H]1C]

Example 10

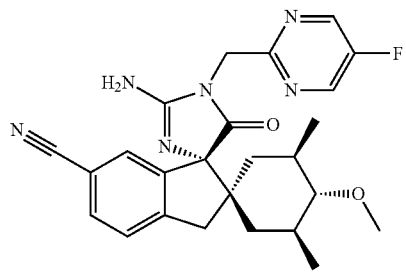

Step 1: Synthesis of Intermediate 32

This was synthesized by a procedure similar as described in Example 6. (3-methyloxetan-3-yl)methanamine was used as described in Example 1 in step 9 followed by oxidation as described in step 10 to yield Example 8.

LC-MS: tR=0.930 min, MS (ESI) m/z 423.0 [M+H]$^+$.

$^1$H NMR: (CD$_3$OD): δ 7.66-7.64 (d, J=7.2 Hz, 1H), 7.51-7.49 (d, J=7.6 Hz, 1H), 7.34 (s, 1H), 4.72-4.67 (m, 2H), 4.29-4.25 (m, 2H), 3.74-3.59 (m, 2H), 3.37 (s, 3H), 3.25-3.14 (m, 2H), 2.74-2.67 (m, 1H), 2.08-2.03 (m, 1H), 1.80-1.53 (m, 3H), 1.30 (m, 5H), 1.08 (m, 1H), 0.90 (m, 3H).

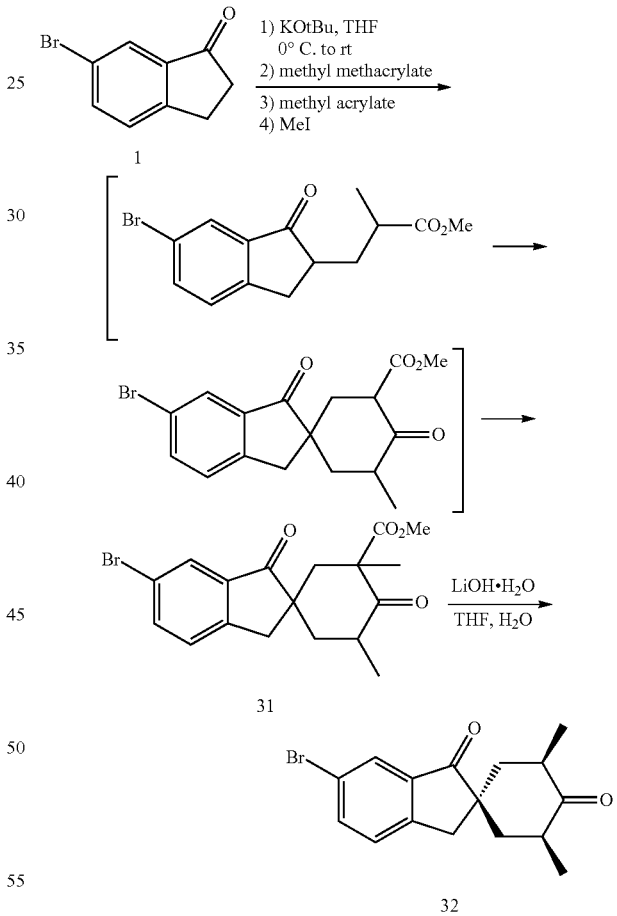

Example 9

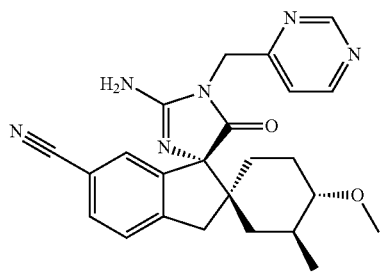 [SMILES: CO[C@H]1CC[C@@]2(Cc3ccc(C#N)cc3[C@]23N=C(N)N(Cc2ccncn2)C3=O)C[C@@H]1C]

This was synthesized by a procedure similar as described in Example 6. 4-(aminomethyl)pyrimidine was used as described in Example 1 in step 9, followed by oxidation as described in step 10 in Example 6 to yield Example 9.

LCMS: t$_R$=0.88 min, MS (ESI) m/z 431.2 [M+H]$^+$.

$^1$H NMR: (CD$_3$OD): δ 9.05 (s, 1H), 8.70-8.71 (d, J=5.2 Hz, 1H), 7.60-7.62 (d, J=7.6 Hz, 1H), 7.44-7.47 (m, 3H), 4.86 (s, 2H), 3.35 (s, 3H), 3.10-3.20 (q, 2H), 2.70-2.71 (m, 1H),

To a mixture of 6-bromo-indan-1-one (100.00 g, 473.8 mmol) in anhydrous THF (1 L) at 0° C. was added t-BuOK (58.5 g, 521.2 mmol, 1.1 eq), 2 min later the mixture was warmed up to rt and was stirred for another 10 min before methyl methacrylate (49.8 g, 53.2 mL, 497.5 mmol, 1.05 eq) was added in one portion. After 2 h, methyl acrylate (49.0 g, 51.2 mL, 568.6 mmol, 1.2 eq) was added to the reaction mixture. After 3 h at rt, MeI (101 g, 44.3 mL, 710.7 mmol, 1.5 eq) was added to the reaction mixture, and it was stirred for 16 h. H₂O (1 L) was added followed by LiOH*H₂O (79.5 g, 1895.2 mmol, 4.0 eq), the mixture was stirred for 28 h at room temperature. THF was removed under reduced pressure. The residue was diluted with H₂O (1 L) and filtered, washed with H₂O until the filtrate was neutral. The product was washed with MeOH to afford 50 g of intermediate 32.

Step 2: Synthesis of Intermediate 33

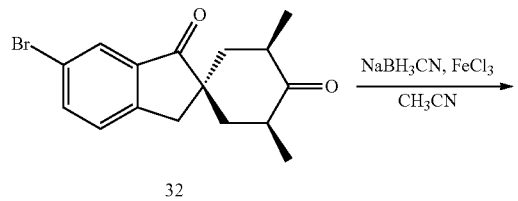

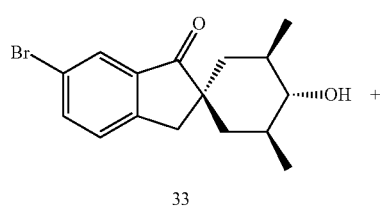

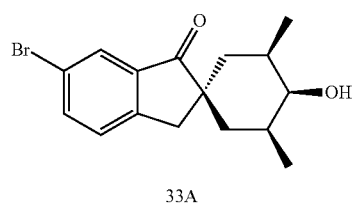

To a mixture of intermediate 32 (60.0 g, 186.9 mmol) and FeCl₃ (33.0 g, 205.5 mmol, 1.1 eq) in THF (600 mL) was added NaBH₃CN (29.4 g, 367.1 mmol, 2.5 eq) at 0° C. The mixture was allowed to warm to room temperature and stirred for 1 h at rt. The reaction was quenched by addition of water and THF was removed under vacuum. It was extracted with DCM (3×200 mL). The combined organic phases were washed with H₂O and brine, dried, and concentrated under vacuum to give the crude product, which was purified by column chromatography on silica gel to generate compound 33 (25.2 g, 42%) and 33A (12.0 g).

LC-MS: tR=1.239 min, MS (ESI) m/z 323.1 [M+H]⁺.

¹H-NMR (CDCl₃): δ: 7.889-7.894 (s, 1H), 7.671-7.696 (d, 1H), 7.311-7.332 (d, 1H), 3.605 (s, 1H), 2.981 (s, 2H), 1.769-1.797 (m, 4H), 1.072-1.082 (m, 2H), 1.019-1.056 (m, 6H).

Step 2: Alternative Synthesis of Intermediate 33

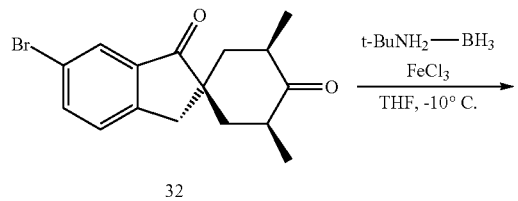

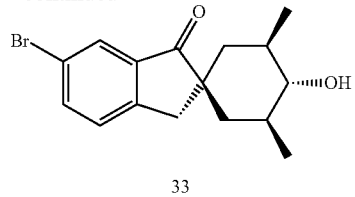

A mixture of FeCl₃ (6.0 g, 37.0 mmol) with toluene (60 mL) was cooled to 0° C. A mixture of compound 32 (11.9 g, 37.0 mmol) in THF (48 mL) was then added to the mixture. The mixture was stirred for 5 min at 0° C. and then cooled to −10° C. A solution of t-BuNH₂—BH₃ (3.5 g, 40.7 mmol) in THF (12 mL) was added dropwise to the reaction mixture at −10° C. The reaction mixture was stirred at about −10° C. for 30 min, quenched with 6N aq HCl solution (10 mL), stirred at about 0° C. for 30 min, and then allowed to warm to room temperature. The mixture was concentrated to remove THF, and toluene (60 mL) was added. The aqueous layer was removed, and the organic phase was washed with water (3×60 mL). The organic phase was concentrated to ½ volume, heated to 50° C. to obtain a solution, and then cooled to 0° C. over 1 h and held at 0° C. for 1 h. The solid was filtered and washed with cold (0° C.) toluene (12 mL), and dried under vacuum to give compound 33 (9.93 g, 83%).

LC-MS: tR=2.36 min, MS (ESI) m/z 323.0/325.0 [M+H]⁺

Step 3: Synthesis of Intermediate 34

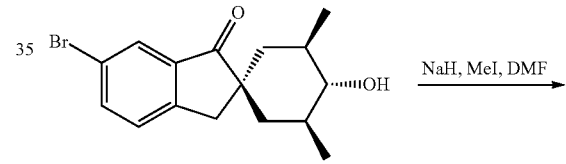

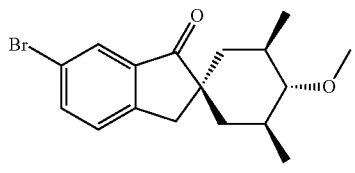

To a mixture of compound 33 (20.0 g, 61.9 mmol) with DMF (200 mL) was added NaH (5.0 g, 123.8 mmol, 2.0 eq) at 0° C. Then it was stirred for 15 min at 0° C. and MeI (17.6 g, 123.8 mmol, 2.0 eq) was added at 0° C. Then it was warmed to rt and stirred for 1.5 h at rt. The mixture was quenched with H₂O and extracted with EtOAc. The combined organic phases were washed with H₂O and brine, dried, concentrated to afford crude product, which was purified by column on silica gel (eluent: petroleum ether:EtOAc from 100/1 to 5/1) to afford intermediate 34 (20 g, 96.2%).

Step 4: Synthesis of Intermediate 35

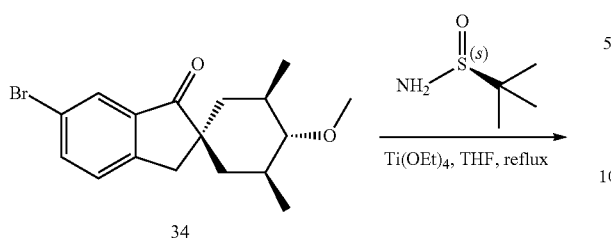

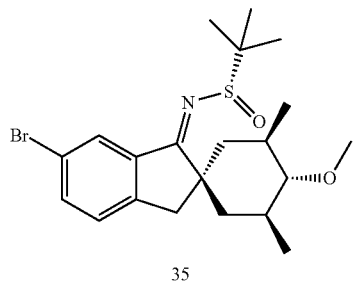

The mixture of compound 34 (20.0 g, 59.3 mmol) and titanium (IV) ethoxide (108.2 g, 474.4 mmol) in dry THF (200 ml) was stirred at rt for 1 h. (S)—N-tert-butylsulfinamide (29 g, 237.2 mmol) was added. The resulting mixture was stirred at 80° C. under $N_2$ atmosphere overnight. The reaction mixture was then cooled and water (400 ml) was added. The mixture was filtered and the aqueous layer was extracted with EtOAc (3×400 mL). The separated organic phase was dried and concentrated under reduced pressure to give crude product. The residue was purified by column chromatography on silica gel (petroleum ether:EtOAc=20:1) to give intermediate 35 (18.4 g, 70.5%).

Step 5: Synthesis of Intermediate 36

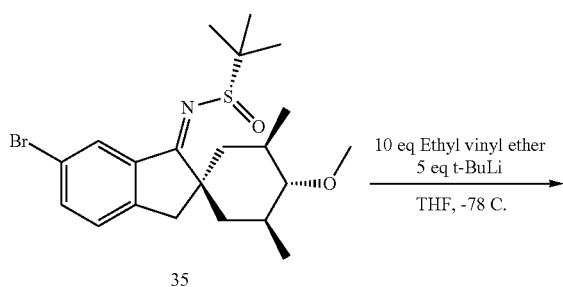

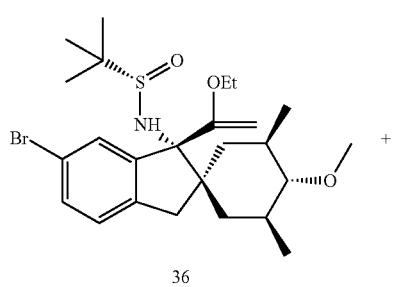

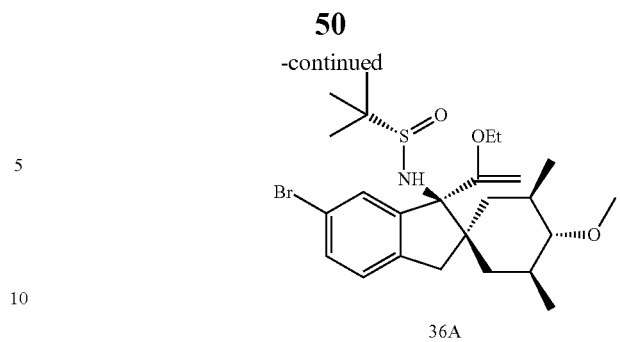

t-BuLi (131 mL, 170.3 mmol, 1.3 M in hexane) was added dropwise to a solution of ethyl vinyl ether (12.3 g, 170.3 mmol, 5.0 eq) in anhydrous THF (100 mL) at −78° C. under $N_2$ and stirred for 20 min. The resulting mixture was then stirred at 0° C. for another 45 min. The solution was re-cooled to −78° C. and compound 35 (15.0 g, 34.1 mmol) in anhydrous THF (50 mL) was added dropwise and the mixture was stirred for 2 h at −78° C. The reaction mixture was quenched with sat. $NH_4Cl$ (50 mL) and extracted with EtOAc (3×300 mL). The organic phase was concentrated to give the residue, which was purified by silica gel column chromatography to afford intermediate 36 (11 g, 64.7%) and 36A (1.441 g, 100% purity).

LC-MS tR=5.676 min; MS (ESI) m/z 514.2 $[M+H]^+$.

$^1$H-NMR ($CD_3OD$): δ 7.546 (s, 1H), 7.454-7.479 (d, 1H), 7.208-7.228 (d, 1H), 4.620-4.755 (d, 1H), 4.373-4.381 (m, 1H), 4.048-4.055 (m, 1H), 3.844-3.903 (m, 2H), 3.458-3.474 (s, 3H), 2.986-3.000 (m, 2H), 2.326-2.377 (m, 1H), 1.969-2.001 (m, 1H), 1.671 (s, 1H), 1.457-1.520 (t, J=12 Hz, 3H), 1.373-1.408 (m, 2H), 1.328 (s, 9H), 1.169-1.278 (m, 5H), 1.073-1.106 (d, 3H).

Step 5: Synthesis of Intermediate 37

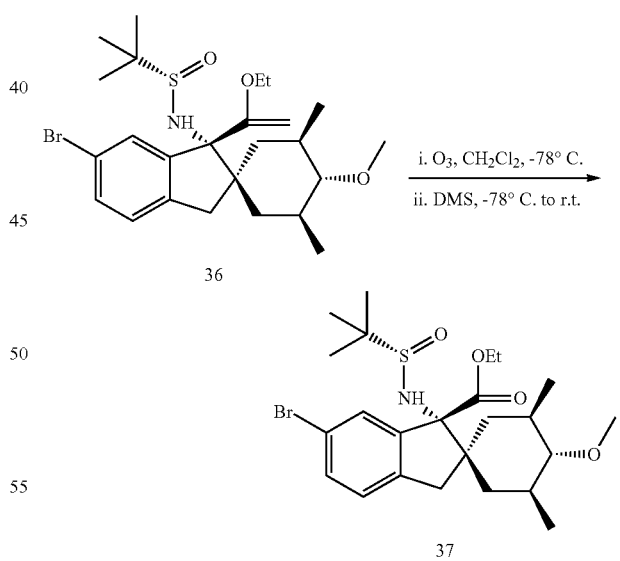

A mixture of intermediate 36 (4.8 g, 9.37 mmol) in DCM:MeOH=5:1 (40 mL), was chilled to −78° C. and ozone was bubbled through the mixture for 20 min. The mixture was then purged with $N_2$ and treated with $Me_2S$ (10 mL) at −78° C., then allowed to warm up to rt and stirred for 3 h. The solvent was removed under vacuum, the residue was purified by column chromatography on silica gel (petroleum ether: EtOAc=20:1 to 8:1) to give intermediate 37 (3.5 g, 72.9%).

LC-MS tR=1.297 min; MS (ESI) m/z 516.1 [M+H]+.
¹H NMR (CDCl₃): δ 7.84 (s, 1H), 7.42-7.44 (d, J=8.0 Hz, 1H), 7.09-7.11 (d, J=8.0 Hz, 1H), 4.40 (s, 1H), 4.26-4.39 (m, 2H), 3.44 (s, 3H), 2.93-2.97 (d, J=15.6 Hz, 1H), 2.70-2.74 (d, J=15.2 Hz, 1H), 2.22-2.30 (t, J=10.0 Hz, 1H), 1.75-1.79 (m, 1H), 1.61-1.66 (m, 1H), 1.54-1.57 (m, 2H), 1.32-1.38 (m, 4H), 1.14 (s, 9H), 1.06-1.08 (d, J=6.0 Hz, 3H), 0.89-0.91 (d, J=6.0 Hz, 3H), 0.67-0.74 (m, 1H).
Step 6: Synthesis of Intermediate 38

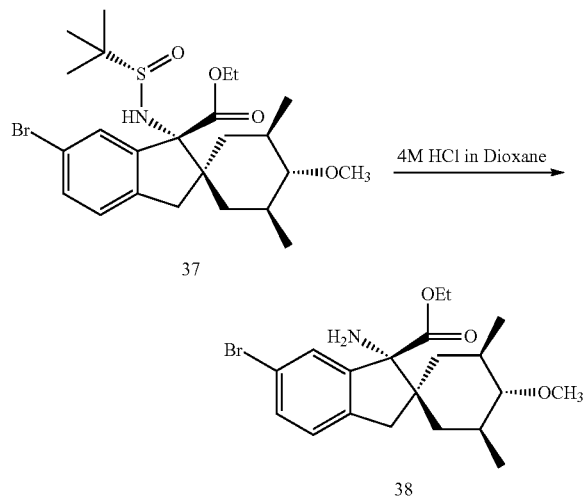

To compound 37 (860 mg, 1.7 mmol) in MeOH (10 mL) was added a 4 M HCl solution in dioxane (2 mL). The resulting mixture was stirred for 30 min. Solvent was removed under reduced pressure to afford crude intermediate 38 (800 mg). The residue was used for the next step without further purification.
Alternative Synthesis of Intermediate 38
Step 1: Synthesis of Intermediate 39

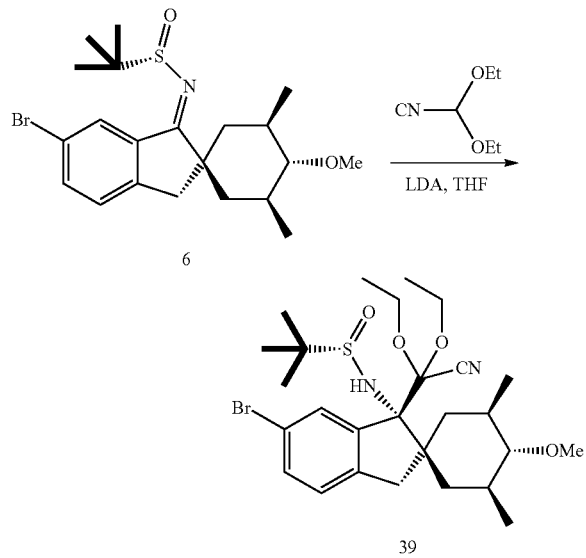

A mixture of intermediate 6 (5.00 g, 11.4 mmol), diethoxy-acetonitrile (3.5 mL, 24.4 mmol) and THF (50 mL) was cooled to −7° C. and treated dropwise with LDA (25.0 mL, 45.0 mmol, 1.8M in THF/heptane/ethylbenzene). The mixture was stirred at −7 to −2° C. for 2 h, and then quenched with water (50 mL) and saturated aqueous NH₄Cl (25 mL). Hexanes (100 mL) was added, and the layers were separated. The organic layer was washed with water, brine, and was concentrated to give crude intermediate 39 (9.00 g, 139%) which was used directly in the next step.
LC-MS: tR=3.74 min, MS (ESI) m/z 523.2/525.2 [M-OEt+H]⁺
Step 2: Synthesis of Intermediate 38

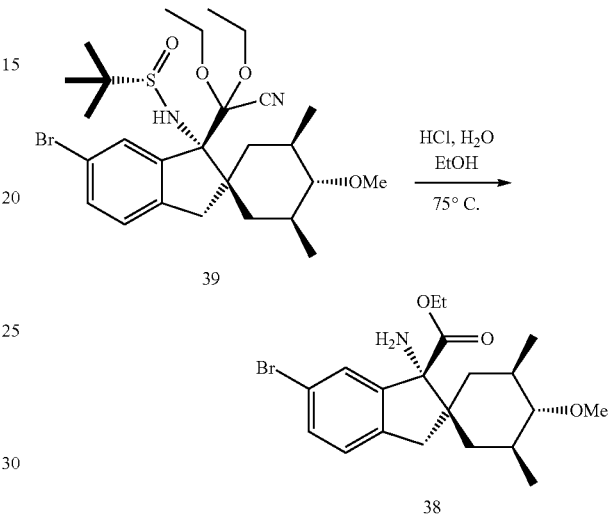

A mixture of above intermediate 39 (9.00 g, 11.4 mmol) in EtOH (30 mL) was treated with 6N aqueous HCl (20 mL). The reaction mixture was heated at 75° C. for 24 h and cooled to rt. The reaction was extracted with toluene (50 mL), and the aqueous phase was then basified to pH=8 with 2N aqueous NaOH (~60 mL). Toluene (100 mL) was added, and the layers were stirred and separated. The organic layer was washed with aqueous NaHCO₃ and brine and concentrated. Hexanes was added and the solution was concentrated again to give crude intermediate 38 (3.47 g, 74%) which was used directly in the next step. LC-MS: tR=0.86 min, MS (ESI) m/z 410.2/412.2 [M+H]⁺
Step 7: Synthesis of Intermediate 40

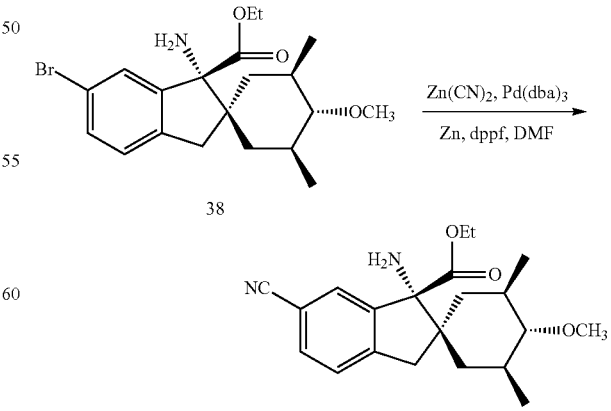

Intermediate 40 was synthesized in an analogous fashion as described in step 7 of intermediate 10A. It was used directly in the next step.

Step 8: Synthesis of Intermediate 41

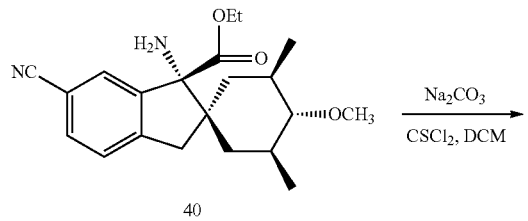

Intermediate 41 was synthesized in an analogous fashion as described in step 8 of intermediate 11A. The crude intermediate 41 was used directly in the next step.

Step 9: Synthesis of Intermediate 42

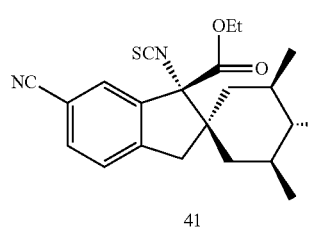

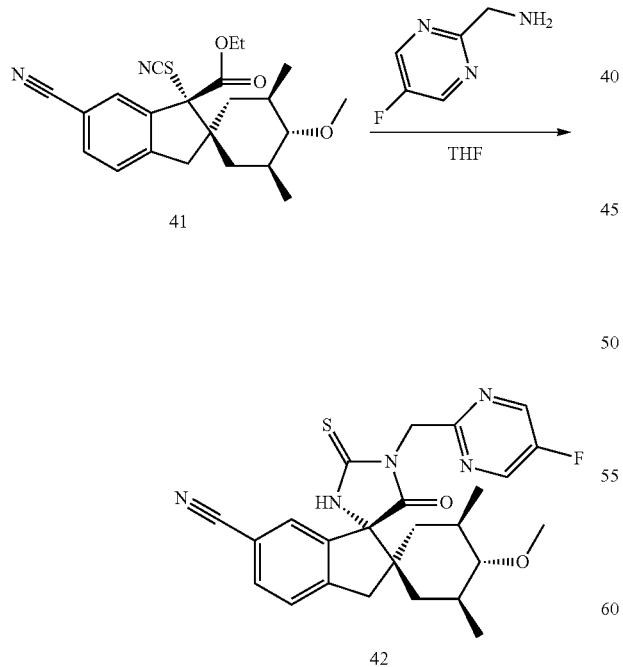

Intermediate 42 was synthesized in an analogous fashion as described in step 9 of intermediate 12A. The crude intermediate 42 was used directly in the next step.

Step 10: Synthesis of Example 10

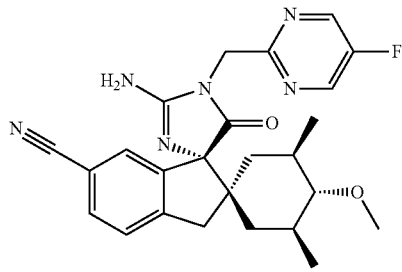 [SMILES: CO[C@H]1[C@H](C)C[C@@]2(Cc3ccc(C#N)cc3[C@]23N=C(N)N(Cc2ncc(F)cn2)C3=O)C[C@@H]1C]

To a solution of intermediate 42 (400 mg, 0.8 mmol) in EtOH (8 mL) was added NH$_3$—H$_2$O (1 mL) and tert-butyl hydroperoxide (1 mL). After addition, the mixture was stirred at room temperature for 12 h. The solvent was removed by evaporation under vacuum. The residue was purified by preparative HPLC method 1 to give Example 6 (65.0 mg, 20% yield).

LC-Ms: $t_R$=0.945 min, MS (ESI) m/z 463.2 [M+H]$^+$.

$^1$H NMR: (CD$_3$OD) δ 8.65-8.70 (s, 2H), 7.60-7.65 (d, J=7.2 Hz, 1H), 7.45-7.55 (m, 2H), 4.95-5.00 (s, 2H), 3.40-3.45 (s, 3H), 3.10-3.20 (m, 2H), 2.30-2.40 (m, 1H), 1.70-1.80 (m, 3H), 1.45-1.55 (m, 1H), 1.25-1.35 (m, 2H), 0.90-1.00 (m, 6H).

$^{19}$F NMR (400 MHz, MeOD): −141.57

Example 11

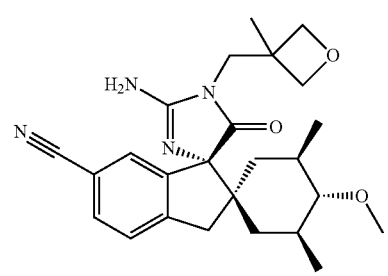 [SMILES: CO[C@H]1[C@H](C)C[C@@]2(Cc3ccc(C#N)cc3[C@]23N=C(N)N(CC2(C)COC2)C3=O)C[C@@H]1C]

Example 11 was synthesized as per procedure described in Example 10. In step 9, (3-methyloxetan-3-yl) methanamine was used instead of (5-fluoropyrimidine)-2-methylamine to yield Example 11

LC-MS: $t_R$=0.96 min, MS (ESI) m/z 437 [M+H]$^+$.

$^1$H NMR: (CD$_3$OD): δ 7.75 (dd, J=7.6, 1.6 Hz, 1H), 7.68 (d, J=1.6 Hz, 1H), 7.56 (d, J=7.6 Hz, 1H), 4.60 (d, J=6.4 Hz, 2H), 4.32 (dd, J=8.0, 6.4 Hz, 2H), 3.97 (d, J=15.6 Hz, 1H), 3.69 (d, J=15.6 Hz, 1H), 3.44 (s, 3H), 3.25 (m, 2H), 2.44 (t,

J=10.0 Hz, 1H), 1.81-1.75 (m, 2H), 1.67 (m, 1H), 1.41 (s, 3H), 1.36 (m, 1H), 1.30-1.21 (m, 2H), 1.07 (d, J=6.4 Hz, 3H), 0.98 (d, J=6.4 Hz, 3H).

2H), 2.32-2.37 (t, J=10.0 Hz, 1H), 1.61-1.71 (m, 3H), 1.38 (m, 1H), 1.19-1.23 (m, 1H), 0.92-0.99 (m, 7H).

Example 12

Example 14

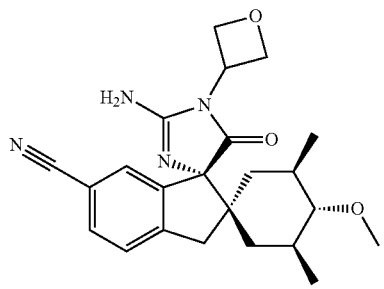 [SMILES: CO[C@H]1[C@H](C)C[C@@]2(Cc3ccc(C#N)cc3[C@]23N=C(N)N(C2COC2)C3=O)C[C@@H]1C]

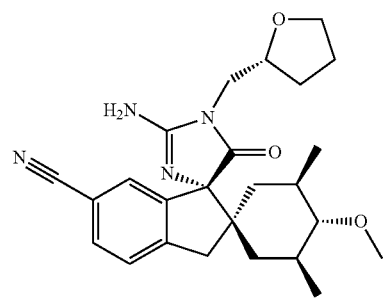

Example 12 was synthesized as per procedure described Example 10. In step 9, 2-aminooxetane was used instead of (5-fluoropyrimidine)-2-methylamine to yield Example 12

LC-MS: $t_R$=0.91 min, MS (ESI) m/z 409 [M+H]$^+$.

$^1$H NMR: (CD$_3$OD): δ 7.75 (dd, J=7.6, 1.2 Hz, 1H), 7.71 (d, J=1.2 Hz, 1H), 7.56 (d, J=7.6 Hz, 1H), 5.28 (m, 1H), 5.13 (dd, J=14.0, 6.8 Hz, 2H), 4.87 (dd, J=8.0, 6.4 Hz, 2H), 3.44 (s, 3H), 3.26 (m, 2H), 2.43 (t, J=10.0 Hz, 1H), 1.85-1.77 (m, 2H), 1.68 (m, 1H), 1.35-1.18 (m, 3H), 1.03 (d, J=6.4 Hz, 3H), 0.97 (d, J=6.4 Hz, 3H).

Example 13

Example 14 was synthesized as per procedure described Example 10. In step 9, (S)-2-(aminomethyl)-tetrahydrofuran was used instead of (5-fluoropyrimidine)-2-methylamine to yield Example 14. LC-MS: $t_R$=1.02 min, MS (ESI) m/z 437 [M+H]$^+$.

$^1$H NMR: (CD$_3$OD): δ 7.75 (d, J=7.6 Hz, 1H), 7.53 (d, J=7.6 Hz, 1H), 7.35 (s, 1H), 4.16 (m, 1H), 3.96 (m, 1H), 3.83 (m, 1H), 3.70 (m, 2H), 3.50 (s, 3H), 3.30 (d, J=15.6 Hz, 1H), 3.19 (d, J=15.6 Hz, 1H), 2.42 (t, J=10.0 Hz, 1H), 2.08-1.95 (m, 3H), 1.88-1.1.63 (m, 4H), 1.55 (m, 1H), 1.40-1.30 (m, 2H), 1.05 (d, J=6.4 Hz, 3H), 1.01 (d, J=6.4 Hz, 3H).

Example 15

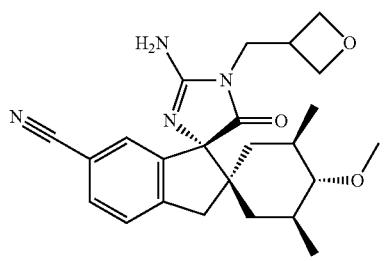 [SMILES: CO[C@H]1[C@H](C)C[C@@]2(Cc3ccc(C#N)cc3[C@]23N=C(N)N(CC2COC2)C3=O)C[C@@H]1C]

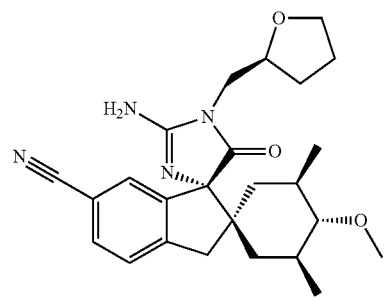 [SMILES: CO[C@H]1[C@H](C)C[C@@]2(Cc3ccc(C#N)cc3[C@]23N=C(N)N(C[C@@H]2CCCO2)C3=O)C[C@@H]1C]

Example 13 was synthesized as per procedure described Example 10. In step 9, oxetan-3-ylmethanamine was used instead of (5-fluorpyriminde)-2-methylamine to yield Example 13.

LC-MS: $t_R$=0.904 min; MS (ESI) m/z 423.3 [M+H]$^+$.

$^1$H NMR: (CD$_3$OD): δ 7.60-7.62 (d, J=8.0 Hz, 1H), 7.45-7.47 (d, J=8.0 Hz, 1H), 7.27 (s, 1H), 4.69-4.73 (d, J=7.2 Hz, 2H), 4.44-4.49 (d, J=7.2 Hz, 2H), 3.85-3.91 (m, 1H), 3.74-3.80 (m, 1H), 3.42 (s, 3H), 3.34-3.38 (m, 1H), 3.08-3.22 (m,

Example 15 was synthesized as per procedure described in Example 10. In step 9, (R)-2-(aminomethyl)-tetrahydrofuran was used instead of (5-fluoropyrimidine)-2-methylamine to yield example 15. LC-MS: $t_R$=1.02 min, MS (ESI) m/z 437 [M+H]$^+$.

$^1$H NMR: (CD$_3$OD): δ 7.61 (d, J=8.0 Hz, 1H), 7.46 (d, J=8.0 Hz, 1H), 7.25 (s, 1H), 4.07 (m 1H), 3.88 (m, 1H), 3.73 (m, 1H), 3.66 (dd, J=14.8, 3.2 Hz, 1H), 3.57 (dd, J=14.8, 6.8 Hz, 1H), 3.42 (s, 3H), 3.23 (d, J=16.0 Hz, 1H), 3.10 (d, 16.0 Hz, 1H), 2.35 (t, J=10.4 Hz, 1H), 2.01-1.86 (m, 3H), 1.76-

1.50 (m, 4H), 1.44 (t, J=13.2 Hz, 1H), 1.24 (m, 1H), 1.03 (t, J=12.8 Hz, 1H), 0.98 (d, J=6.4 Hz, 3H), 0.93 (d, J=6.4 Hz, 1H).

Example 16

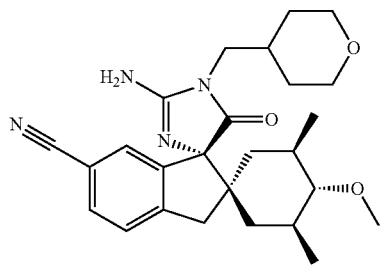 [SMILES: CO[C@H]1[C@H](C)C[C@@]2(Cc3ccc(C#N)cc3[C@]23N=C(N)N(CC2CCOCC2)C3=O)C[C@@H]1C]

Example 16 was synthesized as per procedure described in Example 10. In step 9,2-(aminomethyl)-tetrahydropyran was used instead of (5-fluoropyrimidine)-2-methylamine to yield Example 16

LC-MS: $t_R$=0.958 min, MS (ESI) m/z 451.3 [M+H]$^+$.

$^1$H NMR (CD$_3$OD): δ 7.62-7.65 (d, J=7.6 Hz, 1H), 7.48-7.50 (d, J=8.0 Hz, 1H), 7.30 (s, 1H), 3.93-3.96 (m, 2H), 3.37-3.45 (m, 7H), 3.23-3.27 (d, J=16.0 Hz, 1H), 3.11-3.15 (d, J=16.0 Hz, 1H), 2.35-2.40 (t, J=10.0 Hz, 1H), 1.96-2.03 (m, 1H), 1.53-1.80 (m, 5H), 1.23-1.46 (m, 4H), 0.92-1.08 (m, 7H).

Example 17

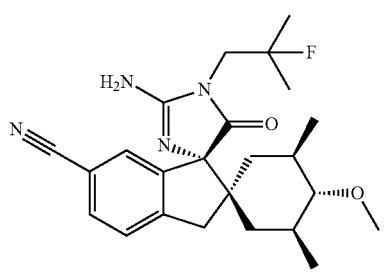 [SMILES: CO[C@H]1[C@H](C)C[C@@]2(Cc3ccc(C#N)cc3[C@]23N=C(N)N(CC(C)(C)F)C3=O)C[C@@H]1C]

Example 17 was synthesized as per procedure described in Example 10. In step 9, intermediate 18 was used instead of (5-fluoropyrimidine)-2-methylamine to yield Example 17.

LC-MS: $t_R$=0.969 min, MS (ESI) m/z 427.2 [M+H]$^+$.

$^1$H NMR: (CD$_3$OD): δ 7.63-7.65 (d, J=8.0 Hz, 1H), 7.49-7.51 (d, J=8.0 Hz, 1H), 7.30 (s, 1H), 3.70-3.76 (m, 2H), 3.45 (s, 3H), 3.13-3.28 (m, 2H), 2.36-2.41 (t, J=10.0 Hz, 1H), 1.65-1.84 (m, 3H), 1.48-1.51 (m, 1H), 1.37-1.42 (m, 6H), 1.26-1.33 (m, 1H), 1.02-1.09 (m, 1H), 0.92-1.00 (m, 6H). $^{19}$F NMR: (CD$_3$OD): δ-139.58.

Example 18

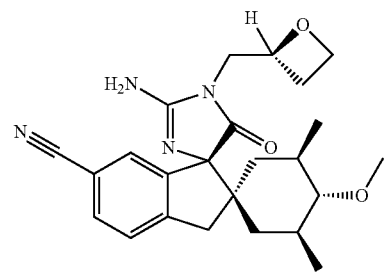 [SMILES: CO[C@H]1[C@H](C)C[C@@]2(Cc3ccc(C#N)cc3[C@]23N=C(N)N(C[C@@H]2CCO2)C3=O)C[C@@H]1C]

Step 9: Synthesis of Intermediate 43

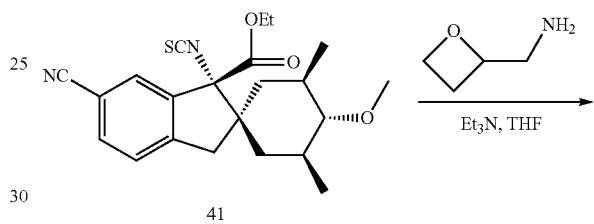

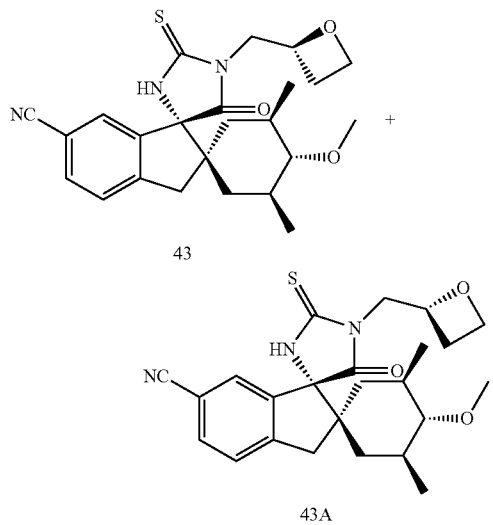

To a solution of compound 41 (1 g, 2.51 mmol) in THF (25 mL) was added compound 2-(2-aminomethyl)oxetane (262 mg, 3.01 mmol) and triethylamine (760 mg, 7.53 mmol). The mixture was stirred at rt overnight. The reaction mixture was diluted with EtOAc (45 mL), followed by saturated aqueous NaHCO$_3$ (2×35 mL) and brine (2×35 mL). Solvent was removed after dried to give crude compound 43 and 43A which was purified under SFC-method A. The diastereomers were separated by a SFC-method B. The desired diastereomer 43 was isolated as a second peak under these conditions. This was further elaborated as described in step 10 of Example 10 to yield Example 18.

LC-MS: $t_R$=0.863 min, MS (ESI) m/z 423.1 [M+H]$^+$.

$^1$H NMR: (CD$_3$OD): δ 7.61-7.63 (d, J=8.0 Hz, 1H), 7.47-7.49 (d, J=7.6 Hz, 1H), 7.30 (s, 1H), 4.95-5.01 (m, 1H), 4.65-4.70 (m, 1H), 4.52-4.58 (m, 1H), 3.73-3.85 (m, 2H), 3.43 (s, 3H), 3.22-3.26 (d, J=16.0 Hz, 1H), 3.10-3.14 (d, J=16.4 Hz, 1H), 2.64-2.72 (m, 1H), 2.33-2.45 (m, 2H), 1.59-1.76 (m, 3H), 1.40-1.49 (m, 1H), 1.22-1.27 (m, 1H), 0.93-1.07 (m, 7H).

Example 19

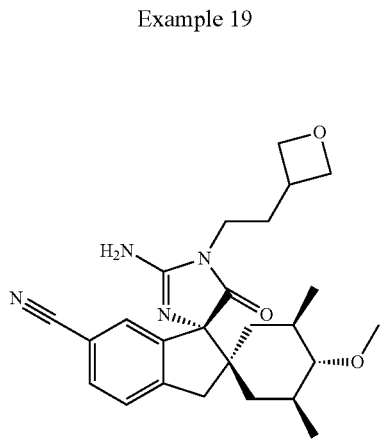

Synthesis of 3-((2-amino)ethyl)oxetane

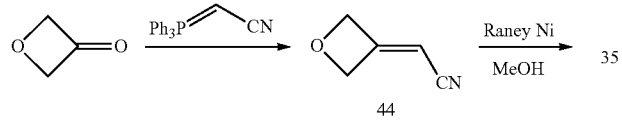

Step 1: Synthesis of Intermediate 44

To 3-oxanone (0.42 g, 6 mmol) in DCM (20 mL) was added 2-(triphenylphosphoranylidene)acetonitrile (1.8 g, 6 mmol) and stirred overnight at rt. After which time, the solvent was removed under reduced pressure to afford crude product (260 mg, crude), which was purified by chromatography on silica gel (petroleum:EtOAc, 3:1) to give intermediate 44 (260 mg, yield 46%) as a white solid.

Step 2: Synthesis of Intermediate 45

To a mixture of intermediate 44 (260 mg, 2.74 mmol) in MeOH (10 mL) was added Raney-Ni (100 mg) and stirred at rt under hydrogen atmosphere for 12 h. The mixture was then filtered through a pad of Celite®. The filtrate was concentrated to give intermediate 45 (200 mg, crude).

Example 19

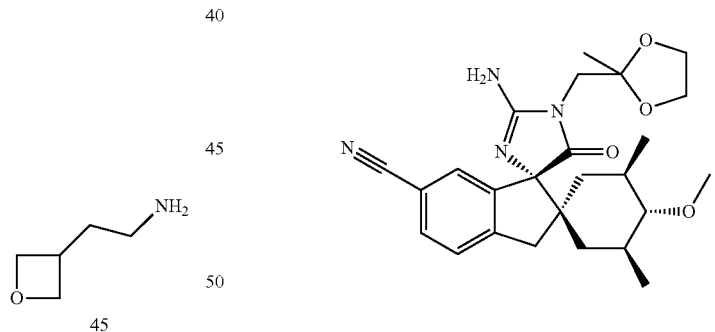

Example 19 was synthesized as per procedure described in Example 10. In step 9, intermediate 45 was used to yield Example 19.

LCMS: tR=2.358 min, MS (ESI) m/z 437.3 [M+H]⁺.

¹H NMR: (CD₃OD): δ 7.64-7.66 (d, 1H), 7.49-7.51 (d, J=8.0 Hz, 1H), 7.31 (s, 1H), 4.74-4.79 (d, 2H), 4.40-4.43 (d, 2H), 3.49-3.52 (m, 2H), 3.45 (s, 3H), 2.95-3.27 (m, 3H), 2.36-2.41 (m, 1H), 1.97-2.05 (m, 2H), 1.21-1.80 (m, 5H), 1.01-1.09 (m, 4H), 0.92-0.99 (m, 3H).

Example 20

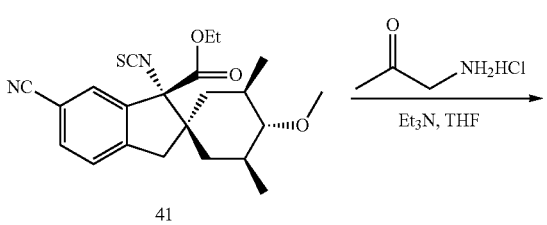

Step 1: Synthesis of Intermediate 46

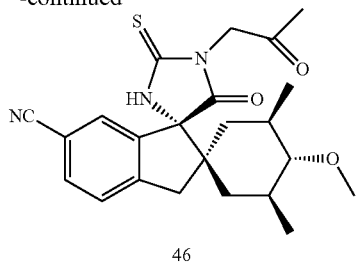

46

To a solution of compound 41 (100 mg, 0.25 mmol) in dry THF (3 mL) was added 2-aminoacetone hydrochloride (41 mg, 0.377 mmol) and triethylamine (76 mg, 0.754 mmol). The mixture was stirred overnight at rt. The reaction was quenched by adding water (3 mL) and extracted with EtOAc (2×5 mL). The combined organic layers were dried and evaporated under vacuum. The crude material was purified by prep-TLC to afford compound 46 (50 mg, 24%).

Step 2: Synthesis of Intermediate 47

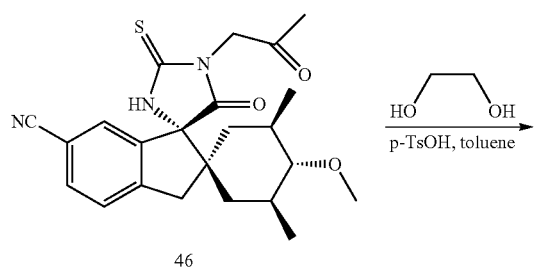

46

To a solution of compound 46 (50 mg, 0.118 mmol) in toluene (3 mL) was added ethylene glycol (0.03 mL) and p-toluene sulfonic acid (1.1 mg, 0.0068 mmol). The solution was heated to reflux for 2 days. The reaction mixture was cooled to rt and brine (3 mL) was added. The mixture was extracted with EtOAc (2×5 mL). The combined organic layers were dried and evaporated under vacuum. The crude material was purified by prep-TLC to afford compound 47 (51 mg, %).

Step 3: Synthesis of Example 20

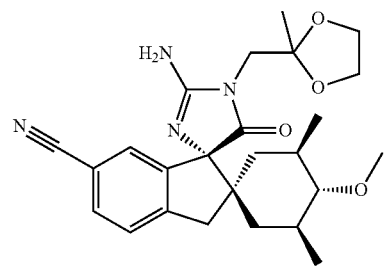 [SMILES: CO[C@H]1[C@H](C)C[C@@]2(Cc3ccc(C#N)cc3[C@]23N=C(N)N(CC2(C)OCCO2)C3=O)C[C@@H]1C]

47

To a mixture of compound 47 (51 mg, 0.113 mmol) in MeOH (2.5 mL) was added aqueous ammonia (0.8 mL), t-BuOOH (2.5 mL). The mixture was stirred overnight at rt. Then sat. $Na_2S_2O_3$ (2.5 mL) was added to quench the reaction. The mixture was extracted with EtOAc (2×5 mL). The combined organic layers were dried and evaporated under vacuum. The crude material was purified by basic prep-HPLC to afford Example 20 (12.8 mg, 25%) as a white solid.

1H-NMR (CD$_3$OD): δ 7.60 (d, J=8.1 Hz, 1H), 7.50 (d, J=8.1 Hz, 1H), 7.22 (s, 1H), 3.86-4.01 (m, 4H), 3.64-3.75 (m, 2H), 3.42 (s, 3H), 3.03-3.23 (m, 2H), 2.34 (t, 1H), 1.61-1.84 (m, 3H), 1.43 (s, 1H), 1.20-1.37 (m, 4H), 0.89-1.08 (m, 7H).

LC-MS tR=0.891 min, MS (ESI) m/z 453.3 [M+H]$^+$

Example 21

Example 21 was synthesized as per procedure described in Example 10. In step 9, (R)-(1,4-dioxan-2-yl)methanamine was used to yield Example 21.

LC-MS: $t_R$=0.928 min, MS (ESI) m/z 453.3 [M+H]$^+$.

$^1$H NMR: (CD$_3$OD): δ 7.63-7.61 (dd, J=1.6 Hz, 4.0 Hz, 1H), 7.48 (d, 1H), 7.3 (s, 1H), 3.6-3.8 (m, 6H), 3.6-3.5 (m,

2H), 3.45 (s, 3H), 3.3-3.1 (m, 3H), 2.4 (m, 1H), 1.8-1.6 (m, 3H), 1.6-1.4 (m, 1H), 1.3-1.2 (m, 1H), 1.1 (m, 1H), 0.9-1.01 (m, 6H).

(m, 7H), 1.46 (m, 1H), 1.23 (m, 1H), 1.06 (m, 1H), 0.99-0.92 (m, 6H). $^{19}$F NMR: (CD$_3$OD 400 MHz): δ −160.19.

Example 22

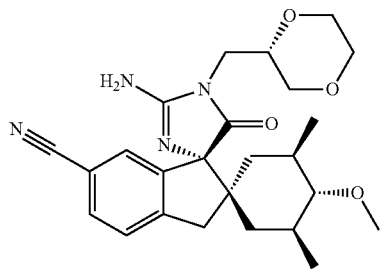 [SMILES: CO[C@H]1[C@H](C)C[C@@]2(Cc3ccc(C#N)cc3[C@]23N=C(N)N(C[C@H]2COCCO2)C3=O)C[C@@H]1C]

Example 22 was synthesized as per procedure described in Example 10. In step 9, (S)-(1,4-dioxan-2-yl)methanamine was used instead of (5-fluoropyrimidine)-2-methylamine to yield Example 22.

LC-MS: $t_R$=0.928 min, MS (ESI) m/z 453.3 [M+H]$^+$.

$^1$H NMR: (CD$_3$OD): δ 7.63-7.61 (dd, J=1.6 Hz, 4.0 Hz, 1H), 7.48 (d, 1H), 7.3 (s, 1H), 3.6-3.8 (m, 6H), 3.6-3.5 (m, 2H), 3.45 (s, 3H), 3.3-3.1 (m, 3H), 2.4 (m, 1H), 1.8-1.6 (m, 3H), 1.6-1.4 (m, 1H), 1.3-1.2 (m, 1H), 1.1 (m, 1H), 0.9-1.01 (m, 6H).

Example 23

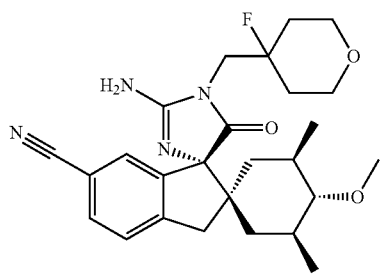 [SMILES: CO[C@H]1[C@H](C)C[C@@]2(Cc3ccc(C#N)cc3[C@]23N=C(N)N(CC2(F)CCOCC2)C3=O)C[C@@H]1C]

Example 23 was synthesized as per procedure described in Example 10. In step 9, intermediate 25 was used to yield Example 23.

LC-MS: tR=0.918 min, MS (ESI) m/z 469.2[M+H]$^+$.

$^1$H NMR: (CD$_3$OD): δ 7.62 (d, J=8.0 Hz, 1H), 7.48 (d, J=8.0 Hz, 1H), 7.27 (s, 1H), 3.88-3.79 (m, 3H), 3.73-3.62 (m, 3H), 3.43 (s, 3H), 3.25-3.09 (m, 2H), 2.36 (t, 1H), 1.81-1.60

Example 24

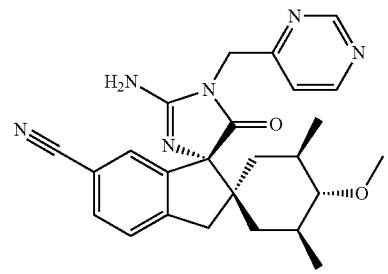 [SMILES: CO[C@H]1[C@H](C)C[C@@]2(Cc3ccc(C#N)cc3[C@]23N=C(N)N(Cc2ccncn2)C3=O)C[C@@H]1C]

Example 24 was synthesized as per procedure described in Example 10. In step 9,3-pyrimidyl-methanamine was used instead of (5-fluoropyrimidine)-2-methylamine to yield Example 24.

LC-MS: $t_R$=0.867 min, MS (ESI) m/z 445.1 [M+H]$^+$.

$^1$H NMR: (CD$_3$OD): δ 9.08 (s, 1H), 8.74 (d, J=5.2 Hz, 1H), 7.65 (d, J=7.6 Hz, 1H), 7.48 (m, 3H), 4.90 (s, 2H), 3.46 (s, 3H), 3.12-3.24 (m, 2H), 2.41 (m, 1H), 1.63-1.75 (m, 3H), 1.49 (m, 1H), 1.28 (m, 2H), 1.02 (d, J=6.4 Hz, 3H), 0.96 (d, J=6.4 Hz, 3H).

Example 25

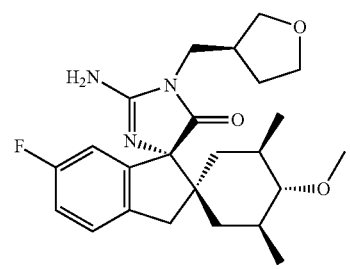 [SMILES: CO[C@H]1[C@H](C)C[C@@]2(Cc3ccc(F)cc3[C@]23N=C(N)N(C[C@@H]2CCOC2)C3=O)C[C@@H]1C]

Example 25 was synthesized in a method similar to Example 18. In step 9, (tetrahydrofuran-3-yl)methanamine was utilized and the two diastereomers were separated by SFC-Method B. Further elaboration of intermediate arising out of the second peak from the SFC-Method B yielded Example 26.

LCMS: tR=0.845 min; m/z 430.3[M+H]$^+$.

$^1$H NMR: (CD$_3$OD): δ 7.63-7.66 (m, 1H), 7.49-7.51 (m, 1H), 7.31 (s, 1H), 3.84-3.93 (m, 1H), 3.71-3.81 (m, 2H), 3.48-3.63 (m, 3H), 3.43 (s, 3H), 3.11-3.31 (m, 2H), 2.51-2.78 (m, 2H), 1.22-2.09 (m, 7H), 1.00-1.06 (m, 4H), 0.93-0.99 (m, 3H).

Example 26

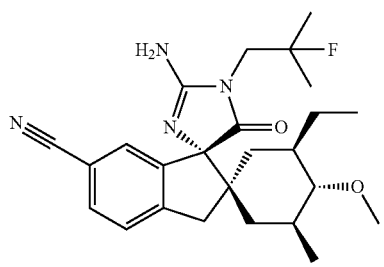 [SMILES: CC[C@@H]1C[C@@]2(Cc3ccc(C#N)cc3[C@]23N=C(N)N(CC(C)(C)F)C3=O)C[C@H](C)[C@H]1OC]

Example 26 was synthesized in a method similar to Example 1. In the synthesis of Example 28, in step 1 of Example 1, methyl methacrylate was used instead of methyl acrylate. In step 3, the corresponding polar isomer 6B was isolated and further elaborated as described in Example 1. In step 9, intermediate 17 was utilized to yield Example 28.

LC-MS: $t_R$=1.16 min, MS (ESI) m/z 441 [M+H]$^+$.

$^1$H NMR (CD$_3$OD): δ 7.64 (dd, 1H, J=8, 2 Hz), 7.50 (d, 1H, J=8 Hz), 7.30 (s, 1H), 3.73 (dd, 2H, J=22, 4 Hz), 3.44 (s, 3H), 3.19 (ap q, 2H, J=16 Hz), 2.49 (t, 1H, J=10 Hz), 1.82-1.72 (m, 2H), 1.71-1.63 (m, 1H), 1.55 (m, 1H), 1.42-1.33 (m, 8H), 1.22-1.12 (m, 1H), 1.08 (t, 1H, J=13 Hz), 1.01 (d, 3H, J=6 Hz), 0.79 (t, 3H, J=7 Hz).

Example 27

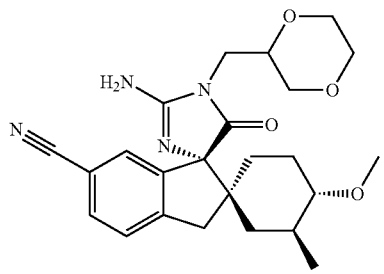 [SMILES: CO[C@H]1CC[C@@]2(Cc3ccc(C#N)cc3[C@]23N=C(N)N(CC2COCCO2)C3=O)C[C@@H]1C]

Example 27 was synthesized by a method as described in Example 6. (1,4-dioxan-2-yl)methanamine was used in step 9 followed by oxidation as described in step 10 to yield Example 27.

LC-MS: tR=0.68 min, MS (ESI) m/z 439 [M+H]$^+$ $^1$H NMR: (CD$_3$OD, 400 MHz) δ 7.67 (not resolved, 1H), 7.48 (d, 1H), 7.20 (not resolved, 1H), 6.66 (s, 2H), 3.78-2.97 (m, 14H), 2.59 (m, 1H), 1.92 (m, 1H), 1.66 (m, 2H), 1.42 (m, 1H), 1.28-1.03 (m, 2H), 0.89 (d, 3H), 0.88 (m, 1H)

Example 28

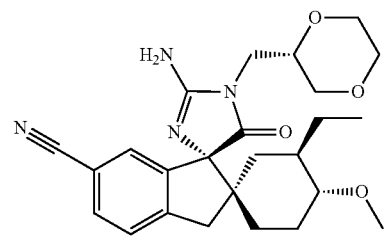 [SMILES: CC[C@@H]1C[C@]2(CC[C@H]1OC)Cc1ccc(C#N)cc1[C@]21N=C(N)N(C[C@H]2COCCO2)C1=O]

Example 28 was synthesized from intermediate 11B from example 1 following the same procedure as in example 1 and utilizing-S-2-(aminomethyl)dioxane in step 9 of example 1.

LC-MS: tR=0.894 min, MS (ESI) m/z 453.2 [M+H]$^+$ $^1$H NMR: (CD$_3$OD): δ 7.63 (dd, J=7.6, 1.2 Hz, 1H), 7.48 (d, J=7.6 Hz, 1H), 7.28 (s, 1H), 3.61-3.85 (m, 8H), 3.58 (s, 3H), 3.56 (s, 1H), 3.17 (m, 2H), 2.77-2.82 (m, 1H), 2.10-2.17 (m, 1H), 1.85-1.88 (m, 1H), 1.69-1.75 (m, 1H), 1.37-1.45 (m, 3H), 1.24-1.34 (m, 2H), 1.09-1.15 (m, 1H), 0.75 (t, J=7.6 Hz, 3H).

Example 29

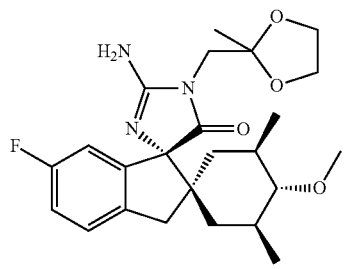 [SMILES: CO[C@H]1[C@H](C)C[C@@]2(Cc3ccc(F)cc3[C@]23N=C(N)N(CC2(C)OCCO2)C3=O)C[C@@H]1C]

Starting with 6-Fluoro-3-indanone, Example 29 was synthesized in a method similar to Example 20.

LC-MS $t_R$=1.02 min; MS (ESI) m/z 446 [M+H]$^+$.

$^1$H NMR (CD$_3$OD): δ 7.26 (dd, J=8.4, 5.2 Hz, 1H), 6.95 (m, 1H), 6.62 (dd, J=8.4, 2.4 Hz, 1H), 4.02-3.89 (m, 4H), 3.70 (d, J=14.8 Hz, 1H), 3.65 (d, J=14.8 Hz, 1H), 3.42 (s, 3H), 3.12 (d, J=15.2 Hz, 1H), 2.98 (d, J=15.2 Hz, 1H), 2.34 (t, J=10.0 Hz, 1H), 1.79-1.60 (m, 3H), 1.43 (m, 1H), 1.34 (m, 1H), 1.32 (m, 1H), 1.30 (s, 3H), 1.00 (m, 1H), 0.99 (d, J=6.8 Hz, 3H), 0.94 (d, J=6.0 Hz, 3H).

What is claimed is:
1. A compound represented by a structural formula selected from:
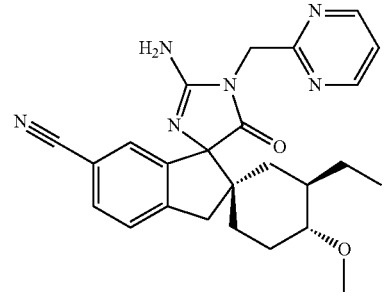
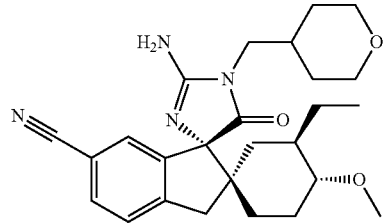
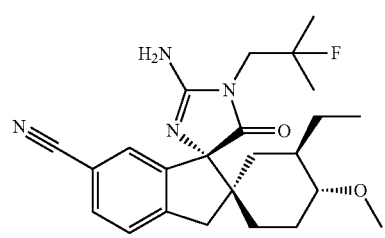
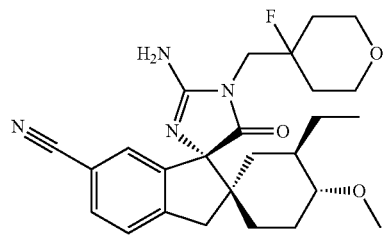
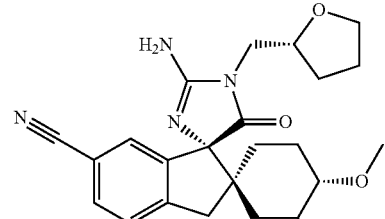
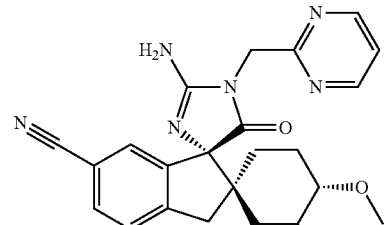
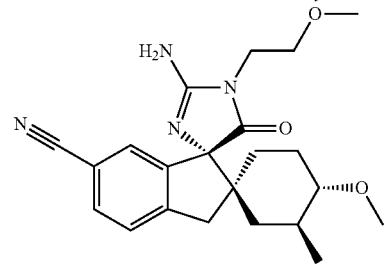
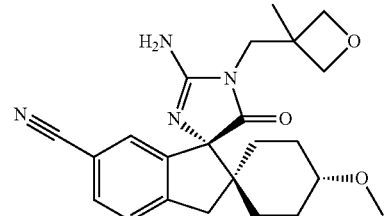
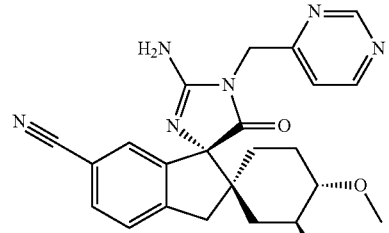

-continued
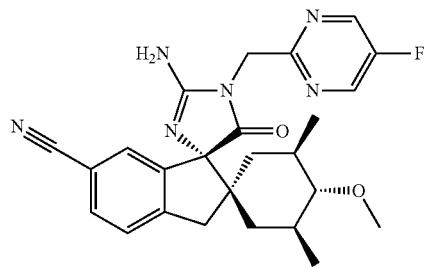
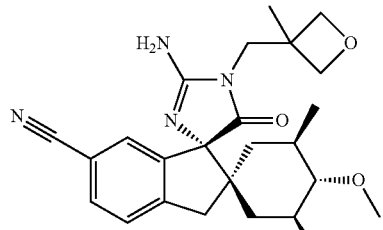
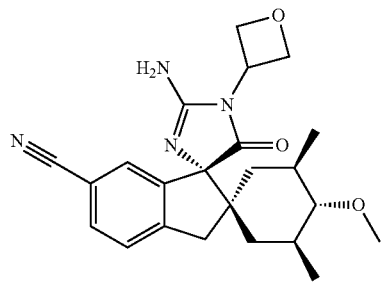
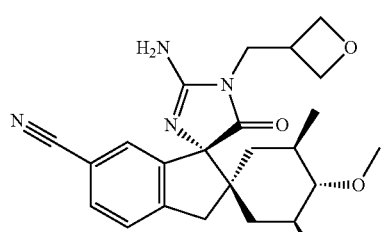
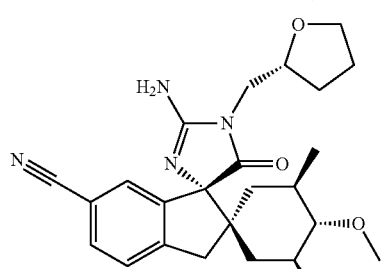
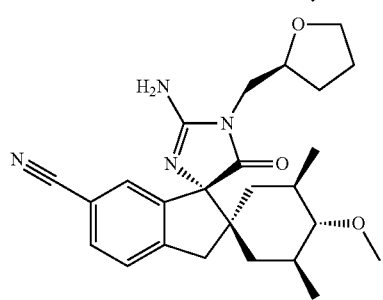
-continued
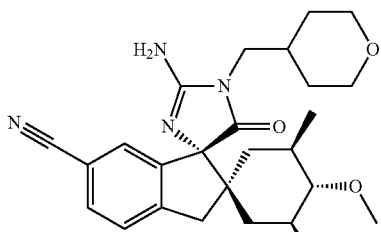
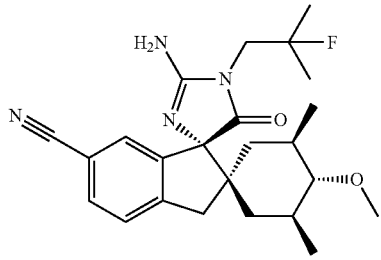
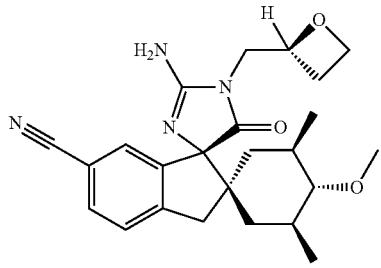
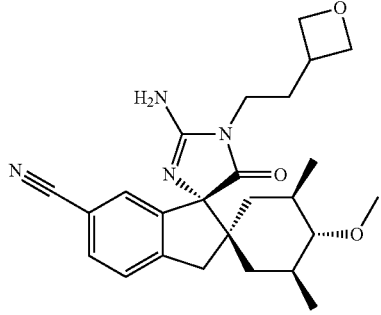
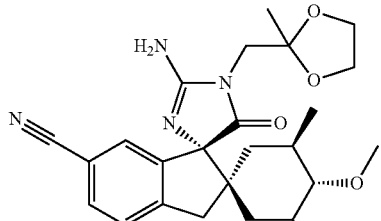
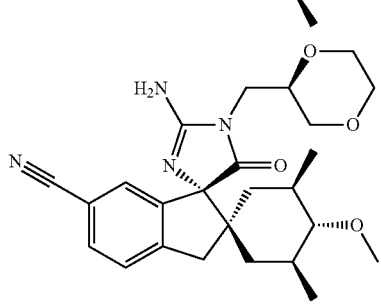

-continued

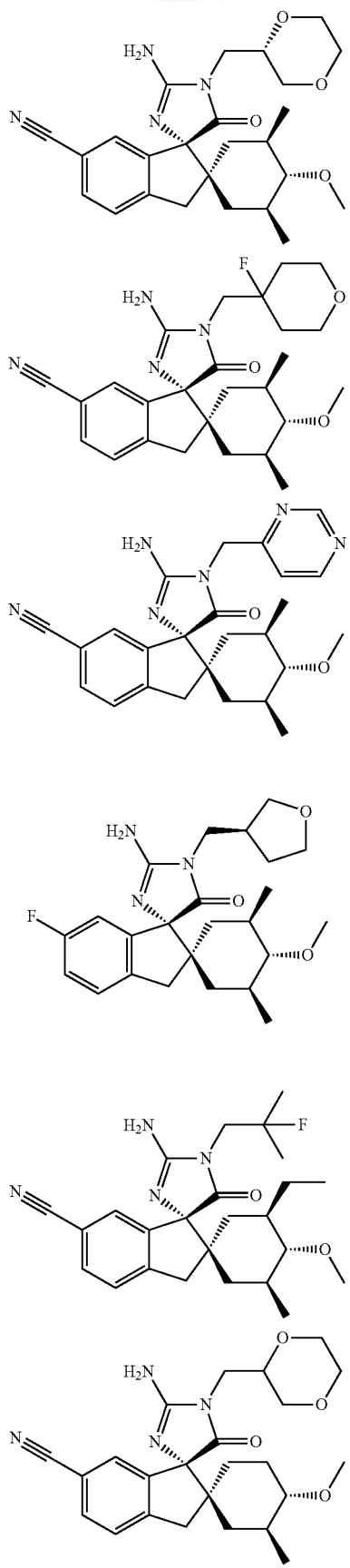

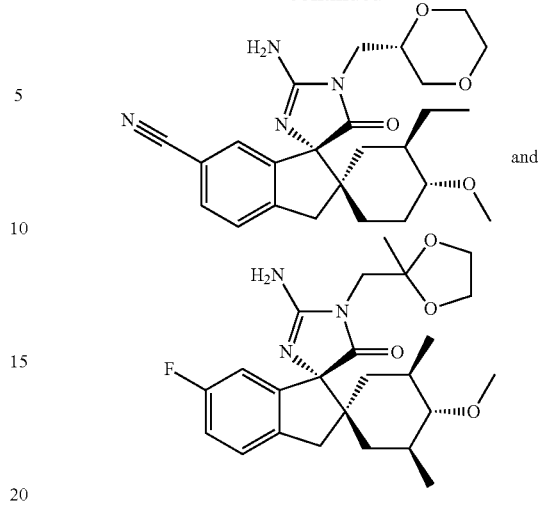

and or a pharmaceutically acceptable salt thereof.

2. A pharmaceutical composition comprising at least one compound according to claim 1 or a pharmaceutically acceptable salt thereof in admixture with a pharmaceutically acceptable adjuvant, diluent and/or carrier.

3. A method of treating a BACE1 mediated disorder or disease in a subject wherein the disorder or disease is selected from the group consisting of Alzheimer's disease and glaucoma, comprising administering to the subject an effective amount of a compound according to claim 1 or a pharmaceutically acceptable salt thereof.

4. The method of claim 3, wherein the disorder or disease is Alzheimer's disease.

5. The method according to claim 3, wherein the disorder or disease is glaucoma.

6. A compound represented by the following structural formula:

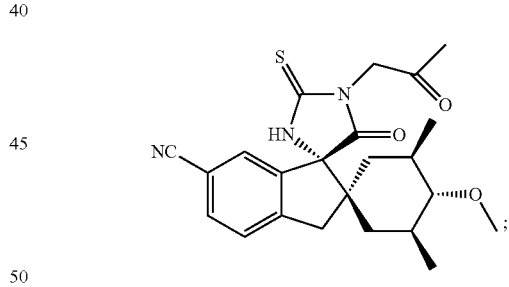

or a salt thereof.

7. A compound represented by the following structural formula:

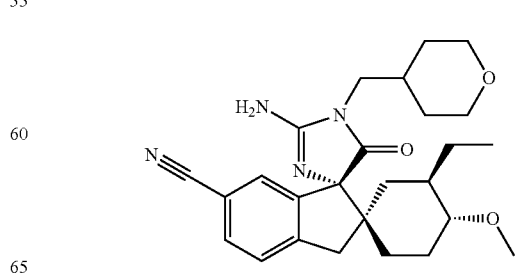

or a pharmaceutically acceptable salt thereof.

8. A compound represented by the following structural formula:

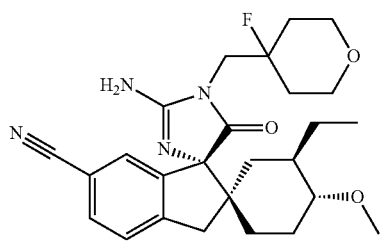 [SMILES: CC[C@@H]1C[C@]2(CC[C@H]1OC)Cc1ccc(C#N)cc1[C@]21N=C(N)N(CC2(F)CCOCC2)C1=O]

or a pharmaceutically acceptable salt thereof.

9. A compound represented by the following structural formula:

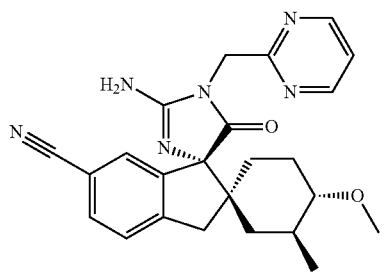 [SMILES: CO[C@H]1CC[C@@]2(Cc3ccc(C#N)cc3[C@]23N=C(N)N(Cc2ncccn2)C3=O)C[C@@H]1C]

or a pharmaceutically acceptable salt thereof.

10. A compound represented by the following structural formula:

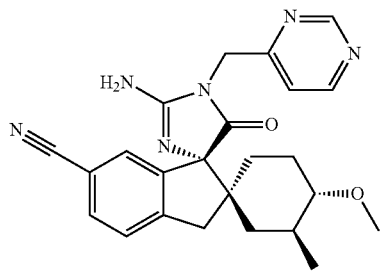 [SMILES: CO[C@H]1CC[C@@]2(Cc3ccc(C#N)cc3[C@]23N=C(N)N(Cc2ccncn2)C3=O)C[C@@H]1C]

or a pharmaceutically acceptable salt thereof.

11. A compound represented by the following structural formula:

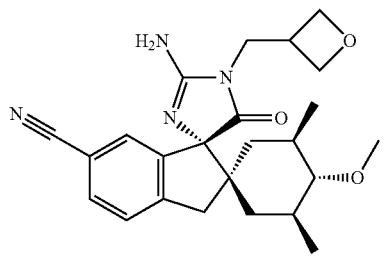 [SMILES: CO[C@H]1[C@H](C)C[C@@]2(Cc3ccc(C#N)cc3[C@]23N=C(N)N(CC2COC2)C3=O)C[C@@H]1C]

or a pharmaceutically acceptable salt thereof.

12. A compound represented by the following structural formula:

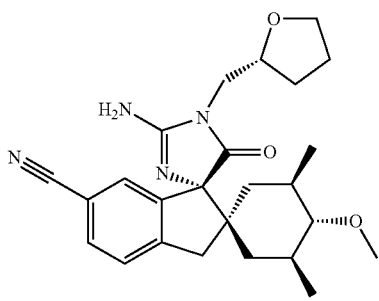 [SMILES: CO[C@H]1[C@H](C)C[C@@]2(Cc3ccc(C#N)cc3[C@]23N=C(N)N(C[C@H]2CCCO2)C3=O)C[C@@H]1C]

or a pharmaceutically acceptable salt thereof.

13. A compound represented by the following structural formula:

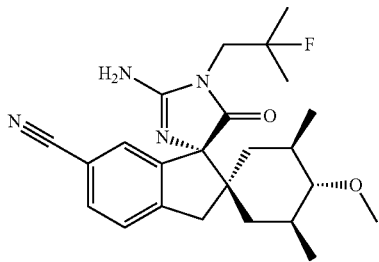 [SMILES: CO[C@H]1[C@H](C)C[C@@]2(Cc3ccc(C#N)cc3[C@]23N=C(N)N(CC(C)(C)F)C3=O)C[C@@H]1C]

or a pharmaceutically acceptable salt thereof.

14. A compound represented by the following structural formula:

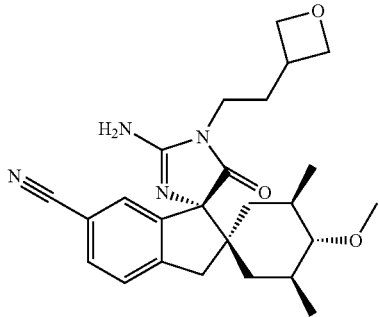 [SMILES: CO[C@H]1[C@H](C)C[C@@]2(Cc3ccc(C#N)cc3[C@]23N=C(N)N(CCC2COC2)C3=O)C[C@@H]1C]

or a pharmaceutically acceptable salt thereof.

15. A compound represented by the following structural formula:

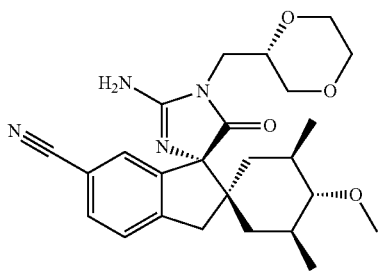 [SMILES: CO[C@H]1[C@H](C)C[C@@]2(Cc3ccc(C#N)cc3[C@]23N=C(N)N(C[C@H]2COCCO2)C3=O)C[C@@H]1C]

or a pharmaceutically acceptable salt thereof.

16. A compound represented by the following structural formula:
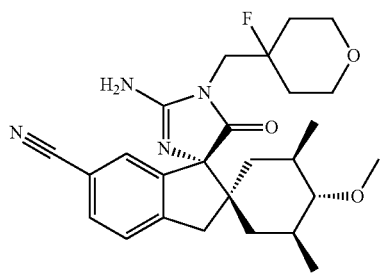 [SMILES: CO[C@H]1[C@H](C)C[C@@]2(Cc3ccc(C#N)cc3[C@]23N=C(N)N(CC2(F)CCOCC2)C3=O)C[C@@H]1C]
or a pharmaceutically acceptable salt thereof.
17. A compound represented by the following structural formula:
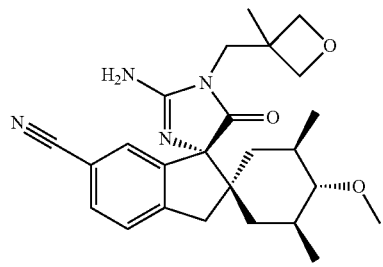 [SMILES: CO[C@H]1[C@H](C)C[C@@]2(Cc3ccc(C#N)cc3[C@]23N=C(N)N(CC2(C)COC2)C3=O)C[C@@H]1C]
or a pharmaceutically acceptable salt thereof.
* * * * *